US009585877B2

(12) United States Patent
Hilt et al.

(10) Patent No.: US 9,585,877 B2
(45) Date of Patent: Mar. 7, 2017

(54) METHODS OF MAINTAINING, TREATING OR IMPROVING COGNITIVE FUNCTION

(71) Applicant: Forum Pharmaceuticals, Inc., Watertown, MA (US)

(72) Inventors: Dana C. Hilt, Waltham, MA (US); Gerhard Koenig, Newton, MA (US)

(73) Assignee: Forum Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 14/399,809

(22) PCT Filed: May 6, 2013

(86) PCT No.: PCT/US2013/039692
§ 371 (c)(1),
(2) Date: Nov. 7, 2014

(87) PCT Pub. No.: WO2013/169646
PCT Pub. Date: Nov. 14, 2013

(65) Prior Publication Data
US 2015/0126547 A1    May 7, 2015

Related U.S. Application Data

(60) Provisional application No. 61/644,113, filed on May 8, 2012, provisional application No. 61/670,087, filed on Jul. 10, 2012.

(51) Int. Cl.
A61K 31/40       (2006.01)
A61K 31/439      (2006.01)
A61K 31/55       (2006.01)

(52) U.S. Cl.
CPC ............ A61K 31/439 (2013.01); A61K 31/55 (2013.01)

(58) Field of Classification Search
CPC .................................................. A61K 31/439
USPC ....................................................... 514/412
See application file for complete search history.

(56) References Cited

U.S. PATENT DOCUMENTS

| | | | |
|---|---|---|---|
| 4,605,652 A | 8/1986 | Welstead, Jr. | |
| 4,721,720 A | 1/1988 | Wootton et al. | |
| 4,783,478 A | 11/1988 | Wootton et al. | |
| 4,851,407 A | 7/1989 | Wootton et al. | |
| 4,985,420 A | 1/1991 | Hamminga et al. | |
| 5,069,904 A | 12/1991 | Masterson | |
| 5,114,947 A | 5/1992 | Imondi | |
| 5,122,528 A | 6/1992 | Imondi | |
| 5,198,437 A | 3/1993 | Hamminga et al. | |
| 5,561,149 A | 10/1996 | Azria et al. | |
| 5,599,937 A | 2/1997 | Glas et al. | |
| 5,656,638 A | 8/1997 | Gaeta et al. | |
| 5,703,116 A | 12/1997 | Gaeta et al. | |
| 5,760,062 A | 6/1998 | Gaeta et al. | |
| 5,863,936 A | 1/1999 | Gaeta et al. | |
| 5,902,814 A | 5/1999 | Gordon et al. | |
| 5,977,144 A | 11/1999 | Meyer et al. | |
| 6,051,581 A | 4/2000 | Gordon et al. | |
| 6,232,319 B1 | 5/2001 | Marazano et al. | |
| 6,277,870 B1 | 8/2001 | Gurley et al. | |
| 6,358,941 B1 | 3/2002 | Snorrason et al. | |
| 6,416,735 B1 | 7/2002 | Carroll et al. | |
| 6,479,510 B2 | 11/2002 | Myers et al. | |
| 6,492,385 B2 | 12/2002 | Myers et al. | |
| 6,500,840 B2 | 12/2002 | Myers et al. | |
| 6,569,865 B2 | 5/2003 | Eifion | |
| 6,780,861 B2 | 8/2004 | Nozulak | |
| 6,861,443 B2 | 3/2005 | Gurley et al. | |
| 6,869,958 B2 | 3/2005 | Li | |
| 6,875,606 B1 | 4/2005 | Leonard et al. | |
| 6,908,927 B2 | 6/2005 | Galli et al. | |
| 6,911,543 B2 | 6/2005 | Walker et al. | |
| 6,943,184 B2 | 9/2005 | Goldstein et al. | |
| 6,953,855 B2 | 10/2005 | Mazurov et al. | |
| 6,964,961 B2 | 11/2005 | Luzzio et al. | |
| 6,964,972 B2 | 11/2005 | Peters et al. | |
| 6,987,106 B1 | 1/2006 | Gallet et al. | |
| 6,995,167 B2 | 2/2006 | Loch, III et al. | |
| 7,067,261 B2 | 6/2006 | Bencherif et al. | |
| 7,067,515 B2 | 6/2006 | Wishka et al. | |
| 7,196,096 B2 | 3/2007 | Loch, III et al. | |
| 7,214,686 B2 | 5/2007 | Bencherif et al. | |
| 7,256,288 B2 | 8/2007 | Hendrix et al. | |
| 7,358,057 B2 | 4/2008 | Wang et al. | |
| 7,579,362 B2 | 8/2009 | Feuerbach et al. | |
| 7,732,477 B2 | 6/2010 | Hendrix et al. | |
| 7,767,193 B2 | 8/2010 | Mazurov et al. | |
| 7,795,453 B2 | 9/2010 | Flessner et al. | |

(Continued)

FOREIGN PATENT DOCUMENTS

| | | |
|---|---|---|
| AU | 200145207 | 6/2001 |
| AU | 2002316828 | 10/2002 |

(Continued)

OTHER PUBLICATIONS

International Search Report dated Oct. 11, 2013 for PCT/US2013/039692.
Acker, Brad A. et al., "Discovery of N-[(3R,5R)-1-azabicyclo[3.2.1]oct-3-yl]furo[2,3-c]pyridine-5-carboxamide as an agonist of the α7 nicotinic acetylcholine receptor: In vitro and in vivo activity," Bioorganic & Medicinal Chemistry Letters, 18:12 (Jun. 2008) 3611-3615.
Adler, et al., "Normalization of auditory physiology by cigarette smoking in schizophrenic patients," Am J Psychiatry, 150 (1993) 1856-1861.
Adler, et al., "Schizophrenia, sensory gating, and nicotinic receptors," Schizophr Bull, 24 (1998) 189-202.
Ahnallen, Christopher G. "The role of the α7 nicotinic receptor in cognitive processing of persons with schizophrenia," Current Opinion Psychiatry, 25:2 (Mar. 2012) 103-108.

(Continued)

Primary Examiner — Kevin E Weddington
(74) Attorney, Agent, or Firm — Jones Day

(57) ABSTRACT

A method of administering an effective amount of (R)-7-chloro-N-(quinuclidin-3-yl)benzo[b]thiophene-2-carboxamide, or a pharmaceutically acceptable salt thereof, to a patient in need thereof.

40 Claims, 15 Drawing Sheets

(56) References Cited

U.S. PATENT DOCUMENTS

| | | | |
|---|---|---|---|
| 7,902,222 B2 | 3/2011 | Ji et al. | |
| 7,935,815 B2 | 5/2011 | Kimura et al. | |
| 7,964,607 B2 | 6/2011 | Verhoest et al. | |
| 8,076,355 B2 | 12/2011 | Hendrix et al. | |
| 8,084,462 B2 | 12/2011 | Mazurov et al. | |
| 8,124,618 B2 | 2/2012 | Mazurov et al. | |
| 8,124,619 B2 | 2/2012 | Mazurov et al. | |
| 8,124,620 B2 | 2/2012 | Mazurov et al. | |
| 8,569,354 B2 * | 10/2013 | Chesworth | A61K 31/439 514/412 |
| 8,815,933 B2 * | 8/2014 | Chesworth | A61K 31/439 514/412 |
| 2002/0052389 A1 | 5/2002 | Myers et al. | |
| 2003/0092613 A1 | 5/2003 | Lee et al. | |
| 2003/0119840 A1 | 6/2003 | Galli et al. | |
| 2004/0019053 A1 | 1/2004 | Roark | |
| 2004/0039045 A1 | 2/2004 | Schiemann et al. | |
| 2004/0043983 A1 | 3/2004 | Li | |
| 2004/0249150 A1 | 12/2004 | Piotrowski et al. | |
| 2004/0254373 A1 | 12/2004 | Piotrowski et al. | |
| 2004/0266757 A1 | 12/2004 | Galli et al. | |
| 2005/0004128 A1 | 1/2005 | Galli et al. | |
| 2005/0020599 A1 | 1/2005 | Galli et al. | |
| 2005/0031651 A1 | 2/2005 | Gervais et al. | |
| 2005/0032845 A1 | 2/2005 | Goldstein et al. | |
| 2005/0107460 A1 | 5/2005 | Luithle et al. | |
| 2005/0119249 A1 | 6/2005 | Buntinx | |
| 2005/0119325 A1 | 6/2005 | Hendrix et al. | |
| 2005/0154045 A1 | 7/2005 | Luithle et al. | |
| 2005/0209236 A1 | 9/2005 | Hendrix et al. | |
| 2005/0245504 A1 | 11/2005 | Corbett et al. | |
| 2005/0245531 A1 | 11/2005 | Ji et al. | |
| 2005/0250816 A1 | 11/2005 | Piotrowski et al. | |
| 2006/0160835 A1 | 7/2006 | Bencherif et al. | |
| 2006/0167002 A1 | 7/2006 | Feuerbach et al. | |
| 2007/0037844 A1 | 2/2007 | Luithle et al. | |
| 2007/0274628 A1 | 11/2007 | Borschke | |
| 2009/0054446 A1 | 2/2009 | Feuerbach et al. | |
| 2009/0088418 A1 | 4/2009 | Pfister et al. | |
| 2009/0221555 A1 | 9/2009 | Ahmed et al. | |
| 2010/0004162 A1 | 1/2010 | Heintz et al. | |
| 2010/0130540 A1 | 5/2010 | Duggan | |
| 2010/0152108 A1 | 6/2010 | Hung et al. | |
| 2010/0190771 A1 | 7/2010 | Claffey et al. | |
| 2010/0222378 A1 | 9/2010 | Hendrix et al. | |
| 2010/0261752 A1 | 10/2010 | Beattie et al. | |
| 2010/0324085 A1 | 12/2010 | Flessner et al. | |
| 2011/0009619 A1 | 1/2011 | Kimura et al. | |
| 2011/0021590 A1 | 1/2011 | Duggan | |
| 2011/0065696 A1 | 3/2011 | Kimura et al. | |
| 2011/0124631 A1 | 5/2011 | Koenig et al. | |
| 2011/0262442 A1 | 10/2011 | Hamilton et al. | |
| 2011/0269764 A1 | 11/2011 | Cohen et al. | |
| 2011/0274628 A1 | 11/2011 | Borschke | |
| 2011/0305751 A1 | 12/2011 | Gaillard | |
| 2012/0010148 A1 | 1/2012 | Gozes et al. | |
| 2012/0046283 A1 | 2/2012 | Campbell et al. | |
| 2012/0053171 A1 | 3/2012 | Kitazawa et al. | |
| 2012/0058992 A1 | 3/2012 | Cohen et al. | |
| 2012/0071483 A1 | 3/2012 | Cohen et al. | |
| 2012/0202842 A1 | 8/2012 | Hendrix et al. | |

FOREIGN PATENT DOCUMENTS

| | | |
|---|---|---|
| CA | 2317025 | 6/2000 |
| CA | 2393004 | 6/2001 |
| CA | 2393538 | 6/2001 |
| CA | 2460075 | 3/2003 |
| CA | 2475773 | 3/2003 |
| CA | 2464194 | 5/2003 |
| CA | 2465680 | 5/2003 |
| CA | 2466344 | 5/2003 |
| CA | 2466375 | 5/2003 |
| CA | 2476417 | 8/2003 |
| CA | 2476624 | 8/2003 |
| CA | 2476681 | 8/2003 |
| DE | 3724059 | 2/1988 |
| DE | 3740984 | 6/1989 |
| DE | 3810552 | 10/1989 |
| DE | 10044905 | 3/2002 |
| DE | 10156719 | 5/2003 |
| DE | 10162442 | 7/2003 |
| EP | 0322016 | 6/1989 |
| EP | 0327335 | 8/1989 |
| EP | 0353371 | 2/1990 |
| EP | 0405617 | 1/1991 |
| EP | 0485962 | 5/1992 |
| EP | 0512350 | 11/1992 |
| EP | 1022029 | 7/2000 |
| EP | 2002-030084 | 1/2002 |
| EP | 1219622 | 7/2002 |
| EP | 1231212 | 8/2002 |
| EP | 2277850 | 1/2011 |
| GB | 2208862 | 4/1989 |
| GB | 2231265 | 11/1990 |
| JP | 11080027 | 3/1999 |
| JP | 2002030084 | 1/2002 |
| JP | 2003081978 | 3/2003 |
| WO | WO 91/09593 | 7/1991 |
| WO | WO 93/15073 | 8/1993 |
| WO | WO 96/33186 | 10/1996 |
| WO | WO 97/30998 | 8/1997 |
| WO | WO 99/03859 | 1/1999 |
| WO | WO 99/45926 | 9/1999 |
| WO | WO 99/62505 | 12/1999 |
| WO | WO 00/10997 | 3/2000 |
| WO | WO 01/29034 | 4/2001 |
| WO | WO 01/32619 | 5/2001 |
| WO | WO 01/32620 | 5/2001 |
| WO | WO 01/32622 | 5/2001 |
| WO | WO 01/36417 | 5/2001 |
| WO | WO 01/55150 | 8/2001 |
| WO | WO 01/60821 | 8/2001 |
| WO | WO 01/66546 | 9/2001 |
| WO | WO 02/15662 | 2/2002 |
| WO | WO 02/16357 | 2/2002 |
| WO | WO 02/20016 | 3/2002 |
| WO | WO 02/44176 | 6/2002 |
| WO | WO 02/057275 | 7/2002 |
| WO | WO 02/085901 | 10/2002 |
| WO | WO 02/096912 | 12/2002 |
| WO | WO 02/100857 | 12/2002 |
| WO | WO 02/100858 | 12/2002 |
| WO | WO 03/018585 | 3/2003 |
| WO | WO 03/029252 | 4/2003 |
| WO | WO 03/037896 | 5/2003 |
| WO | WO 03/044019 | 5/2003 |
| WO | WO 03/044020 | 5/2003 |
| WO | WO 03/044024 | 5/2003 |
| WO | WO 03/051874 | 6/2003 |
| WO | WO 03/055878 | 7/2003 |
| WO | WO 03/072578 | 9/2003 |
| WO | WO 03/078430 | 9/2003 |
| WO | WO 03/078431 | 9/2003 |
| WO | WO 03/087102 | 10/2003 |
| WO | WO 03/087103 | 10/2003 |
| WO | WO 03/087104 | 10/2003 |
| WO | WO 03/091694 | 11/2003 |
| WO | WO 03/093250 | 11/2003 |
| WO | WO 03/094830 | 11/2003 |
| WO | WO 03/094831 | 11/2003 |
| WO | WO 03/104227 | 12/2003 |
| WO | WO 2004/013137 | 2/2004 |
| WO | WO 2004/016608 | 2/2004 |
| WO | WO 2004/016616 | 2/2004 |
| WO | WO 2004/016617 | 2/2004 |
| WO | WO 2004/019943 | 3/2004 |
| WO | WO 2004/019947 | 3/2004 |
| WO | WO 2004/029050 | 4/2004 |
| WO | WO 2004/039321 | 5/2004 |
| WO | WO 2004/039815 | 5/2004 |
| WO | WO 2004/043960 | 5/2004 |
| WO | WO 2004/052348 | 6/2004 |

(56) References Cited

FOREIGN PATENT DOCUMENTS

| | | |
|---|---|---|
| WO | WO 2004/052461 | 6/2004 |
| WO | WO 2004/052889 | 6/2004 |
| WO | WO 2004/052894 | 6/2004 |
| WO | WO 2004/056744 | 7/2004 |
| WO | WO 2004/064836 | 8/2004 |
| WO | WO 2004/085433 | 10/2004 |
| WO | WO 2005/012299 | 2/2005 |
| WO | WO 2005/092890 | 10/2005 |
| WO | WO 2005/117890 | 12/2005 |
| WO | WO 2006/010008 | 1/2006 |
| WO | WO 2006/030031 | 3/2006 |
| WO | WO 2006/065233 | 6/2006 |
| WO | WO 2006/066879 | 6/2006 |
| WO | WO 2007/038367 | 4/2007 |
| WO | WO 2008/100867 | 8/2008 |
| WO | WO 2009/018505 | 2/2009 |
| WO | WO 2009/073788 | 6/2009 |
| WO | WO 2009/091932 | 7/2009 |
| WO | WO 2010/059844 | 5/2010 |
| WO | WO 2010059844 A1 * 5/2010 ........... A61K 31/439 |
| WO | WO 2010/098488 | 9/2010 |
| WO | WO 2010/098495 | 9/2010 |
| WO | WO 2010/132423 | 11/2010 |
| WO | WO 2011/009097 | 1/2011 |
| WO | WO 2011/033018 | 3/2011 |
| WO | WO 2011/036167 | 3/2011 |
| WO | WO 2011/044264 | 4/2011 |
| WO | WO 2011/044535 | 4/2011 |
| WO | WO 2011/044537 | 4/2011 |
| WO | WO 2011/047432 | 4/2011 |
| WO | WO 2011/054759 | 5/2011 |
| WO | WO 2011/063415 | 5/2011 |
| WO | WO 2011/064288 | 6/2011 |
| WO | WO 2011/084368 | 7/2011 |
| WO | WO 2011/139811 | 11/2011 |
| WO | WO 2011/146511 | 11/2011 |
| WO | WO 2011/156640 | 12/2011 |
| WO | WO 2011/156646 | 12/2011 |
| WO | WO 2011/156775 | 12/2011 |
| WO | WO 2011/156780 | 12/2011 |
| WO | WO 2011/156786 | 12/2011 |
| WO | WO 2011/159945 | 12/2011 |
| WO | WO 2012/015749 | 2/2012 |

OTHER PUBLICATIONS

Anderson et al., "Tools for Purifying the Product: Column Chromatography, Crystallization and Reslurrying," *Practical Process Research and Development*, Academic Press, San Diego (Jan. 1, 2000) 223-247.

Araki, Hiroaki et al. "Neuronal nicotinic receptor and psychiatric disorders: Functional and behavioral effects of nicotine," *Japanese J Pharmacol*, 88 (2002) 133-138.

Arendash, Gary W. et al. "Improved learning and memory in aged rats with chronic administration of the nicotinic receptor agonist GTS-21," *Brain Research*, 674 (1995) 252-259.

Baldeweg, et al. "Nicotinic modulation of human auditory sensory memory: Evidence from mismatch negativity potentials," *Int J Psychophysiol*, 59 (2006) 49-58.

Banerjee, Carolin et al. "Cellular expression of α7 nicotinic acetylcholine receptor protein in the temporal cortex in Alzheimer's and Parkinson's Disease—A stereological approach," *Neurobiology of Disease*, 7 (2000) 666-672.

Bednar, Ivan et al. "Selective nicotinic receptor consequences in APP$_{SWE}$ transgenic mice," *Molecular Cell Neurosci*, 20 (2002) 354-365.

Belluardo, N. et al. "Neurotrophic effects of central nicotinic receptor activation," *J Neural Transmission* [Supplement], 60 (2000) 227-245.

Belluardo, Natale et al. "Central nicotinic receptors, neurotrophic factors and neuroprotection," *Behavioural Brain Res*, 113 (2000) 21-34.

Bhat, B. et al., "A Novel One-Step Synthesis of 2-Methoxycarbonyl-thieno[2,3-b]quinolines and 3-Hydroxy-2-methoxycarbonyl-2,3-dihydrothieno[2,3-b]-quinolines," *Synthesis* (Aug. 1984) 673-676.

Bitner, R. Scott et al. "In vivo pharmacological characterization of a novel selective α7 neuronal nicotinic acetylcholine receptor agonist ABT-107: Preclinical considerations in Alzheimer's disease," *J Pharmacol Exp Ther*, 334:3 (2010) 875-886.

Bitner, Robert S. et al. "Broad-spectrum efficacy across cognitive domains by α7 nicotinic acetylcholine receptor agonism correlates with activation of ERK1/2 and CREB phosphorylation pathways," *J Neurosci*, 27:39 (Sep. 26, 2007) 10578-10587.

Biton, Bruno et al. "SSR180711, a novel selective α7 nicotinic receptor partial agonist: (I) Binding and functional profile," *Neuropsychopharmacology*, 32 (2007) 1-16.

Bjugstad, Kimberly B. et al. "Long-term treatment with GTS-21 or nicotine enhances water maze performance in aged rats without affecting the density of nicotinic receptor subtypes in neocortex," *Drug Dev Research*, 39 (1996) 19-28.

Blokland, A. et al., "State-dependent impairment in object recognition after hippocampal NOS inhibition," *NeuroReport*, 8:18 (Dec. 1998) 4205-4208.

Bodnar, Alice et al. "Discovery and structure—activity relationship of quinuclidine benzamides as agonists of α7 nicotinic acetylcholine receptors," *J Med Chem*, 48 (2005) 905-908.

Boess et al., "Inhibition of phosphodiesterase 2 increases neuronal cGMP, synaptic plasticity and memory performance," *Neuropharmacology*, 47 (2004) 1081-1092.

Boess, Frank G. et al. "The novel α7 nicotinic acetylcholine receptor agonist N-[(3R)-1-azabicyclo[2.2.2]oct-3-yl]-7-[2-(methoxy)phenyl]-1-benzofuran-2-carboxamide improves working and recognition memory in rodents," *J Pharmacol Exp Ther*, 321:2 (2007) 716-725.

Bogdal, D. et al., "Microwave-Assisted Preparation of Benzo[b]furans under Solventless Phase-Transfer Catalytic Conditions," *Tetrahedron*, 56 (2000) 8769-8773.

Boutros, et al. "Test-retest reliability of the P50 mid-latency auditory evoked response," *Psychiatry Res*, 39 (1991) 181-192.

Bridges, A.J. et al., "Fluorine as an Ortho-Directing Group in Aromatic Metalation: A Two Step Preparation of Substituted Benzo[b]thiophene-2-carboxylates" *Tetrahedron Letters*, 33:49 (1992) 7499-7502.

Briggs, Clark A. et al. "Functional characterization of the novel neuronal nicotinic acetylcholine receptor ligand GTS-21 in vitro and in vivo," *Pharmacol Biochem Behavior*, 57:1/2 (1997) 231-241.

Brittain, H.G., ed., "Methods for the Characterization of Polymorphs and Solvates," *Polymorphism in Pharmaceutical Solids* (Jan. 1, 1999) 227-278.

Brittain, H.G., ed., *Polymorphism in Pharmaceutical Solids, 2nd Edition* (2009) 318-335.

Broide, R.S. et al., "The α7 Nicotinic Acetylcholine Receptor in Neuronal Plasticity," *Molecular Neurobiology*, vol. 20 (1999) 1-16.

Buccafusco et al., "Desensitization of Nicotinic Acetylcholine Receptors as a Strategy for Drug Development," *J of Pharm. and Exp. Ther.*, 328:2 (2009) 364-370.

Byrn, S. et al. "Pharmaceutical Solids: A Strategic Approach to Regulatory Considerations," *Pharmaceutical Research*, Kluwer Academic Publishers, New York, 12:7 (Jul. 1, 1995) 945-954.

Caira, M.R. "Crystalline Polymorphism of Organic Compounds," *Topics in Current Chemistry*, vol. 198 (Jan. 1, 1998) 163-208.

Cehn, Y. et al. "Nicotine and an α7 selective nicotinic agonist AR-R17779 facilitate the induction of long-term potentiation induced by a short tetanus," *Soc Neuroscience*, Program No. 420.3 (Nov. 7, 2000). (Abstract only).

Krutcher, Keith A. "GTS-21" *Current Opinion in Central Peripheral Nervous System Investigational Drugs*, 2:4 (2000) 478-484.

Cummings, J. L. "Cholinesterase inhibitors: A new class of psychotropic compounds," *American Journal of Psychiatry*, 157:1 (Jan. 2000) 4-15.

D'Andrea, Michael R. et al. "Targeting intracellular Aβ42 for Alzheimer's Disease drug discovery," *Drug Dev Research*, 56 (2002) 194-200.

(56) References Cited

OTHER PUBLICATIONS

Dalebout, et al. "Reliability of the mismatch negativity in the responses of individual listeners," *J Am Acad Audiol*, 12 (2001) 245-253.

Dance, Amber et al. "The society for neuroscience 2009 meeting report, part 2," *J Alzheimers Disease*, 19 (2010) 1409-1415.

Davies, A.R.L. et al., "Characterisation of the binding of [$^3$H]methyllycaconitine: a new radioligand for labelling α7-type neuronal nicotinic acetylcholine recestors" *Neuropharmacology*, 38 (1999) 679-690.

De Bruin et al., "SLV330: A cannabinoid CB1 receptor antagonist, ameliorates deficits in the T-maze, object recognition and social recognition tasks in rodents," *Neurobiol Learn Mem*, 93 (2010) 522-531.

De Strooper, Bart et al. "The secretases: Enzymes with therapeutic potential in Alzheimer disease," *Nature Rev: Neurol*, 6 (Feb. 2010) 99-107.

De Wilde, et al., "A meta-analysis of P50 studies in patients with schizophrenia and relatives: differences in methodology between research groups," *Schizophr Res*, 97 (2007) 137-151.

Dierks, et al., "Event-related potentials and psychopharmacology: Cholinergic modulation of P300," *Pharmacopsychiatry*, 27 (1994) 72-74.

Dunbar, et al., "Effects of TC-1734 (AZD3480), a selective neuronal nicotinic receptor agonist, on cognitive performance and the EEG of young healthy male volunteers," *Psychopharmacology* (Berl), 191 (2007) 919-929.

Duncan et al., "Effects of smoking on acoustic startle and prepulse inhibition in humans," *Psychopharmacology* (Berl), 156 (2001) 266-272.

Easton, et al., "Beneficial effects of thiamine on recognition memory and P300 in abstinent cocaine-dependent patients," *Psychiatry Res*, 70 (1997) 165-174.

Ennaceur et al., "A new one-trial test for neurobiological studies of memory in rats. II: Effects of piracetam and pramiracetam," *Behav Brain Res*, 33 (1989) 197-207.

Ennaceur, A. et al., "A new one-trial test for neurobiological studies of memory in rats. 1: Behavioral data," *Behavioural Brain Research*, vol. 31 (1988) 47-59.

Ennaceur, A. et al., "Effects of physostigmine and scopolamine on rats' performances in object-recognition and radial-maze tests," *Psychopharmacology*, vol. 109 (1992) 321-330.

Feuerbach, D. et al. "The selective nicotinic acetylcholine receptor alpha7 agonist JN403 is active in animal models of cognition, sensory gating, epilepsy and pain," *Neuropharmacology*, 56:1 (Jan. 1, 2009) 254-263.

Folstein, Marshal et al., "'Mini-Mental State': A Practical Method for Grading the Cognitive State of Patients for the Clinician," *Journal of Psychiatric Research*, 12 (1975) 189-98.

Freedman et al., "Linkage disequilibrium for schizophrenia at the chromosome 15q13-14 locus of the α7-nicotinic acetylcholine receptor subunit gene (CHRNA7)," *Am J Med Genet*, 105 (2001) 20-22.

Freedman, Robert et al. "Initial phase 2 trial of a nicotinic agonist in schizophrenia," *Am J Psychiatry*, 165 (2008) 1040-1047.

Fuerst et al., "Range of sensory gating values and test-retest reliability in normal subjects," *Psychophysiology*, 44 (2007) 620-626.

Galasko, Douglas et al., "An Inventory to Assess Activities of Daily Living for Clinical Trials in Alzheimer's Disease," *Alzheimer Disease and Associated Disorders*, 11:S2 (1997) S33-S39.

Galzi, J.L. et al., "Neuronal Nicotinic Receptors: Molecular Organization and Regulations," *Neuropharmacology*, 34:6 (1995) 563-582.

George, Tony et al. "Nicotinic modulation of mesoprefrontal dopamine neurons: Pharmacologic and neuroanatomic characterization," *J Pharmacol Exp Ther*, 295:1 (2000) 58-66.

Gray, J.A. et al. "The pipeline and future of drug development in schizophrenia," *Molecular Psychiatry*, 12:10 (Oct. 2007) 904-922.

Gray, Richard et al. "Hippcampal synaptic transmission enhanced by low concentrations of nicotine," *Nature*, 383 (Oct. 1996) 713-716.

Guillory, J. K. "Generation of Polymorphs, Hydrates, Solvates and Amorphous Solids," *Polymorphism in Pharmaceutical Solids* (Jan. 1, 1999) 183-226.

Harwood, L. M. et al. "Experimental organic chemistry—Principles and Practice," *Experimental Chemistry—Organic Chemistry and Reaction* (Jan. 1, 1989) 127-132.

Hauser, T.A. et al. "TC-5619: An alpha7 neuronal nicotinic receptor-selective agonist that demonstrates efficacy in animal models of the positive and negative symptoms and cognitive dysfunction of schizophrenia," *Biochemical Pharmacology*, 78:7 (Oct. 1, 2009) 803-812.

Haydar, Simon N. et al. "Neuronal nicotinic acetylcholine receptors—Targets for the development of drugs to treat cognitive impairment associated with schizophrenia and Alzheimer's disease," *Curr Topics Med Chem*, 10 (2010) 144-152.

Heinrichs, R.W., "Meta-analysis and the science of schizophrenia: variant evidence or evidence of variants?" *Neurosci Biobehav Rev*, 28 (2004) 379-394.

Ho, Yuan-Soon et al. "The alpha-9 nicotinic acetylcholine receptor serves as a molecular target for breast cancer therapy," *J Exp Clin Med*, 3:6 (2011) 246-251.

Huang, Mei et al. "The alpha-7 receptor agonist EVP-6124 increases dopamine and glutamate efflux in rat medial prefrontal cortex and nucleus accumbens," *Biochem Pharmacol*, 82:2.13 (2011) 1040 (Abstract only).

Hughes, Charles P. et al., "A New Clinical Scale for the Staging of Dementia," *Brit. J. Psychiat.*, 140 (1982) 566-572.

Ishikawa, Masatomo et al. "α7 Nicotinic acetylcholine receptor as a potential therapeutic target for schizophrenia," *Curr Pharmaceut Design*, 17 (2011) 121-129.

Ivanisevic, Igor et al., "Uses of X-Ray Powder Diffraction in the Pharmaceutical Industry," *Pharmaceutical Formulation and Quality* (Aug./Sep. 2011) 32-33.

Ji, Daoyun et al. "Timing and location of nicotinic activity enhances or depresses hippocampal synaptic plasticity," *Neuron*, 31 (Jul. 2001) 131-141.

Kaga et al., "Cat P300 and cholinergic septohippocampal neurons: depth recordings, lesions, and choline acetyltransferase immunohistochemistry," *Neurosci Res*, 13 (1992) 53-71.

Katada et al., "Long-term effects of donepezil on P300 auditory event-related potentials in patients with Alzheimer's disease," *J Geriatr Psychiatry Neurol*, 16 (2003) 39-43.

Kawamata, Jun et al. "Stimulating nicotinic receptors trigger multiple pathways attenuating cytotoxicity in models of Alzheimer's and Parkinson's diseases," *J Alzheimers Disease*, 24 (2011) 95-109.

Kem, William R. "The brain α7 nicotinic receptor may be an important therapeutic target for the treatment of Alzheimer's Disease: Studies with DMXBA (GTS-21)," *Behavioural Brain Res*, 113 (2000) 169-181.

Kem, William R. et al. "Hydroxy metabolites of the Alzheimer's drug candidate 3-[(2,4-dimethoxy)benzylidene]-anabaseine dihydrochloride (GTS-21): Their molecular properties, interactions with brain nicotinic receptors, and brain penetration," *Mol Pharmacol*, 65:1 (2004) 56-67.

Kitagawa, Harumi et al. "Safety, pharmacokinetics, and effects on cognitive function of multiple doses of GTS-21 in healthy male volunteers," *Neuropsychopharmacology*, 28 (2003) 542-551.

Koenig, G. et al. "EVP-6124, a novel and potent α7 nicotinic acetylcholine receptor agonist, improves memory acquisition, retention and retrieval and reverses scopolamine-induced memory deficits," *Soc Neuroscience*, Abst 887.6/FF136 (Oct. 21, 2009) 1-4.

Lanctôt, Krista L. et al. "Therapy for Alzheimer's disease: How effective are current treatments?" *Therapeut Adv Neurol Disorders*, 2:3 (2009) 163-180.

Levin, E. D. et al. "AR-R17779, an α7 nicotinic agonist, improves memory and learning in rats," *Behavioural Pharmacol*, 10 (1999) 675-780.

Levin, Edward D. et al. "Development of nicotinic drug therapy for cognitive disorders," *Euro J Pharmacol*, 393 (2000) 141-146.

(56) References Cited

OTHER PUBLICATIONS

Levin, Edward et al. "Nicotinic treatment for cognitive dysfunction," *Curr Drug Targets—CNS & Neurol Disord*, 1 (2002) 423-431.
Levin, Edward, "Nicotinic receptor subtypes and cognitive function," *J Neurobiology* 53 (2002) 633-640.
Li, X. D. et al. "Blood pressure and heart rate responses to central injection of choline: Role of α7-nicotinic cholinergic receptors," *Soc Neuroscience*, Program No. 136.6 (Nov. 3, 2002).(Abstract only).
Liu, Qing-song et al. "β-Amyloid peptide blocks the response of α7-containing nicotinic receptors on hippocampal neurons," *Proc Natl Acad Sci*, 98:8 (2001) 4734-4739.
Malysz, John et al. "In vitro pharmacological characterization of a novel selective α7 neuronal nicotinic acetylcholine receptor agonist ABT-107," *J Pharmacol Exp Ther*, 334:3 (2010) 863-874.
Mancuso, Cesare et al. "Pharmacologists and Alzheimer disease therapy: to boldly go where no scientist has gone before," *Expert Opin Invest Drugs*, 20:9 (2011) 1243-1261.
Mangialasche, Francesca et al. "Alzheimer's Disease: clinical trials and drug development," *Lancet Neurology*, 9 (2010) 702-716.
Maurer et al., "The relationship between the exposure and non-specific binding of thirty-three central nervous system drugs in mice," *Drug Metabolism and Disposition*, 33 (2005) 175-181.
Mazarov, Anatoly A. et al. "Discovery and development of α7 nicotinic acetylcholine receptor modulators," *J Med Chem*, 54 (2011) 7943-7961.
McGehee, D.S. et al., "Physiological Diversity of Nicotinic Acetylcholine Receptors Expressed by Vertebrate Neurons," *Annu. Rev. Physiol.*, vol. 57 (1995) 521-546.
Meyer, Edwin M. et al. "3-[2,4-Dimethoxybenzylidene]anabaseine (DMXB) selectively activates rat α7 receptors and improves memory-related behaviors in a mecamylamine-sensitive manner," *Brain Research*, 768 (1997) 49-56.
Meyer, Edwin M. et al. "Analysis of 3-(4-hydroxy, 2-methoxybenzylidene)anabaseine selectivity and activity at human and rat α7 nicotinic receptors," *J Pharmacol Exp Ther*, 287 (1998) 918-925.
Meyer, Edwin M. et al. "Neuroprotective and memory-related actions of novel α7 nicotinic agents with different mixed agonist/antagonist properties," *J Pharmacol Exp Ther*, 284:3 (1998) 1026-1032.
Mimica, Ninoslav et al. "Current treatment options for people with Alzheimer's disease in Croatia," *Chemico-Biological Interactions*, 187 (2010) 409-410.
Mohs, Richard C. et al., "Development of Cognitive Instruments for Use in Clinical Trials of Antidementia Drugs: Additions to the Alzheimer's Disease Assessment Scale That Broaden Its Scope," *Alzheimer's Disease and Associated Disorders*, 11:S2 (1997) S13-S21.
Naatanen et al., "Generators of electrical and magnetic mismatch responses in humans," *Brain Topogr*, 7 (1995) 315-320.
Ng, Herman J. et al. "Nootropic α7 nicotinic receptor allosteric modulator derived from $GABA_A$ receptor modulators," *Proc Natl Acad Sci*, 104:19 (2007) 8059-8064.
Nishizaki, Tomoyuki et al. "Presynaptic nicotinic acetylcholine receptors as a functional target of Nefiracetam in inducing a long-lasting facilitation of hippocampal neurotransmission," *Alzheimer Disease Assoc Disord*, 14:Suppl 1 (2000) s82-s94.
Nishizaki, Tomoyuki et al. "The anti-dementia drug nefiracetam facilitates hippcampal synaptic transmission by functionally targeting presynaptic nicotinic ACh receptors," *Mol Brain Res*, 80 (2000) 53-62.
Nordberg et al., "Cholinesterase Inhibitors in the Treatment of Alzheimer's Disease," *Drug Safety*, 19:6 (Dec. 1998) 465-480.
Nordberg, Agneta "Neuroprotection in Alzheimer's Disease—New strategies for treatment," *Neurotoxicity Research*, 2 (2000) 157-165.
Numata, Atsushi, "1-Azabicycloalkane Compound and Pharmaceutical Use Thereof," *Patent Abstracts of Japan*, vol. 5 (May 3, 2002) and JP 2002 030084 (Jan. 29, 2002).

O'Neill, M.J. et al. "The role of neuronal nicotinic acetylcholine receptors in acute and chronic neurodegeneration," *Curr Drug Targets—CNS & Neural Disord*, 1 (2002) 399-411.
Olincy et al., "Proof-of-concept trial of an alpha7 nicotinic agonist in schizophrenia," *Arch Gen Psychiatry*, 63 (2006) 630-638.
Papke, Roger L. et al. "Electrophysiological perspectives an the therapeutic use of nicotinic acetylcholine receptor partial agonists," *J Pharmacol Exp Ther*, 337:2 (2011) 367-379.
Papke, Roger L. et al. "α7 Receptor-selective agonists and modes of α7 receptor activation," *Euro J Pharmacol*, 393 (2000) 179-195.
Pichat, Philippe et al. "SSR180711, a novel selective α7 nicotinic receptor partial agonist: (II) Efficacy in experimental models predictive of activity against cognitive symptoms of schizophrenia," *Neuropsychopharmacology*, 32 (2007) 17-34.
Plath, Niels et al. "Can small molecules provide truly effective enhancement of cognition? Current achievements and future directions," *Expert Opin Invest Drugs*, 20:6 (2011) 795-811.
Potter et al., "Review of clinical correlates of P50 sensory gating abnormalities in patients with schizophrenia," *Schizophr Bull*, 32 (2006) 692-700.
Prickaerts et al., "Dissociable effects of acetylcholinesterase inhibitors and phosphodiesterase type 5 inhibitors on object recognition memory: acquisition versus consolidation," *Psychopharmacology*, 177 (2005) 381-390.
Prickaerts et al., "Phosphodiesterase type 5 inhibition improves early memory consolidation of object information," *Neurochem Int*, 45 (2004) 915-928.
Prickaerts, J. et al., "Possible role of nitric oxide-cyclic GMP pathway in object recognition memory: Effects of 7-nitroindazole and zaprinast", *European Journal of Pharmacology*, 337 (1997) 125-136.
Prickaerts, Jos et al. "EVP-6124, a novel and selective α7 nicotinic acetylcholine receptor partial agonist, improves memory performance by potentiating the acetylcholine response of α7 nicotinic acetylcholine receptors," *Neuropharmacology*, 62 (2012) 1099-1110.
Rezvani, A.H. et al., "Effect of R3487/MEM3454, a novel nicotinic alpha7 receptor partial agonist and 5-HT3 antagonist on sustained attention in rats," *Progress in Neuro-Psychopharmacology & Biological Psychiatry*, 33:2 (Mar. 17, 2009) 269-275.
Rezvani, Amir H. et al, "Cognitive effects of nicotine," *Biological Psychiatry*, 49 (2001) 258-267.
Rosen, Wilma G. et al., "A New Rating Scale for Alzheimer's Disease," *Am J Psychiatry*, 141:11 (Nov. 1984) 1356-1364.
Rosse, Richard B. et al. "Adjuvant Galantamine administration improves negative symptoms in a patient with treatment-refractory schizophrenia," *Clin Neuropharmacol*, 25 (2002) 272-275.
Sabbagh et al., "Drug development for Alzheimer's disease: Where are we now and where are we headed?" *American Journal of Geriatric Pharmacotherapy, Excerpta Medica*, 7:3 (Jun. 1, 2009) 167-185.
Sandman et al., "The auditory event-related potential is a stable and reliable measure in elderly subjects over a 3 year period," *Clin Neurophysiol*, 111 (2000) 1427-1437.
Schall et al., "Functional neuroanatomy of auditory mismatch processing: an event-related fMRI study of duration deviant oddballs," *Neuroimage*, 20 (2003) 729-736.
Seguela, P. et al., "Molecular Cloning, Functional Properties, and Distribution of Rat Brain α7: A Nicotinic Cation Channel Highly Permeable to Calcium," *Journal of Neuroscience*, 13:2 (Feb. 1993) 596-604.
Silva, Alcino J. et al. "Molecular and cellular mechanisms of cognitive function: Implications for psychiatric disorders," *Biological Psychiatry*, 47 (2000) 200-209.
Smulders, Chantal J.G.M. et al. "Cholinergic drugs potentiate human nicotinic α4β2 acetylcholine receptors by a competitive mechanism," *Euro J Pharmacol*, 509 (2005) 97-108.
Stahl, Stephen M., Ph.D. "Paying Attention to Your Acetylcholine, Part 2: The function of nicotinic receptors," *J Clin Psychiatry*, 61:9 (Sep. 2000) 628-629.
Strobel, Gabrielle "12th International Conference on Alzheimer's Disease (ICAD), Vienna, Austria," *J Alzheimers Disease*, 18 (2009) 973-990.

(56) References Cited

OTHER PUBLICATIONS

Sydserff, Simon et al. "Selective α7 nicotinic receptor activation by AZD0328 enhances cortical dopamine release and improves learning and attentional processes," *Biochem Pharmacol*, 78 (2009) 880-888.

Taly, Antoine et al. "Nicotinic receptors: Allosteric transitions and therapeutic targets in the nervous system," *Nature Rev: Drug Discovery*, 8 (Sep. 2009) 733-750.

Tcheremissine, Oleg V. et al. "Targeting cognitive deficits in schizophrenia: A review of the development of a new class of medicines from the perspective of community mental health researchers," *Expert Opin Invest Drugs*, 21:1 (2012) 7-14.

Thomsen, Morten S. et al. "Cognitive improvement by activation of α7 nicotinic acetylcholine receptors: From animal models to human pathophysiology," *Curr Pharmaceut Design*, 16 (2010) 323-343.

Townsend, Matthew "When will Alzheimer's Disease be cured? A pharmaceutical perspective," *J Alzheimers Disease*, 24 (2011) 43-52.

Trainor et al., "The importance of plasma protein binding in drug discovery," *Expert Opinion in Drug Discovery*, 20 (2007) 51-64.

Turetsky et al., "Neurophysiological endophenotypes of schizophrenia: the viability of selected candidate measures," *Schizophr Bull*, 33 (2007) 69-94.

Umbricht et al., "Mismatch negativity in schizophrenia: a meta-analysis," *Schizophr Res*, 76 (2005) 1-23.

Upadhyaya, Prerna et al. "Therapy of Alzheimer's Disease: An update," *African J Pharm Pharmacol*, 4:6 (Jun. 2010) 408-421.

Uteshev, V. V. et al. "Kinetic analysis of α7 nAChR fast desensitization in acutely dissociated neurons: Implications for therapeutics," *Soc Neuroscience*, Program No. 716.20 (Nov. 8, 2000). (Abstract only).

van Kampen, Maria et al. "AR-R17779 improves social ecognition in rats by activation of nicotinic α7 receptors," *Psychopharmacology*, 172 (2004) 375-383.

Vaucher, E. et al. "Object recognition memory and cholinergic parameters in mice expressing human presenilin 1 transgenes," *Experimental Neurology*, 175 (2002) 398-406.

Vazquez, Raymond W. et al. "Identification of a new amino acid residue capable of modulating agonist efficacy at the homomeric nicotinic acetylcholine receptor, α7," *Molecular Pharmacol*, 55 (1999) 1-7.

Vippagunta, S.R. et al., "Crystalline Solids," *Advanced Drug Delivery Reviews*, 48 (2001) 3-26.

Wallace, T. L. et al., "R3487/MEM 3454, a novel nicotinic alpha 7 receptor partial agonist, improves attention and working memory performance in cynomolgus macaques," *Biochemical Pharmacology*, 78:7(Oct. 1, 2009) 912.

Wallace, Tanya L. et al. "Drug targets for cognitive enhancement in neuropsychiatric disorders," *Pharmacol Biochem Behavior*, 99 (2011) 130-145.

Wallace, Tanya L. et al. "RG3487, a novel nicotinic α7 receptor partial agonist, improves cognition and sensorimotor gating in rodents," *J Pharmacol Exp Ther*, 336:1 (2011)242-253.

Wallace, Tanya L. et al. "Targeting the nicotinic alpha7 acetylcholine receptor to enhance cognition in disease," *Biochem Pharmacol*, 82 (2011) 891-903.

Werber et al., "Evaluation of cholinergic treatment in demented patients by P300 evoked related potentials," *Neurol Neurochir Pol*, 35:Suppl 3 (2001) 37-43.

Werkheiser, J. L. et al, "Ultra-low exposure to alpha-7 nicotinic acetylcholine receptor partial agonists elicits an improvement in cognition that corresponds with an increase in alpha-7 receptor expression in rodents: Implications for low dose clinical efficacy," *Neuroscience*, 186 (2011) 76-87.

Wevers, A. et al. "Expression of nicotinic acetylcholine receptor subunits in the cerebral cortex in Alzheimer's disease: histotopographical correlation with amyloid plaques and hyperphosphorylated-tau protein," *Euro J Neuroscience*, 11 (19S9)2551-2565.

Whitehead et al., "Donepezil for the Symptomatic Treatment of Patients with Mild to Moderate Alzheimer's Disease: a Meta-Analysis of Individual Patient Data from Randomised Controlled Trials," *Int J Geriatr Psychiatry*, 19 (2004) 624-633.

Wirowski, D. et al. "Expression of α4 and α7 nicotinic receptor subunits in the temporal cortex in dementia with lewy bodies and controls," *Soc Neuroscience*, Program No. 195.18 (Nov. 11, 2001). (Abstract only).

Wishka, Donn G. et al., "Discovery of N-[(3R)-1-azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure—Activity Relationship," *Journal of Medicinal Chemistry*, 49:14 (Jul. 2006) 4425-4436.

Woodruff-Pak, Diana "Preclinical experiments on cognition enhancement in Alzheimer's Disease: Drugs affecting nicotinic acetylcholine receptors," *Drug Dev Research*, 56 (2002) 335-346.

Anonymous: "*Safety and Cognitive Function Study of EVP-6124 in Patients with Mild to Moderate Alzheimer's Disease*", Feb. 19, 2010 (Feb. 19, 2010), Retrieved from the Internet: URL:https://clinicaltrials.gov/ct2/show/NCT01073228? term=evp-6124&rank=15 [retrieved on Sep. 2, 2015].

European Supplementary Search Report, dated Sep. 18, 2015, in corresponding European patent application EP 13787744.5-1464 / 2846796.

* cited by examiner

METHODS OF MAINTAINING, TREATING OR IMPROVING COGNITIVE FUNCTION

RELATED APPLICATIONS

This application is the National Phase application of International Application No. PCT/US2013/039692, filed May 6, 2013, which designates the United States and was published in English, and which further claims the benefit of priority from both U.S. Provisional Application No. 61/644,113, filed May 8, 2012, and U.S. Provisional Application No. 61/670,087, filed Jul. 20, 2012. The foregoing related applications, in their entirety, are incorporated herein by reference.

U.S. Pat. No. 8,076,355, U.S. patent application Ser. No. 13/129,782, and International Patent Application No. PCT/US2011/036844 (which designates the U.S.) are each, in their entirety, further incorporated herein by reference.

FIELD OF THE INVENTION

The present invention relates to a method of maintaining, treating and/or improving cognitive function. In particular, the method relates to administering (R)-7-chloro-N-(quinuclidin-3-yl)benzo[b]thiophene-2-carboxamide, or a pharmaceutically acceptable salt thereof, to a patient in need thereof, for example a patient diagnosed with having Alzheimer's disease, that may derive a benefit therefrom.

BACKGROUND

For many, Alzheimer's disease is the number one medical issue facing our aging society. It is typically thought to be a late onset neurodegenerative disease that impairs memory and cognitive performance. Symptoms frequently include decreased functional capacity and negative psychological attributes (e.g., depression, anxiety) in association with the memory and cognition deficits.

The prevalence of dementia in North America is approximately 6 to 10% of the population, with Alzheimer's disease accounting for a substantial portion of these cases. This illness represents a steadily growing medical and social problem of our aging societies around the World. Some believe the main pathological features may relate to intraneuronal neurofibrillary tangles, formation of amyloid beta plaques and/or neurodegeneration of mainly cholinergic and, in later stages, also serotonergic, noradrenergic, and other neurons, resulting in deficiencies of acetylcholine and other neurotransmitters. Some theories suggest that the gradual development of an acetylcholine signaling deficiency may be responsible for the early clinical manifestations of Alzheimer's disease. Consequently, some believe that compounds that improve cholinergic functioning, such as acetylcholine esterase inhibitors may ameliorate the cognitive deficits in patients with Alzheimer's disease. The most widely used acetylcholine esterase inhibitor is donepezil hydrochloride (Aricept®).

Acetylcholine esterase inhibitor medications are designed to increase acetylcholine levels, a neurotransmitter that is severely reduced in the brain of patients with Alzheimer's disease. Rogers reports that treatment with an acetylcholine esterase inhibitor typically results in an increase of approximately 2.5-3.1 points on the cognitive subscale of the Alzheimer's disease assessment scale (ADAS-Cog) from baseline over placebo (Rogers, 1998). Cummings reports that improvements in cognition modestly exceed the threshold considered to be clinically relevant and typically last for 6 months (Cummings, 2001). Therefore, more efficacious drugs are urgently needed to provide treatment for cognitive impairments such as for patients with Alzheimer's disease.

BRIEF SUMMARY OF THE INVENTION

One embodiment of the invention relates to a method comprising administering to a patient in need thereof, for an extended period, an effective dose of (R)-7-chloro-N-(quinuclidin-3-yl)benzo[b]thiophene-2-carboxamide, or a pharmaceutically acceptable salt thereof.

Another embodiment of the invention provides a method of maintaining, treating, curing and/or improving at least one cognitive function in a patient in need thereof, comprising: administering to the patient, for an extended period, an effective dose of (R)-7-chloro-N-(quinuclidin-3-yl)benzo[b]thiophene-2-carboxamide, or a pharmaceutically acceptable salt thereof.

Another embodiment of the invention provides a method of maintaining, treating, curing and/or improving at least one cognitive function in a patient in need thereof, comprising: administering to the patient, for an extended period, a daily dose (R)-7-chloro-N-(quinuclidin-3-yl)benzo[b]thiophene-2-carboxamide, or a pharmaceutically acceptable salt thereof.

Another embodiment of the invention provides a method of treating a patient in need thereof, comprising: administering to the patient diagnosed as having a cognitive impairment a daily dose of a pharmaceutical composition comprising (R)-7-chloro-N-(quinuclidin-3-yl)benzo[b]thiophene-2-carboxamide, or a pharmaceutically acceptable salt thereof, for an extended period.

Another embodiment of the invention provides a method of treating a patient in need thereof, comprising: administering to the patient, for an extended period, a daily dose of (R)-7-chloro-N-(quinuclidin-3-yl)benzo[b]thiophene-2-carboxamide, or a pharmaceutically acceptable salt thereof.

Another embodiment of the invention provides a method of treating a patient in need thereof, comprising: administering to the patient, for an extended period, a daily dose of (R)-7-chloro-N-(quinuclidin-3-yl)benzo[b]thiophene-2-carboxamide, or a pharmaceutically acceptable salt thereof, in either a fasted or fed mode.

Another embodiment of the invention provides a method of treating a patient in need thereof, comprising: administering to the patient, for example a patient diagnosed with having a cognitive impairment, Limited Cognitive Impairment, Mild Cognitive Impairment, and/or Alzheimer's disease, (R)-7-chloro-N-(quinuclidin-3-yl)benzo[b]thiophene-2-carboxamide, or a pharmaceutically acceptable salt thereof, for an extended period, such that the patient may derive a benefit therefrom.

Another embodiment of the invention provides a method of treating one or more symptoms associated with a cognitive impairment, comprising administering to a patient, for an extended period, a daily dose of (R)-7-chloro-N-(quinuclidin-3-yl)benzo[b]thiophene-2-carboxamide, or a pharmaceutically acceptable salt thereof, wherein the patient suffers from, or has been diagnosed as having, a cognitive impairment.

Another embodiment of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides said patient at least one of the following: (i) treats, or prevents the deterioration of, one or more symptoms associated with the cognitive impairment; (ii) treats the cognitive impairment; (iii) improves cognition in said cognitively impaired patient; (iv) improves one or more behavioral symptoms associated with the cognitive impairment; (v) provides a pro-cognitive effect; or (vi) provides a pro-cognitive effect, exclusive of attention, in at least one of the following: visual motor, learning, delayed memory, or executive function.

Another embodiment of the invention provides a method of minimizing progression of one or more symptoms associated with a cognitive impairment in a patient, comprising administering to the patient, for an extended period, a daily dose of (R)-7-chloro-N-(quinuclidin-3-yl)benzo[b]thiophene-2-carboxamide, or a pharmaceutically acceptable salt thereof.

Another embodiment of the invention provides a method of treating a cognitive impairment, comprising administering to a patient, for an extended period, a daily dose of (R)-7-chloro-N-(quinuclidin-3-yl)benzo[b]thiophene-2-carboxamide, or a pharmaceutically acceptable salt thereof, wherein the patient suffers from one or more symptoms associated with the cognitive impairment.

Another embodiment of the invention provides a method of minimizing progression of a cognitive impairment in a patient, comprising administering to the patient, for an extended period, a daily dose of (R)-7-chloro-N-(quinuclidin-3-yl)benzo[b]thiophene-2-carboxamide, or a pharmaceutically acceptable salt thereof.

Another embodiment of the invention provides a method of improving cognition in a patient having a cognitive impairment, comprising administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of reducing the rate of deterioration of one or more symptoms in a patient suffering from, or diagnosed as having, a cognitive impairment, for example mild Alzheimer's disease, moderate Alzheimer's disease, severe Alzheimer's disease, or mild-to-moderate Alzheimer's disease, comprising: administering to the patient, for an extended period, an initial daily dose of a pharmaceutical composition comprising an amount of between 0.1 mg and 4.5 mg of (R)-7-chloro-N-(quinuclidin-3-yl)benzo[b]thiophene-2-carboxamide, or a pharmaceutically acceptable salt thereof.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a positive effect on cognition or a positive effect on clinical function in said cognitively impaired patient.

Another embodiment of the invention provides a method of treating a patient previously treated, or currently being treated, with an AChEI, that is suffering from, or has been diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves one or more symptoms associated with the cognitive impairment in the previously, or currently, AChEI treated patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a positive effect on cognition or a positive effect on clinical function in said cognitively impaired patient, and wherein said patient has been previously treated or is currently being treated with an AChEI.

Another embodiment of the invention provides a method of treating a patient suffering from, or diagnosed as having, a cognitive impairment, for example mild Alzheimer's disease, moderate Alzheimer's disease, severe Alzheimer's disease, or mild-to-moderate Alzheimer's disease, comprising: administering for an extended period, for example for at least 6, 12, or 18 weeks, an initial daily dose of a pharmaceutical composition comprising an amount of at least 1.0 mg or more to no more than 4.5 mg of (R)-7-chloro-N-(quinuclidin-3-yl)benzo[b]thiophene-2-carboxamide, or a pharmaceutically acceptable salt thereof.

Another embodiment of the invention provides a method of treating a patient suffering from, or diagnosed as having, a cognitive impairment, for example having a score of ≥14 to ≤24 on a MMSE test or a score of ≥2 on a CDR-SB test, comprising: administering for an extended period, for example for at least 6, 12, 18, or 23 weeks, an initial daily dose of a pharmaceutical composition comprising an amount at least 1.0 mg or more to no more than 4.5 mg of (R)-7-chloro-N-(quinuclidin-3-yl)benzo[b]thiophene-2-carboxamide, or a pharmaceutically acceptable salt thereof.

Another embodiment of the invention provides a method of slowing or preventing deterioration of one or more symptoms associated with a cognitive impairment, for example mild Alzheimer's disease, moderate Alzheimer's disease, severe Alzheimer's disease, or mild-to-moderate Alzheimer's disease, in a patient suffering from, or diagnosed as having, the cognitive impairment, comprising: administering to the patient, for an extended period, for example for at least 6, 12, or 18 weeks, an initial daily dose of a pharmaceutical composition comprising an amount of at least 1.0 mg or more to no more than 4.5 mg of (R)-7-chloro-N-(quinuclidin-3-yl)benzo[b]thiophene-2-carboxamide, or a pharmaceutically acceptable salt thereof.

Another embodiment of the invention provides a method of treating a patient in need thereof, comprising: i) administering to the patient, for an extended period, an initial daily dose of a pharmaceutical composition comprising (R)-7-chloro-N-(quinuclidin-3-yl)benzo[b]thiophene-2-carboxamide, or a pharmaceutically acceptable salt thereof; and ii) if well tolerated over at least a 12-week period, increasing the daily dose to greater than 2.0 mg but not greater than 4.5 mg, 4.3 mg, or 4.0 mg, of (R)-7-chloro-N-(quinuclidin-3-yl)benzo[b]thiophene-2-carboxamide, or a pharmaceutically acceptable salt thereof.

Another embodiment of the invention provides a method of treating a patient suffering from, or diagnosed as having a cognitive impairment, such as mild-to-moderate Alzheimer's disease, comprising: i) administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof; and ii) adjusting the amount of (R)-7-chloro-N-(quinuclidin-3-yl)benzo[b]thiophene-2-carboxamide, or a pharmaceutically acceptable salt thereof, that is administered to the patient according to at least one of the following: (a) to said patient's responsiveness to the treatment, (b) to the rate of progression of the cognitive impairment in said patient, or (c) to the rate of progression of one or more symptoms associated with the cognitive impairment in said patient.

Another embodiment of the invention provides a method of treating a patient having a sub-normal score on at least one cognitive assessment test, for example an MMSE less than 30, such as 29 or less, comprising: administering to the patient, for an extended period of time, an initial daily dose of a pharmaceutical composition comprising between 0.1 mg and 4.5 mg of (R)-7-chloro-N-(quinuclidin-3-yl)benzo[b]thiophene-2-carboxamide, or a pharmaceutically acceptable salt thereof.

Another embodiment of the invention provides a method of treating a patient in need thereof, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof, wherein the patient suffers from a cognitive impairment, for example mild Alzheimer's disease, moderate Alzheimer's disease, severe Alzheimer's disease, or mild-to-moderate Alzheimer's disease, or has been diagnosed with having the cognitive impairment by having scored one or more of the following: a value sub-normal value on one or more of the following cognitive assessment test: ADAS-Cog-13, ADAS-Cog-11, COWAT, CFT, or CDR-SB.

Another embodiment of the invention provides a method of treating a patient having a score of between ≥14 and ≤24 on a MMSE test, comprising: administering to the patient, for an extended period of time, an initial daily dose of a pharmaceutical composition comprising 1.0 mg, 2.0 mg, or 3.0 mg, of (R)-7-chloro-N-(quinuclidin-3-yl)benzo[b]thiophene-2-carboxamide, or a pharmaceutically acceptable salt thereof.

Another embodiment of the invention provides a method of treating a patient having a score of ≥14 to ≤24 on a MMSE test or a score of ≥2 on a CDR-SB test, or both, comprising: administering to the patient, for an extended period of time, an initial daily dose of a pharmaceutical composition comprising 1.0 mg, 2.0 mg, or 3.0 mg of (R)-7-chloro-N-(quinuclidin-3-yl)benzo[b]thiophene-2-carboxamide, or a pharmaceutically acceptable salt thereof.

Another embodiment of the invention provides a method of treating a patient diagnosed as having probable Alzheimer's disease, for example probable mild Alzheimer's disease, probable moderate Alzheimer's disease, probable severe Alzheimer's disease, or probable mild-to-moderate Alzheimer's disease, comprising: administering to the patient, for an extended period, an initial daily dose of a pharmaceutical composition comprising 1.0 mg, 2.0 mg, 3.7 mg, or 4.0 mg, of (R)-7-chloro-N-(quinuclidin-3-yl)benzo[b]thiophene-2-carboxamide, or a pharmaceutically acceptable salt thereof.

Another embodiment of the invention provides a method of improving cognition in a patient diagnosed as having probable Alzheimer's disease, for example probable mild Alzheimer's disease, probable moderate Alzheimer's disease, probable severe Alzheimer's disease, or probable mild-to-moderate Alzheimer's disease, comprising: administering to the patient, for an extended period, an initial daily dose of a pharmaceutical composition comprising 1.0 mg, 2.0 mg, 3.7 mg, or 4.0 mg, of (R)-7-chloro-N-(quinuclidin-3-yl)benzo[b]thiophene-2-carboxamide, or a pharmaceutically acceptable salt thereof.

Another embodiment of the invention provides a method of improving cognition in a patient diagnosed as having probable mild-to-moderate Alzheimer's disease, comprising: administering to the patient, for an extended period, for example at least 6, 12, 18, or 23 weeks, an initial daily dose of a pharmaceutical composition comprising between 0.7 mg and 3.5 mg of (R)-7-chloro-N-(quinuclidin-3-yl)benzo[b]thiophene-2-carboxamide, or a pharmaceutically acceptable salt thereof.

Another embodiment of the invention provides a method of improving or substantially improving one or more symptoms in a mild-to-moderate Alzheimer's patient, comprising: administering to the patient, for an extended period, a daily dose of (R)-7-chloro-N-(quinuclidin-3-yl)benzo[b]thiophene-2-carboxamide, or a pharmaceutically acceptable salt thereof.

Another embodiment of the invention provides a method of slowing the rate of deterioration of at least one symptom in a mild-to-moderate Alzheimer's patient, comprising: administering to the patient, for an extended period, the pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating one or more symptoms associated with Alzheimer's disease in a patient suffering from, or diagnosed as having, mild-to-moderate Alzheimer's disease, comprising: administering to the patient, for an extended period, a daily dose of a pharmaceutical composition comprising greater than 0.1 mg and no more than 4.5 mg of (R)-7-chloro-N-(quinuclidin-3-yl)benzo[b]thiophene-2-carboxamide, or a pharmaceutically acceptable salt thereof.

Another embodiment of the invention provides a method of treating one or more symptoms associated with Alzheimer's disease, for example mild Alzheimer's disease, moderate Alzheimer's disease, severe Alzheimer's disease, or mild-to-moderate Alzheimer's disease, in a patient suffering therefrom, comprising: administering to the patient, for at least 12 weeks, an initial daily dose of a pharmaceutical composition comprising 1.0 mg, 2.0 mg, 3.0 mg, 3.7 mg, or 4.3 mg, of (R)-7-chloro-N-(quinuclidin-3-yl)benzo[b]thiophene-2-carboxamide, or a pharmaceutically acceptable salt thereof.

Another embodiment of the invention provides a method of treating one or more symptoms associated with Alzheimer's disease, for example prodromal state of Alzheimer's disease or mild-to-moderate Alzheimer's disease, in a patient suffering therefrom, comprising: administering to the patient, for at least 12 weeks, an initial daily dose of a pharmaceutical composition comprising 1.0 mg, 2.0 mg, 3.0 mg, 3.7 mg, or 4.3 mg, of (R)-7-chloro-N-(quinuclidin-3-yl)benzo[b]thiophene-2-carboxamide, or a pharmaceutically acceptable salt thereof.

Another embodiment of the invention provides a method of minimizing or preventing progression of one or more symptoms associated with Alzheimer's disease in a patient suffering from mild-to-moderate Alzheimer's disease, comprising: administering to the patient, for an extended period, an initial daily dose of a pharmaceutical composition comprising between 0.1 mg and 4.5 mg of (R)-7-chloro-N-(quinuclidin-3-yl)benzo[b]thiophene-2-carboxamide, or a pharmaceutically acceptable salt thereof.

Another embodiment of the invention provides a method of improving cognition in a patient suffering from Alzheimer's disease or dementia of the Alzheimer's-type, for example mild-to-moderate dementia of the Alzheimer's-type, comprising administering to the patient, for an extended period, an initial daily dose of a pharmaceutical composition comprising at least 1.0 mg, 2.0 mg, 3.0 mg, or 4.0 mg, but no more than 4.5 mg of (R)-7-chloro-N-(quinuclidin-3-yl)benzo[b]thiophene-2-carboxamide, or a pharmaceutically acceptable salt thereof.

Another embodiment of the invention provides a method of improving cognition in a patient suffering from mild-to-moderate Alzheimer's disease, comprising: administering to the patient, for an extended period, for example at least 6, 12, or 18 weeks, an initial daily dose of a pharmaceutical composition comprising 0.3 mg, 1.0 mg, or 2.0 mg, of (R)-7-chloro-N-(quinuclidin-3-yl)benzo[b]thiophene-2-carboxamide, or a pharmaceutically acceptable salt thereof.

Another embodiment of the invention provides a method of treating progression of Alzheimer's disease in a patient suffering from mild-to-moderate Alzheimer's disease, comprising: administering, for an extended period, a daily dose of a pharmaceutical composition comprising an amount between 0.1 and 4.5 mg of (R)-7-chloro-N-(quinuclidin-3-yl)benzo[b]thiophene-2-carboxamide, or a pharmaceutically acceptable salt thereof, to the mild-to-moderate Alzheimer's patient.

A further embodiment provides a method of minimizing or substantially halting the rate of progression of Alzheimer's disease in a patient suffering from mild-to-moderate Alzheimer's disease, comprising: administering to the patient, for an extended period, an initial daily dose of a pharmaceutical composition comprising 1.0 mg, 2.0 mg, 3.7 mg, or 4.0 mg, of (R)-7-chloro-N-(quinuclidin-3-yl)benzo[b]thiophene-2-carboxamide, or a pharmaceutically acceptable salt thereof.

Another embodiment of the invention provides a method of substantially stopping or reversing progression of Alzheimer's disease, for example mild Alzheimer's disease, moderate Alzheimer's disease, severe Alzheimer's disease, or mild-to-moderate Alzheimer's disease, in a patient suffering therefrom, comprising: administering to the patient, for an extended period, an initial daily dose of a pharmaceutical composition comprising 2.0 mg, for example 2.0 mg, 3.0 mg, 3.5 mg, or no more than 4.5 mg, of (R)-7-chloro-N-(quinuclidin-3-yl)benzo[b]thiophene-2-carboxamide, or a pharmaceutically acceptable salt thereof.

Another embodiment of the invention provides a method of treating a patient diagnosed as having mild-to-moderate Alzheimer's disease, comprising: administering, to the patient, for an extended period, for example at least 6, 12, or 18 weeks, an initial daily dose of a pharmaceutical composition comprising greater than 0.1 mg but not more than 4.5 mg of (R)-7-chloro-N-(quinuclidin-3-yl)benzo[b]thiophene-2-carboxamide, or a pharmaceutically acceptable salt thereof.

Another embodiment of the invention provides a method of treating a patient diagnosed as having mild-to-moderate Alzheimer's disease, comprising: administering to the patient, for an extended period, an initial daily dose of a pharmaceutical composition comprising at least 1.0 mg, for example at least 1.0 mg, 1.5 mg, or 2.0 mg, but no more than 4.5 mg, of (R)-7-chloro-N-(quinuclidin-3-yl)benzo[b]thiophene-2-carboxamide, or a pharmaceutically acceptable salt thereof.

Another embodiment of the invention provides a method of treating a patient suffering from, or diagnosed as having, mild-to-moderate Alzheimer's disease, comprising: administering to the patient, for an extended period, for example for at least 6, 12, or 18 weeks, an initial daily dose of a pharmaceutical composition comprising an amount of between 0.1 mg and 4.5 mg of (R)-7-chloro-N-(quinuclidin-3-yl)benzo[b]thiophene-2-carboxamide, or a pharmaceutically acceptable salt thereof, wherein the method minimizes progression of one or more symptoms associated with mild-to-moderate Alzheimer's disease.

Another embodiment of the invention provides a method of treating either schizophrenia or Alzheimer's disease, for example mild Alzheimer's disease, moderate Alzheimer's disease, severe Alzheimer's disease, or mild-to-moderate Alzheimer's disease, comprising administering a daily dose of (R)-7-chloro-N-(quinuclidin-3-yl)benzo[b]thiophene-2-carboxamide, or a pharmaceutically acceptable salt thereof, in a larger amount for a patient with Alzheimer's disease than a patient with schizophrenia.

Another embodiment of the invention provides a method of improving cognition in a patient suffering from schizophrenia or Alzheimer's disease, for example mild Alzheimer's disease, moderate Alzheimer's disease, severe Alzheimer's disease, or mild-to-moderate Alzheimer's disease, comprising: i) administering to a patient with schizophrenia an initial daily dose of a pharmaceutical composition comprising at least 1.0 mg of (R)-7-chloro-N-(quinuclidin-3-yl)benzo[b]thiophene-2-carboxamide, or a pharmaceutically acceptable salt thereof, or ii) administering to a patient with Alzheimer's disease a daily dose of a pharmaceutical composition comprising an amount of (R)-7-chloro-N-(quinuclidin-3-yl)benzo[b]thiophene-2-carboxamide, or a pharmaceutically acceptable salt thereof, that is at least two times the initial daily dose, for at least 2.0 mg, of (R)-7-chloro-N-(quinuclidin-3-yl)benzo[b]thiophene-2-carboxamide, or a pharmaceutically acceptable salt thereof, administered to the patient with schizophrenia.

Another embodiment of the invention provides a method of improving cognitive function in a patient, comprising: administering to the patient, for an extended period, for example at least 6, 12, 18, or 23 weeks, an initial daily dose of a pharmaceutical composition comprising between 0.1 mg and 4.5 mg of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of treating a patient having a sub-normal score on at least one cognitive assessment test, for example MMSE, COWAT, ADAS-Cog-13, CFT, or CDR-SB, comprising: administering to the patient, for an extended period, an initial daily dose of a pharmaceutical composition comprising 2.0 mg of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of treating a patient having a score of between ≥14 and ≤24 on a MMSE test, comprising: administering to the patient, for an extended period of time, an initial daily dose of a pharmaceutical composition comprising 1.0 mg, 2.0 mg, or 3.0 mg, of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of reducing or preventing deterioration of one or more symptoms associated with a cognitive impairment, for example prodromal state of Alzheimer's disease, mild Alzheimer's disease, moderate Alzheimer's disease, severe Alzheimer's disease, mild-to-moderate Alzheimer's disease or probable Alzheimer's disease, in a patient suffering therefrom, comprising: administering to the patient, for an extended period, an initial daily dose of a pharmaceutical composition comprising 1.0 mg, 2.0 mg, or 3.0 mg, of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of improving cognition in a patient suffering from, and/or diagnosed as having, mild-to-moderate Alzheimer's disease, comprising: administering, for an extended period, an initial daily dose of a pharmaceutical composition comprising 1.0 mg, 2.0 mg, or 3.0 mg, of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of treating a patient suffering from, and/or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, for example at least 6, 12, or 18 weeks, an initial daily dose of a pharmaceutical composition comprising at least 2.0 mg, for example at least 2.0 mg but no more than 4.5 mg, of (R)-7-chloro-N-(quinuclidin-3-yl)benzo[b]thiophene-2-carboxamide, hydrochloride, monohydrate, for example (R)-7-chloro-N-(quinuclidin-3-yl)benzo[b]thiophene-2-carboxamide, hydrochloride, monohydrate, polymorph form I.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein said effective amount is administered in a daily dose.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the daily dose comprises between 1.0 mg and 4.5 mg of (R)-7-chloro-N-(quinuclidin-3-yl)benzo[b]thiophene-2-carboxamide, or a pharmaceutically acceptable salt thereof.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the daily dose comprises between 1.5 mg and 4.3 mg of (R)-7-chloro-N-(quinuclidin-3-yl)benzo[b]thiophene-2-carboxamide, or a pharmaceutically acceptable salt thereof.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the daily dose comprises between 1.8 mg and 3.2 mg of (R)-7-chloro-N-(quinuclidin-3-yl)benzo[b]thiophene-2-carboxamide, or a pharmaceutically acceptable salt thereof.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, for example for at least 6, 12, 18, 23, or 24 weeks.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate, polymorph form I.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the (R)-7-chloro-N-(quinuclidin-3-yl)benzo[b]thiophene-2-carboxamide, or a pharmaceutically acceptable salt thereof, is administered in the form of a pharmaceutical composition comprising at least one pharmaceutically acceptable carrier, excipient or diluent.

Another embodiment of the invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period, wherein the pharmaceutical composition is in the form of a tablet.

Another embodiment of the invention provides a method of treating a patient having Alzheimer's disease, comprising: administering, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating a patient having mild-to-moderate Alzheimer's disease, comprising: administering to the patient, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating a patient having mild-to-moderate Alzheimer's disease, comprising: administering to the patient, for an extended period, an initial daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating a patient having Alzheimer's disease, for example improving cognition of the patient having Alzheimer's disease, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof, wherein the treating includes treating a symptom associated with Alzheimer's disease.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof, wherein treating includes preventing progression of Alzheimer's disease.

Another embodiment of the invention provides a method of treating a patient diagnosed as having mild-to-moderate Alzheimer's disease, comprising: administering to the patient, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of treating a patient having Alzheimer's disease, comprising: administering to the patient, for an extended period, a daily dose of a pharmaceutical composition comprising between 0.3 mg and 4.5 mg of (R)-7-chloro-N-(quinuclidin-3-yl)benzo[b]thiophene-2-carboxamide, or a pharmaceutically acceptable salt thereof.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising 0.3 mg, 1.0 mg, 2.0 mg, or 3.0 mg, of (R)-7-chloro-N-(quinuclidin-3-yl)benzo[b]thiophene-2-carboxamide, or a pharmaceutically acceptable salt thereof.

Another embodiment of the invention provides a method of treating a patient having Alzheimer's disease, comprising: administering to the patient, for an extended period, a daily dose of a pharmaceutical composition comprising between 0.3 mg and 4.5 mg of (R)-7-chloro-N-(quinuclidin-3-yl)benzo[b]thiophene-2-carboxamide, hydrochloride, monohydrate.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising 0.3 mg, 1.0 mg, 2.0 mg, or 3.0 mg, of (R)-7-chloro-N-(quinuclidin-3-yl)benzo[b]thiophene-2-carboxamide, hydrochloride, monohydrate.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising between 90 wt. % and 110 wt. % of a designated 1.0 mg dosage, 2.0 mg dosage, or 3.0 mg dosage, of (R)-7-chloro-N-(quinuclidin-3-yl)benzo[b]thiophene-2-carboxamide, hydrochloride, monohydrate.

Another embodiment of the invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, for example for at least 6, 12, 18, 23, or 24 weeks, a daily dose of a pharmaceutical composition comprising between 90 wt. % and 110 wt. % of a designated 1.0 mg dosage, 2.0 mg dosage, or 3.0 mg dosage, of (R)-7-chloro-N-(quinuclidin-3-yl)benzo[b]thiophene-2-carboxamide, hydrochloride, monohydrate, polymorph form I.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising 1.0 mg (R)-7-chloro-N-(quinuclidin-3-yl)benzo[b]thiophene-2-carboxamide, hydrochloride, monohydrate.

Another embodiment of the invention provides a method of treating a patient having Alzheimer's disease, comprising: administering to the patient, for an extended period, for example for at least 6, 12, 18, 23, or 24 weeks, a daily dose of a pharmaceutical composition comprising 2.0 mg (R)-7-chloro-N-(quinuclidin-3-yl)benzo[b]thiophene-2-carboxamide, hydrochloride, monohydrate.

Another embodiment of the invention provides a method of treating a patient having Alzheimer's disease, comprising: administering to the patient, in either fasted or fed mode, for an extended period, a daily dose of a pharmaceutical composition comprising (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate.

Another embodiment of the invention provides a method of treating a patient having Alzheimer's disease, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate, wherein the pharmaceutical composition is in the form of a tablet.

Another embodiment of the invention provides a method of treating a patient having Alzheimer's disease, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate, wherein the treatment further comprises co-administering an acetylcholine esterase inhibitor.

Another embodiment of the invention provides a method of treating a patient having Alzheimer's disease and being administered an acetylcholine esterase inhibitor, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate, wherein the treatment comprises halting the administration of the acetylcholine esterase inhibitor prior to treating with (R)-7-chloro-N-(quinuclidin-3-yl)benzo[b]thiophene-2-carboxamide, or a pharmaceutically acceptable salt thereof.

Another embodiment of the invention provides a method of treating a patient suffering from, or diagnosed as having, a cognitive impairment, for example LCI, MCI, or dementia of the Alzheimer's-type, comprising: administering to the patient, for an extended period, for example for at least 6, 12, 18, 23, or 24 weeks, a daily dose of a pharmaceutical composition comprising an amount of 1.0 mg, 2.0 mg, or 3.0 mg, of (R)-7-chloro-N-(quinuclidin-3-yl)benzo[b]thiophene-2-carboxamide, hydrochloride, monohydrate, polymorph form I.

Another embodiment of the invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, for example for at least 6, 12, 18, 23, or 24 weeks, a daily dose of a pharmaceutical composition comprising an amount of 1.0 mg, 2.0 mg, or 3.0 mg, of (R)-7-chloro-N-(quinuclidin-3-yl)benzo[b]thiophene-2-carboxamide, hydrochloride, monohydrate, polymorph form I.

Another embodiment of the invention provides a method of treating a patient having a cognitive impairment, comprising: administering to the patient, for an extended period, for example for at least 6, 12, 18, 23, or 24 weeks, a daily dose of a pharmaceutical composition comprising (R)-7-chloro-N-(quinuclidin-3-yl)benzo[b]thiophene-2-carboxamide, or a pharmaceutically acceptable salt thereof.

Another embodiment of the invention provides a method of improving cognition in a patient having a cognitive impairment, for example LCI, MCI, Alzheimer's disease, or dementia of the Alzheimer's-type, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate, or (R)-7-chloro-N-(quinuclidin-3-yl)benzo[b]thiophene-2-carboxamide, hydrochloride, monohydrate, polymorph form I.

Another embodiment of the invention provides a method of treating a patient in need thereof, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I.

Another embodiment of the invention provides a method of treating a patient in need thereof, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient in need thereof, comprising: administering to the patient, in either fasted or fed mode, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient suffering from, or diagnosed as having, a cognitive impairment, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient having a sub-normal score on at least one cognitive assessment test, for example having a score of ≥14 to ≤24 on a MMSE test or a score of ≥2 on a CDR-SB test, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising:

administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient suffering from, or diagnosed as having, LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl) benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of treating a patient suffering from, or diagnosed as having, MCI, comprising: administering to the patient, for an extended period, a tablet composed of a pharmaceutical composition comprising a designated daily dose of between 0.1 mg and 4.5 mg of (R)-7-chloro-N-(quinuclidin-3-yl) benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of improving cognition or providing a procognitive effect in a patient suffering from, or diagnosed as having, a cognitive impairment, for example Alzheimer's disease, dementia of the Alzheimer's-type, MCI, or LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of improving cognition or providing a procognitive effect in a patient suffering from, or diagnosed as having, a cognitive impairment, for example Alzheimer's disease, dementia of the Alzheimer's-type, MCI, or LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form II, comprises between 80 and 115 wt. % of the designated daily dose.

Another embodiment of the invention provides a method of improving cognition or providing a procognitive effect in a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of improving cognition or providing a procognitive effect in a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

Another embodiment of the invention provides a method of improving or preventing the deterioration of one or more symptoms associated with a cognitive impairment, for example Alzheimer's disease, dementia of the Alzheimer's-type, MCI, or LCI, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, the cognitive impairment.

Another embodiment of the invention provides a method of improving or preventing the deterioration of one or more symptoms associated with Alzheimer's disease, for example mild Alzheimer's disease, moderate Alzheimer's disease, severe Alzheimer's disease, or mild-to-moderate Alzheimer's disease, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, Alzheimer's disease.

Another embodiment of the invention provides a method of improving or preventing the deterioration of one or more symptoms associated with dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, dementia of the Alzheimer's-type.

Another embodiment of the invention provides a method of treating a patient suffering from, or diagnosed as having, a cognitive impairment, for example Alzheimer's disease, dementia of the Alzheimer's-type, MCI, or LCI, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of the cognitive impairment in said patient.

Another embodiment of the invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of Alzheimer's disease in said patient.

Another embodiment of the invention provides a method of treating a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of the dementia of the Alzheimer's-type in said patient.

DETAILED DESCRIPTION OF THE INVENTION

Figure 1:
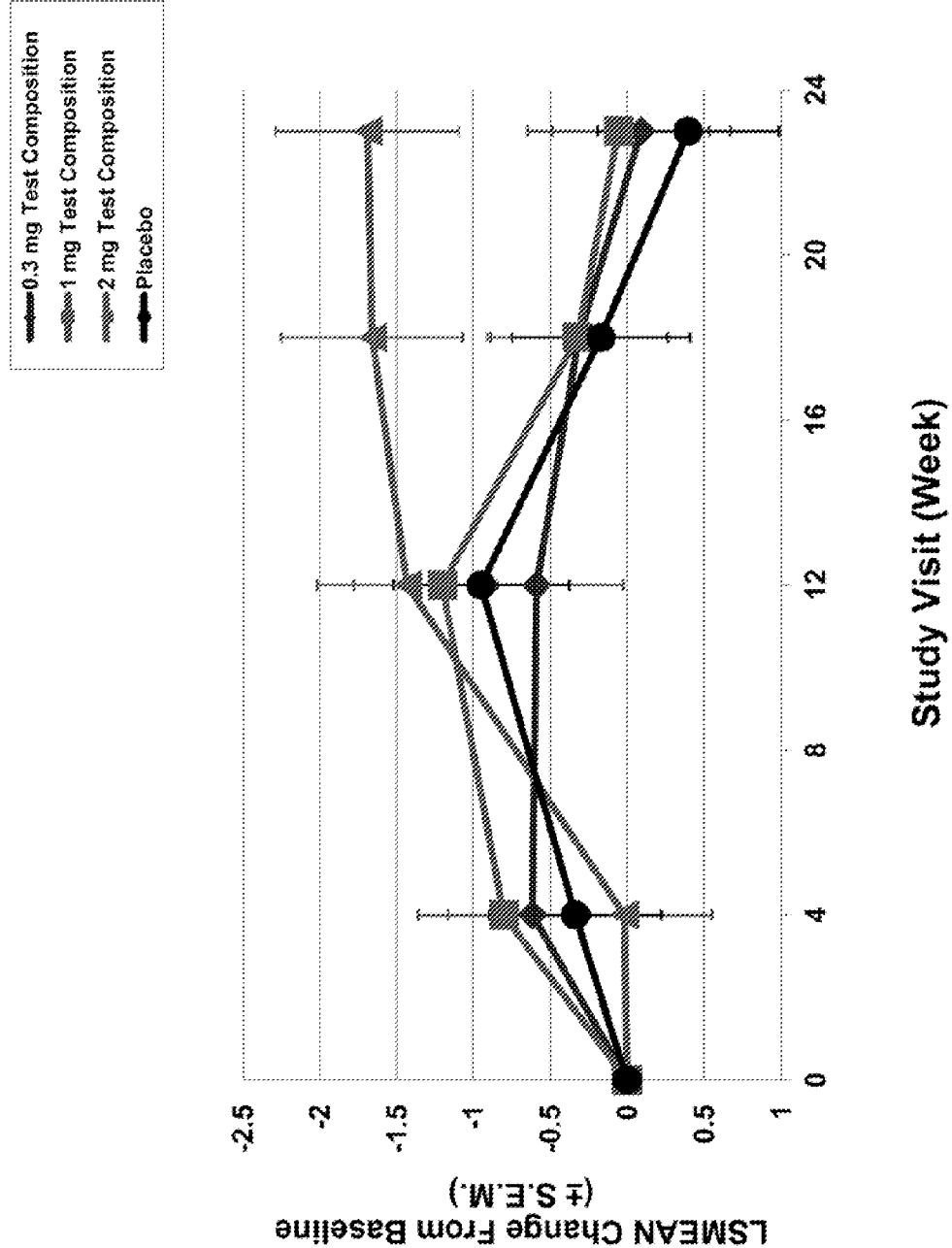
FIG. 1: is graph of the results from the clinical study of Example 1 for Alzheimer's Disease Assessment Scale Cog-13 (ADAS Cog-13).
Figure 2:
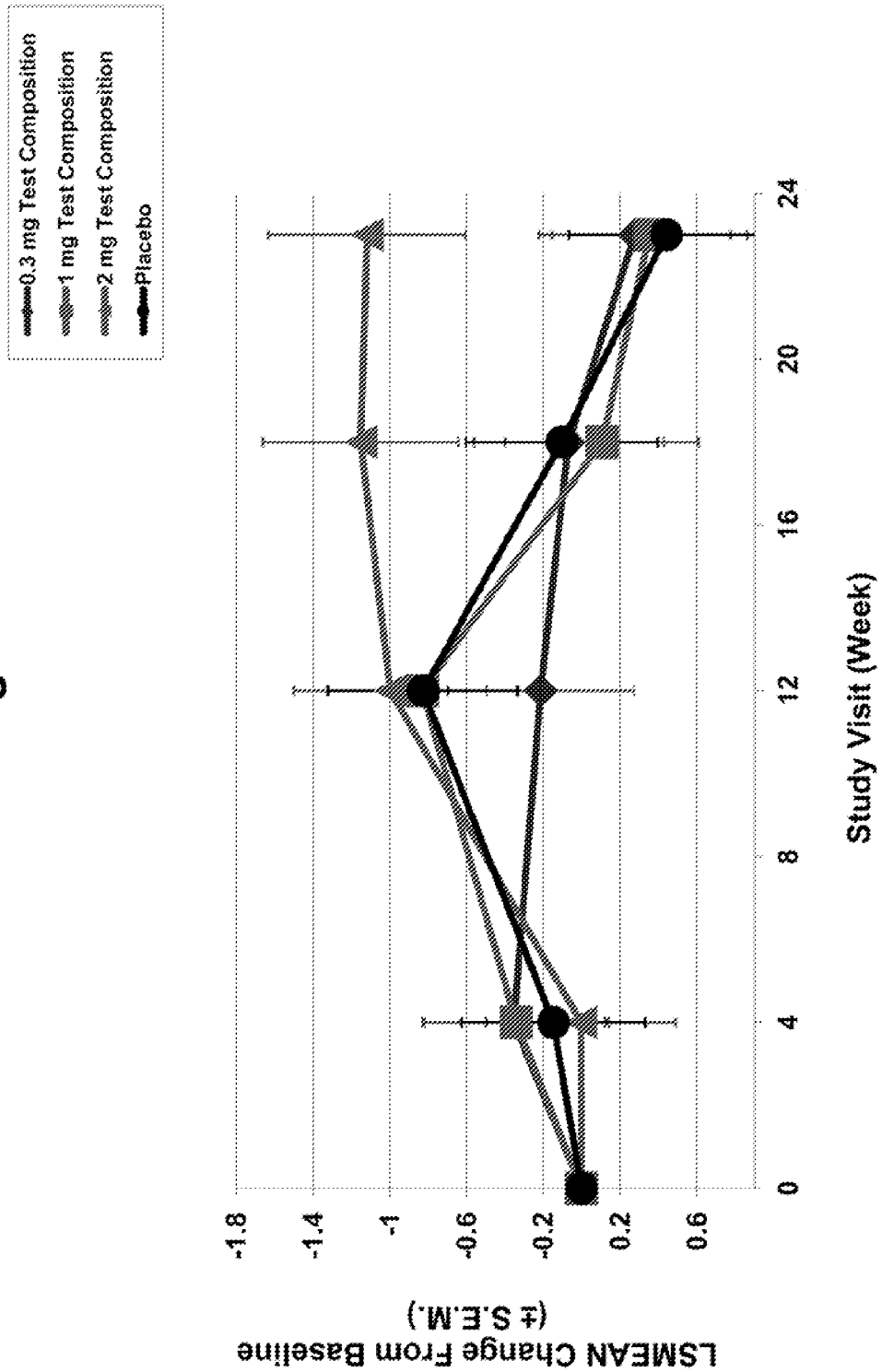
FIG. 2: is a graph of the results from the clinical study of Example 1 Alzheimer's Disease Assessment Scale Cog-11 (ADAS Cog-11).
Figure 3:
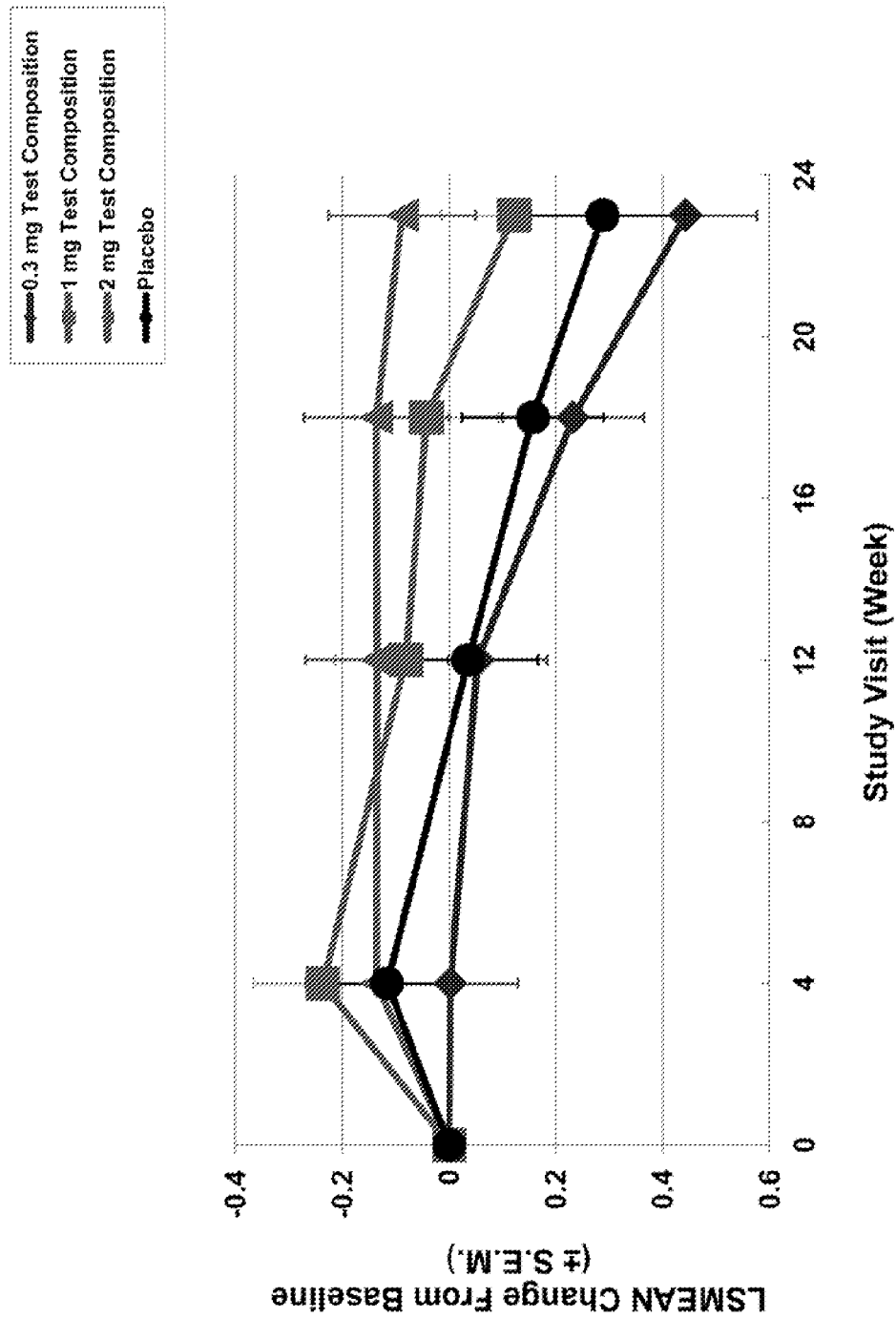
FIG. 3: is a graph of the results from the clinical study of Example 1 for Clinical Dementia Rating-Sum of Boxes (CDR-SB).
Figure 4:
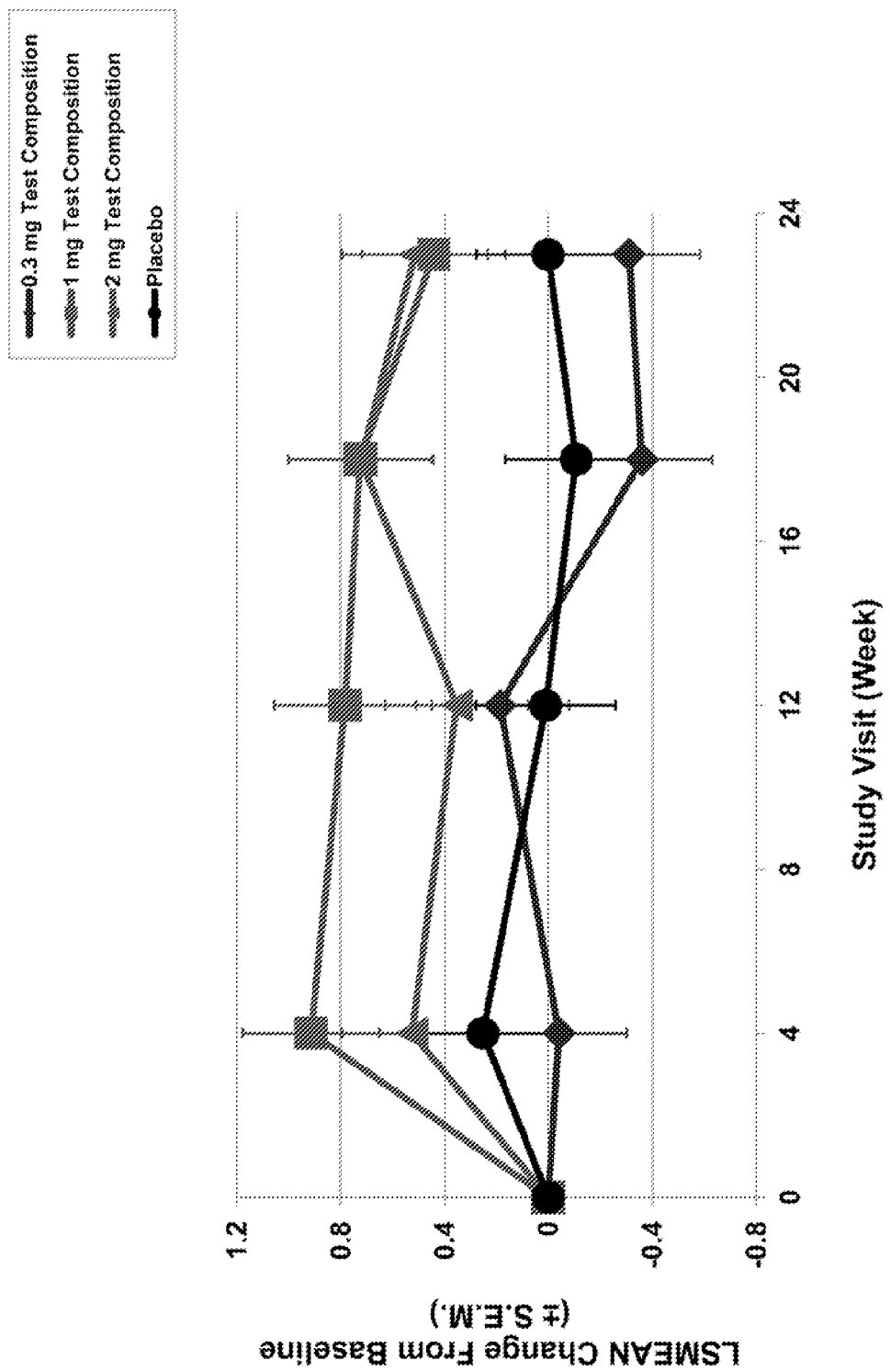
FIG. 4: is a graph of the results from the clinical study of Example 1 for Mini-Mental State Examination (MMSE).
Figure 5:
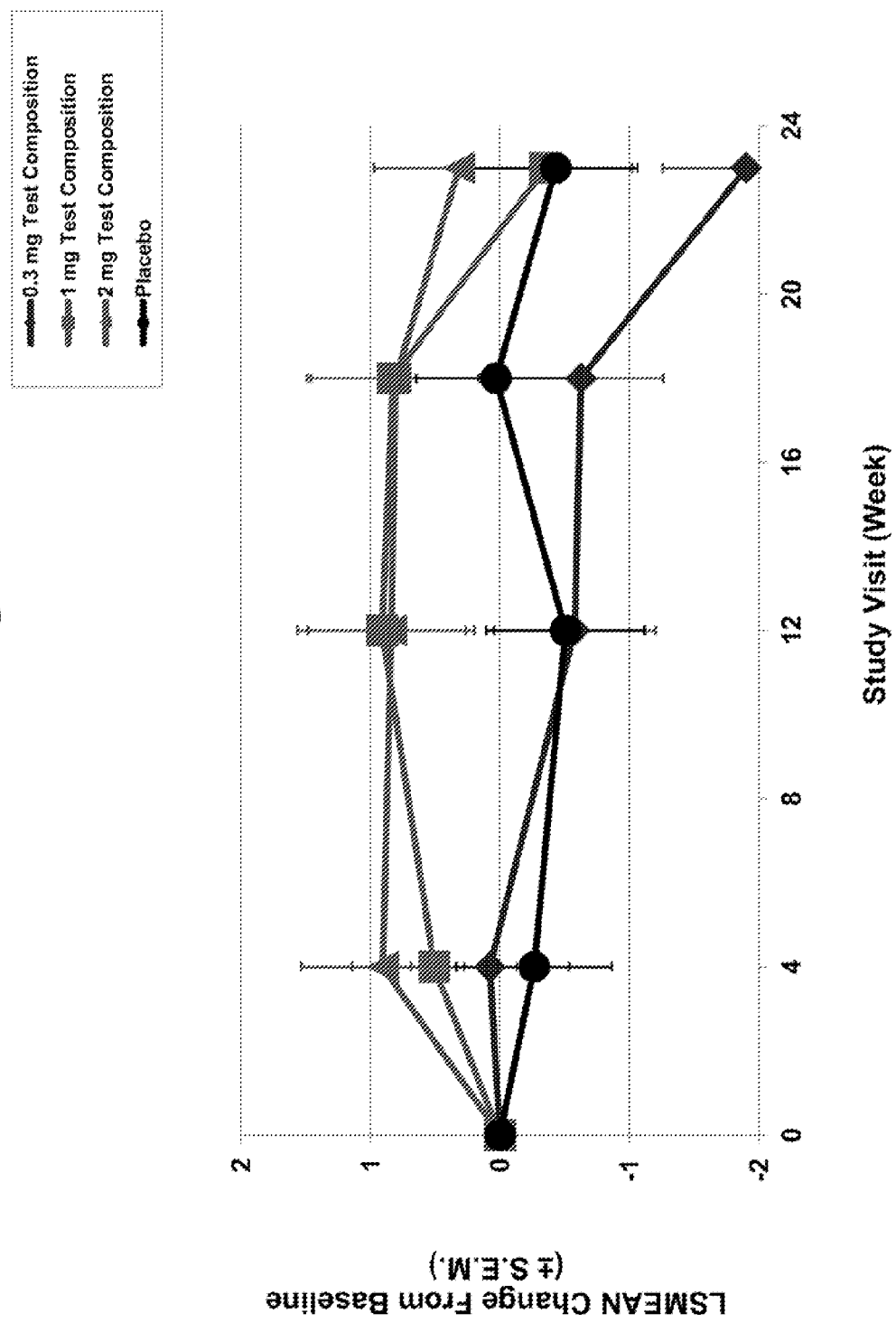
FIG. 5: is a graph of the results from the clinical study of Example 1 for Alzheimer's Disease Cooperative Study Activities of Daily Living (ADCS-ADL).
Figure 6:
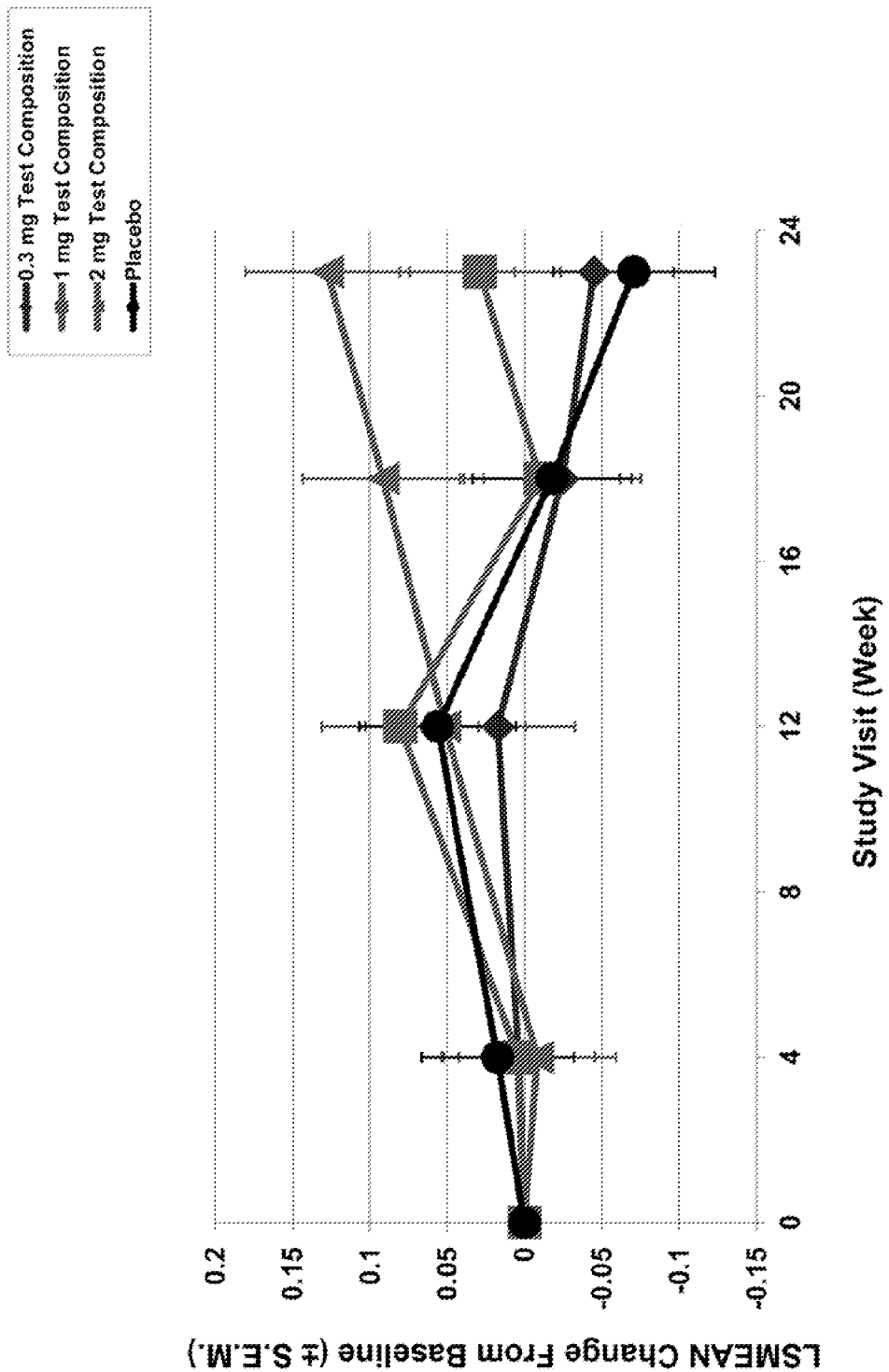
FIG. 6: is a graph of the results from the clinical study of Example 1 for a Cognition Composite Score (composite of ADAS-cog Word Recall, Word Recognition, and Orientation, and COWAT and CFT).
Figure 7:
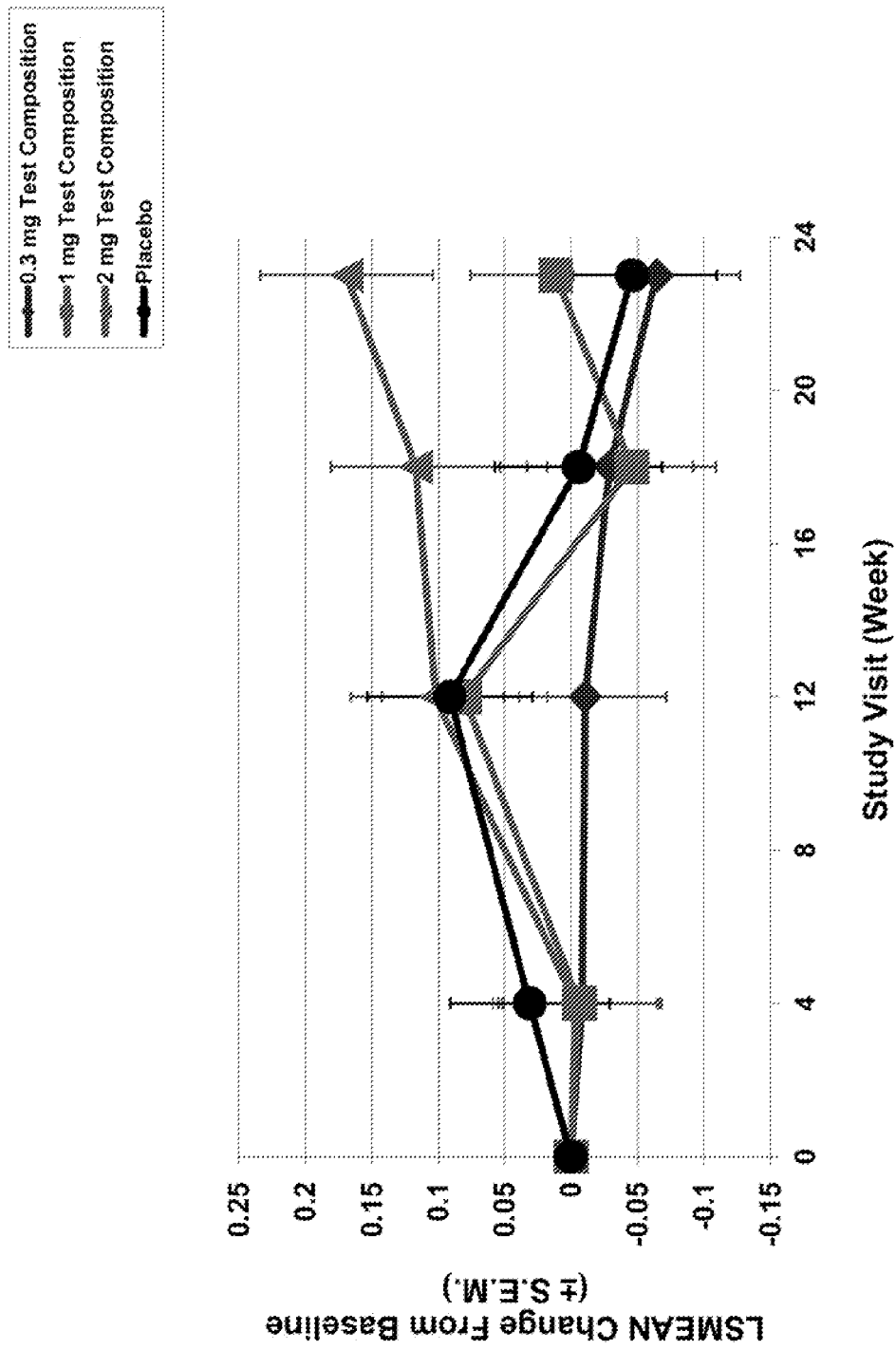
FIG. 7: is a graph of the results from the clinical study of Example 1 for a Memory Composite Score (composite of ADAS-cog Word Recall, Word Recognition, and Orientation).
Figure 8:
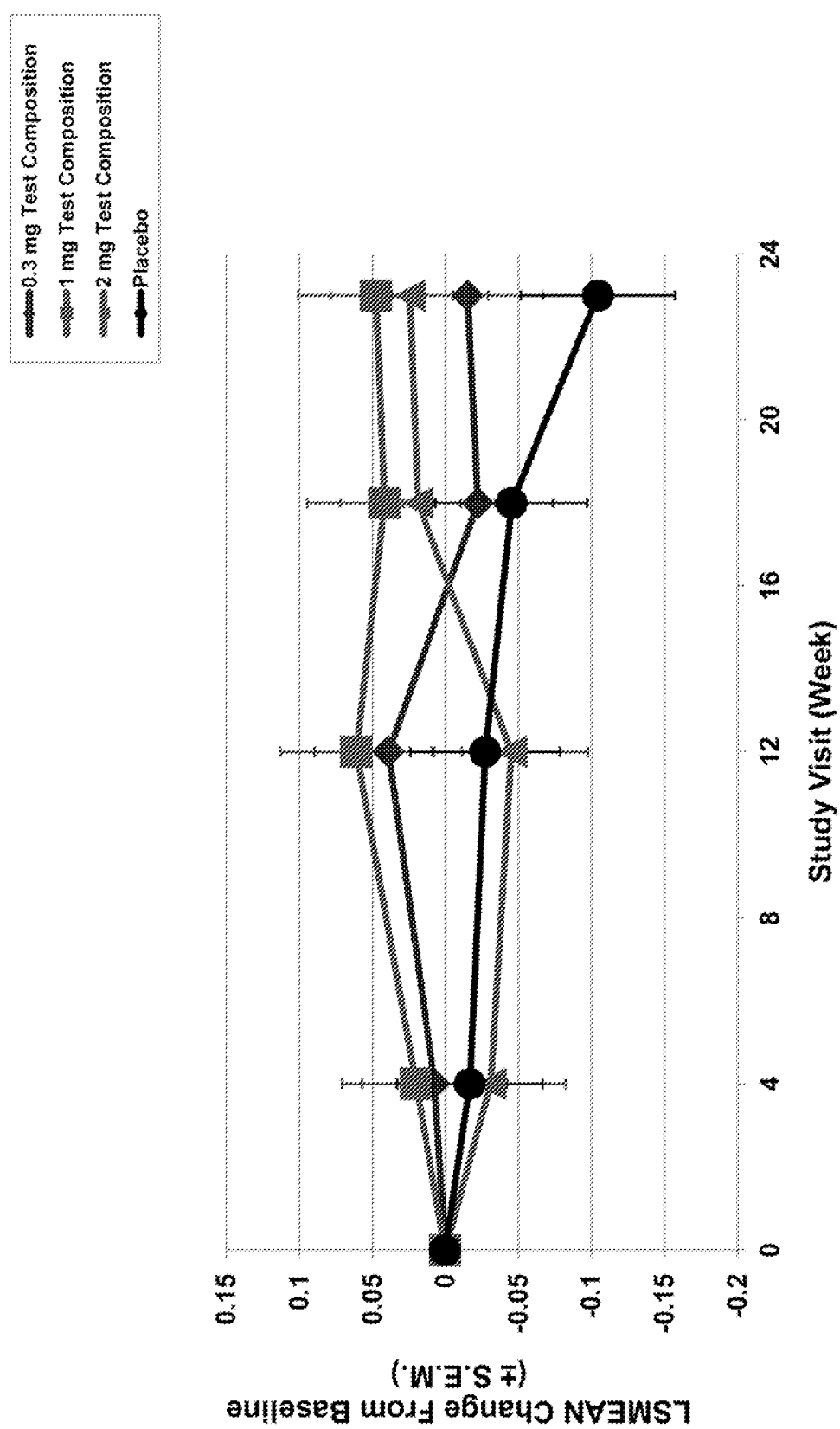
FIG. 8: is a graph of the results from the clinical study of Example 1 for an Executive Function Composite Score (composite of COWAT and CFT).

An aspect of the invention relates to a method comprising administering to a patient in need thereof, for an extended period, an effective dose of (R)-7-chloro-N-(quinuclidin-3-yl)benzo[b]thiophene-2-carboxamide, or a pharmaceutically acceptable salt thereof. It has been discovered that one or more symptoms associated with a cognitive impairment and/or the cognitive impairment can be treated and/or improved by administering to a patient in need thereof, an effective dose of (R)-7-chloro-N-(quinuclidin-3-yl)benzo[b]thiophene-2-carboxamide, or a pharmaceutically acceptable salt thereof, for an extended period.

There are a number of categories used by diagnosticians and physicians to characterize the type and/or degree of a cognitive impairment, or probable cognitive impairment, in a patient. Some of these diagnostic categories include for example Limited Cognitive Impairment, Mild Cognitive Impairment, pre-Alzheimer's disease, prodromal state of Alzheimer's disease, and Alzheimer's disease inclusive of the many sub-diagnostic categories of this disease. A diagnosing or treating physician may use one or more exams/tests to evaluate, characterize and/or diagnose a cognitive impairment, or probable cognitive impairment, such as Alzheimer's disease, or probable Alzheimer's disease, in a patient, which may include, but are not limited to, one or more of the following: physical exams, lab tests, genetic testing (such as APOE-e4 gene, genes causing Autosomal Dominant Alzheimer's Disease (ADAD) or familial Alzheimer's disease), neurological exams, neuropsychological testing, cognitive assessment tests, diagnostic tests, mental status tests, Alzheimer's Disease Cooperative Study Activities of Daily Living (ADCS-ADL), Alzheimer's Disease Assessment Scale-Cognitive Test (e.g., ADAS-Cog-11, ADAS-Cog-13), Category Fluency Test (CFT), Category Naming Test (CNT), Clinical Dementia Rating scale, Clinical Dementia Rating-Sum of Boxes (CDR-SB), Controlled Oral Word Association Tests (COWAT), Detection Task, Identification Task, Mini-Mental State Examination (MMSE), Mini-Cog, Neuropsychiatric Inventory (NPI), One-Back Task, One-Card Learning Task, Trail Making Test Part A, Trail Making Test Part B. The physician may also use other indicia, such as medical history, mood assessment, brain imaging (for example, Magnetic Resonance Imaging (MRI), Computerized Tomography (CT), Positron Emission Tomography (PET) (for example using a radioactive dye, such as Amyvid), Single Photon Emission Computed Tomography (SPECT) Scan, and Magnetic Resonance Spectroscopy Imaging (MRSI)), Electroencephalography (EEG), and/or Electrocardiogram (ECG) as aids in diagnosing Alzheimer's disease. A diagnosing or treating physician may further use one or more of the above-noted exams/tests to monitor the progression of the cognitive impairment, or one or more symptoms associated with the cognitive impairment, in the patient while undergoing treatment, for example to determine the patient's responsiveness to the treatment, for example efficacy of a particular dose amount in the particular patient, or the efficacy of the treatment in the particular patient in treating the cognitive impairment or one or more symptoms associated with the cognitive impairment.

An embodiment of the present invention provides a method of treating a patient in need thereof, comprising: administering to the patient, for an extended period, a daily dose of (R)-7-chloro-N-(quinuclidin-3-yl)benzo[b]thiophene-2-carboxamide, or a pharmaceutically acceptable salt thereof, wherein the patient has a sub-normal score in an at least one diagnostic test, for example at least one of the above-noted exams/tests, such as MMSE, used by a clinician or diagnostician, and wherein the sub-normal score is relative to the particular diagnostic exam/test.

With regard to the use of MMSE testing for diagnosing Alzheimer's disease, the scale that is generally associated with a diagnosis of: (i) mild stage Alzheimer's disease is a score of between 20 and 26, for example 20 to 25, or 20 to 24, (ii) moderate stage Alzheimer's disease is a score of between 10 and 19, for example 12 to 19, or 13 to 19, and (iii) severe stage Alzheimer's disease is a score of below 12, more typically 10 or below.

With regard to the use of ADAS-Cog-13 testing for evaluating or monitoring a patient diagnosed with Alzheimer's disease, a physician may use the patient's previous ADAS-Cog-13 test score (e.g., set as a baseline for subsequent testing), and if the patient achieves an improvement in their score (i.e., a decrease in their overall score from a prior test result), for example an improvement of 2 or greater, such as an improvement greater than 3, greater than 4, greater than 5, or an improvement of 6 or more, this can be an indication of the patient deriving a therapeutic benefit and responding positively to a treatment.

With regard to the use of ADAS-Cog-11 testing for diagnosing Alzheimer's disease, some physicians may characterize a patient as having mild-to-moderate Alzheimer's disease or mild-to-moderate dementia of the Alzheimer's-type with a score of between 10 and 45, for example, between 15 and 40, such as between 15 and 35, between 15 and 30, or between 20 and 45, and may characterize a patient as having severe Alzheimer's disease or severe dementia of the Alzheimer's-type with a score of between 45 and 70, for example, between 50 and 70, such as between 55 and 70, between 60 and 70, or between 50 and 65. Generally, a physician may evaluate the progress of a patient by using the patient's previous ADAS-Cog-11 test score (e.g., set as a baseline for subsequent testing), and if the patient achieves an improvement in their score (i.e., a decrease in their overall score from a prior test result), for example an improvement of 2 or greater, such as an improvement greater than 3, greater than 4, greater than 5, or an improvement of 6 or more, this can be an indication of the patient deriving a therapeutic benefit and responding positively to a treatment.

With regard to the use of CDR-SB testing for diagnosing Alzheimer's disease, generally a patient scoring ≥2 may be characterized as having a cognitive impairment, for example Alzheimer's disease or dementia of the Alzheimer's-type.

Alzheimer's disease may include, unless otherwise specified, any of the sub-diagnostic categories used to characterize the type or degree of cognitive impairment in a patient for treatment purposes. A commonly referenced diagnostic scale for characterizing the degree of cognitive impairment for a patient with Alzheimer's disease includes the 3-stage Alzheimer Disease Model. The 3-stages consist of: mild stage (also referred to as "early Alzheimer's disease" or "mild Alzheimer's disease" or "early stage Alzheimer's disease" or "mild dementia of an Alzheimer's-type"), moderate stage (also referred to as "middle Alzheimer's disease" or "moderate Alzheimer's disease" or "middle stage Alzheimer's disease" or "moderate dementia of an Alzheimer's-type"), and severe stage (also referred to as "late Alzheimer's disease" or "severe Alzheimer's disease" or "late stage Alzheimer's disease" or "severe dementia of an Alzheimer's-type"). For patients with a condition that has not progressed to the point of mild stage Alzheimer's disease, they may be diagnosed as having pre-Alzheimer's disease. It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. Another useful diagnostic scale that is used in characterizing the degree of cognitive impairment for a patient having Alzheimer's disease is the Seven Stage Alzheimer's Disease Model (sometimes known as the "Seven Stage Global Deterioration Scale" or the "Reisberg Scale"). This diagnostic scale divides the progression of the cognitive disorder associated with Alzheimer's disease as follows: Stage 1-no Alzheimer's disease (generally characterized by absence of impairment, no impairment, or normal function), Stage 2-pre-Alzheimer's disease (generally characterized by minimal impairment, normal forgetfulness, or very mild cognitive decline), Stage 3-early-stage Alzheimer's disease (generally characterized by a noticeable cognitive decline, early confusional/mild cognitive impairment, or mild cognitive decline), Stage 4-early-stage/mild Alzheimer's disease (also referred to as late confusional/mild Alzheimer's, and generally characterized by moderate cognitive decline), Stage 5-middle-stage/moderate Alzheimer's (also referred to as early dementia/moderate Alzheimer's disease and generally characterized by moderately severe cognitive decline), Stage 6-middle dementia/moderately severe Alzheimer's disease (also referred to as middle-stage/moderate to late-stage/severe Alzheimer's disease and generally characterized by severe cognitive decline), and Stage 7-late-stage/severe Alzheimer's disease (also referred to as severe dementia or failure-to-thrive, and generally characterized by very severe cognitive decline). It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. As used herein, unless otherwise specified, Alzheimer's disease includes all of the above named diagnostic catagories or disease characterizations. It is also not uncommon for a physician to categorize any one or more of the above noted states of Alzheimer's disease as being probable, for example, probable mild-to-moderate Alzheimer's disease or probable severe Alzheimer's disease, when their diagnosis does not include, for example a physical biopsy or other definitive analysis.

Mild Cognitive Impairment (MCI) is considered by some to be an intermediate stage between normal aging and the onset of Alzheimer's disease. For example, MCI may be characterized by persistent forgetfulness, but may lack some or many of the more debilitating symptoms of Alzheimer's disease. Another set of criteria that may characterize a patient as having mild cognitive impairment suitable for treatment includes a patient that meets the following: 1) memory complaints corroborated by an informant, 2) objective memory impairment for age and education, 3) normal general cognitive function, 4) intact activities of daily living, and 5) the patient does not meet criteria for dementia. In general, a patient characterized as having mild cognitive impairment may not yet have a clinical cognitive deficit. Mild cognitive impairment may also be distinguished from senile dementia in that mild cognitive impairment involves a more persistent and troublesome problem of memory loss for the age of the patient. On the clinical diagnostic scale, mild cognitive impairment is followed, in increased severity, by Alzheimer's disease.

Limited Cognitive Impairment (LCI) describes a cognitive impairment (i.e., symptoms or conditions), which precedes mild cognitive impairment on a clinical diagnostic scale, and includes any chronic or temporary impairment in cognition, learning or memory that prevents or reduces the ability of a patient from achieving their individual potential in these areas. For example, LCIs may include minor impairments to memory associated with focus and concentration (e.g., accuracy and speed of learning and recalling information), working memory (e.g., used in decision making and problem solving), cognition, focus, mental quickness, and mental clarity.

Unless otherwise specified herein (R)-7-chloro-N-(quinuclidin-3-yl)benzo[b]thiophene-2-carboxamide, or a pharmaceutically acceptable salt thereof, is understood to include: (R)-7-chloro-N-(quinuclidin-3-yl)benzo[b]thiophene-2-carboxamide or (R)-7-chloro-N-(quinuclidin-3-yl)benzo[b]thiophene-2-carboxamide, complexed with one or more pharmaceutically acceptable salts and/or one or more solvents, that may be adducted, associated, complexed, or coordinated with the (R)-7-chloro-N-(quinuclidin-3-yl)benzo[b]thiophene-2-carboxamide, such as (R)-7-chloro-N-(quinuclidin-3-yl)benzo[b]thiophene-2-carboxamide, complexed with a stoichiometric amount, for example 1:1, or non-stoichiometric amount of a pharmaceutically acceptable salt and/or solvent, for example (R)-7-chloro-N-(quinuclidin-3-yl)benzo[b]thiophene-2-carboxamide, complexed with an amount between 0.5 and 1.2, such as 0.8, 0.9, or 1.1, of a pharmaceutically acceptable salt and/or solvent. The one or more pharmaceutically acceptable salts may include one or more (for example, a mono-salt or a di-salt, such as an HCl or a di-HCl) of an acid addition salt, such as a mineral acid, a carboxylic acid, or a sulfonic acid. The acid addition salt may include hydrochloric acid, hydrobromic acid, sulfuric acid, phosphoric acid, carbonic acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid, or benzoic acid. The one or more solvent molecules (for example a monosolvate, disolvate, or trisolvate, such as monohydrate, dihydrate, or trihydrate) including water, an alcohol (e.g., methanol, ethanol, or iso-propanol), 1,4 dioxane, or acetone, may be adducted, associated, complexed, or coordinated, with the (R)-7-chloro-N-(quinuclidin-3-yl)benzo[b]thiophene-2-carboxamide. For example, (R)-7-chloro-N-(quinuclidin-3-yl)benzo[b]thiophene-2-carboxamide, or a pharmaceutically acceptable salt thereof, includes, (R)-7-chloro-N-(quinuclidin-3-yl)benzo[b]thiophene-2-carboxamide, hydrochloride; (R)-7-chloro-N-(quinuclidin-3-yl)benzo[b]thiophene-2-carboxamide, hydrochloride, monohydrate (or hydrate); (R)-7-chloro-N-(quinuclidin-3-yl)benzo[b]thiophene-2-carboxamide, hydrochloride, ethanolate; (R)-7-chloro-N-(quinuclidin-3-yl)benzo[b]thiophene-2-carboxamide, hydrochloride, iso-propanolate; (R)-7-chloro-N-(quinuclidin-3-yl)benzo[b]thiophene-2-carboxamide, hydrochloride, acetonate; (R)-7-chloro-N-(quinuclidin-3-yl)benzo[b]thiophene-2-carboxamide, bicarbonate; (R)-7-chloro-N-(quinuclidin-3-yl)benzo[b]thiophene-2-carboxamide, bicarbonate, hydrate; (R)-7-chloro-N-(quinuclidin-3-yl)benzo[b]thiophene-2-carboxamide, bicarbonate, ethanolate; (R)-7-chloro-N-(quinuclidin-3-yl)benzo[b]thiophene-2-carboxamide, acetate; (R)-7-chloro-N-(quinuclidin-3-yl)benzo[b]thiophene-2-carboxamide, acetate, hydrate; (R)-7-chloro-N-(quinuclidin-3-yl)benzo[b]thiophene-2-carboxamide, acetate, ethanolate; (R)-7-chloro-N-(quinuclidin-3-yl)benzo[b]thiophene-2-carboxamide, lactate; (R)-7-chloro-N-(quinuclidin-3-yl)benzo[b]thiophene-2-carboxamide, lactate, hydrate; or (R)-7-chloro-N-(quinuclidin-3-yl)benzo[b]thiophene-2-carboxamide, lactate, ethanolate. For any particular (R)-7-chloro-N-(quinuclidin-3-yl)benzo[b]thiophene-2-carboxamide, or a pharmaceutically acceptable salt thereof, one or more of the optically active forms (stereoisomers, such as the enantiomers and/or the diastereomers), the racemates, and/or the polymorph forms of a compound may be active and/or preferred. For example, (R)-7-chloro-N-(quinuclidin-3-yl)benzo[b]thiophene-2-carboxamide, hydrochloride, monohydrate has at least two polymorphic forms: crystalline Form I ("herein referred to as "polymorph form I") and crystalline Form II ("herein referred to as "polymorph form II"), wherein polymorph form I is preferred.

Polymorph Form I of (R)-7-chloro-N-(quinuclidin-3-yl)benzo[b]thiophene-2-carboxamide, hydrochloride, monohydrate, may be characterized by: (i) an x-ray powder diffraction pattern having peaks expressed as 2θ at one or both of 17.48 and 20.58±0.20 degrees; (ii) an x-ray powder diffraction pattern further having at least one peak expressed as 2θ at 4.50, 9.04, 14.60, 15.14, 15.80, 16.60, 18.16, 18.44, 19.48, 21.74, and 25.46±0.20 degrees; (iii) an x-ray powder diffraction pattern further having at least two peaks expressed as 2θ at 4.50, 9.04, 14.60, 15.14, 15.80, 16.60, 18.16, 18.44, 19.48, 21.74 and 25.46±0.20 degrees; (iv) an x-ray powder diffraction pattern further having at least four peaks expressed as 2θ at 4.50, 9.04, 14.60, 15.14, 15.80, 16.60, 18.16, 18.44, 19.48, 21.74 and 25.46±0.20 degrees; (v) an x-ray powder diffraction pattern further having at least six peaks expressed as 2θ at 4.50, 9.04, 14.60, 15.14, 15.80, 16.60, 18.16, 18.44, 19.48, 21.74 and 25.46±0.20 degrees;

(vi) an x-ray powder diffraction pattern further having at least eight peaks expressed as 2θ at 4.50, 9.04, 14.60, 15.14, 15.80, 16.60, 18.16, 18.44, 19.48, 21.74 and 25.46±0.20 degrees; and/or (vii) an x-ray powder diffraction pattern further having peaks expressed as 2θ at 4.50, 9.04, 14.60, 15.14, 15.80, 16.60, 18.16, 18.44, 19.48, 21.74 and 25.46±0.20 degrees; when measured against an internal silicon standard.

Polymorph Form II of (R)-7-chloro-N-(quinuclidin-3-yl)benzo[b]thiophene-2-carboxamide, hydrochloride, monohydrate, may be characterized by: (i) an x-ray powder diffraction pattern having peaks expressed as 2θ at one or both of 21.16 and 21.38±0.20 degrees; (ii) an x-ray powder diffraction pattern further having at least one peak expressed as 2θ at 4.48, 9.00, 13.58, 15.62, 16.48, 19.02, 19.44, 22.46 and 25.00±0.20 degrees; (iii) an x-ray powder diffraction pattern further having at least two peaks expressed as 2θ at 4.48, 9.00, 13.58, 15.62, 16.48, 19.02, 19.44, 22.46 and 25.00±0.2 degrees; (iv) an x-ray powder diffraction pattern further having at least four peaks expressed as 2θ at 4.48, 9.00, 13.58, 15.62, 16.48, 19.02, 19.44, 22.46 and 25.00±0.2 degrees; (v) an x-ray powder diffraction pattern further having at least six peaks expressed as 2θ at 4.48, 9.00, 13.58, 15.62, 16.48, 19.02, 19.44, 22.46 and 25.00±0.2 degrees; (vi) an x-ray powder diffraction pattern further having at least eight peaks expressed as 2θ at 4.48, 9.00, 13.58, 15.62, 16.48, 19.02, 19.44, 22.46 and 25.00±0.2 degrees; and/or (vii) an x-ray powder diffraction pattern further having peaks expressed as 2θ at 4.48, 9.00, 13.58, 15.62, 16.48, 19.02, 19.44, 22.46 and 25.00±0.2 degrees; when measured against an internal silicon standard.

As used herein, the term "dose", unless otherwise specified, refers to a physically discrete unit suitable as a unitary dosage for a human subject, each unit comprising between 80 and 115 wt. %, for example between 85 and 110 wt. %, between 90 and 110 wt. %, between 93 wt. % and 107 wt. %, between 95 wt. % and 105 wt. %, or between 97 wt. % and 103 wt. % of a designated quantity of (R)-7-chloro-N-(quinuclidin-3-yl)benzo[b]thiophene-2-carboxamide, or a pharmaceutically acceptable salt thereof, alone or in the form of a pharmaceutical composition wherein the (R)-7-chloro-N-(quinuclidin-3-yl)benzo[b]thiophene-2-carboxamide, or a pharmaceutically acceptable salt thereof, is present with one or more of the following: pharmaceutically acceptable carriers, diluents, or excipients. For example, a tablet designated as comprising 1.0 mg of (R)-7-chloro-N-(quinuclidin-3-yl)benzo[b]thiophene-2-carboxamide, or a pharmaceutically acceptable salt thereof, may have between 80 and 115 wt. % of the 1.0 mg (or 0.8 mg and 1.15 mg) of the (R)-7-chloro-N-(quinuclidin-3-yl)benzo[b]thiophene-2-carboxamide, or a pharmaceutically acceptable salt thereof.

As used herein "daily dose" (which should be understood to be a fixed daily dose of the designated amount for the extended period) of (R)-7-chloro-N-(quinuclidin-3-yl)benzo[b]thiophene-2-carboxamide, or a pharmaceutically acceptable salt thereof, which includes, but is not limited to an initial daily dose of (R)-7-chloro-N-(quinuclidin-3-yl)benzo[b]thiophene-2-carboxamide, or a pharmaceutically acceptable salt thereof, may include a designated amount of between 0.1 and 4.5 mg of (R)-7-chloro-N-(quinuclidin-3-yl)benzo[b]thiophene-2-carboxamide, or a pharmaceutically acceptable salt thereof, per day, preferably in a single dose form. For example, a daily dose of (R)-7-chloro-N-(quinuclidin-3-yl)benzo[b]thiophene-2-carboxamide, or a pharmaceutically acceptable salt thereof, may include an amount of between 0.2 mg and 4.3 mg of (R)-7-chloro-N-(quinuclidin-3-yl)benzo[b]thiophene-2-carboxamide, or a pharmaceutically acceptable salt thereof, per day, such as an amount of between 0.7 mg and 4.0 mg, between 0.7 mg and 3.7 mg, between 0.7 mg and 3.5 mg, between 0.7 mg and 3.3 mg, between 0.7 mg and 3.0 mg, between 0.7 mg and 2.7 mg, between 0.7 mg and 2.5 mg, between 0.7 mg and 2.3 mg, between 0.7 mg and 2.0 mg, between 0.7 mg and 1.7 mg, between 0.7 mg and 1.5 mg, between 0.7 mg and 1.3 mg, between 0.7 mg and 1.0 mg, between 1.0 mg and 4.5 mg, between 1.0 mg and 4.3 mg, between 1.0 mg and 4.0 mg, between 1.0 mg and 3.5 mg, between 1.0 mg and 3.0 mg, between 1.0 mg and 2.5 mg, between 1.0 mg and 2.0 mg, between 1.7 mg and 4.5 mg, between 1.7 mg and 4.3 mg, between 1.7 mg and 4.0 mg, between 1.7 mg and 3.7 mg, between 1.7 mg and 3.5 mg, between 1.7 mg and 3.3 mg, between 1.7 mg and 3.0 mg, between 1.7 mg and 2.7 mg, between 1.7 mg and 2.5 mg, between 1.7 mg and 2.3 mg, between 2.0 mg and 4.5 mg, between 2.0 mg and 4.3 mg, between 2.0 mg and 4.0 mg, between 2.0 mg and 3.7 mg, between 2.0 mg and 3.5 mg, between 2.0 mg and 3.3 mg, between 2.0 mg and 3.0 mg, between 2.7 mg and 4.5 mg, between 2.7 mg and 4.3 mg, between 2.7 mg and 4.0 mg, between 2.7 mg and 3.7 mg, between 2.7 mg and 3.5 mg, between 2.7 mg and 3.3 mg, between 3.0 mg and 4.5 mg, between 3.0 mg and 4.3 mg, between 3.0 mg and 4.0 mg, between 3.0 mg and 3.7 mg, between 3.0 mg and 3.5 mg, between 3.0 mg and 3.3 mg, between 3.3 mg and 4.5 mg, between 3.3 mg and 4.3 mg, between 3.5 mg and 4.5 mg, between 3.7 mg and 4.5 mg, or between 3.7 mg and 4.3 mg of (R)-7-chloro-N-(quinuclidin-3-yl)benzo[b]thiophene-2-carboxamide, or a pharmaceutically acceptable salt thereof.

A daily dose of (R)-7-chloro-N-(quinuclidin-3-yl)benzo[b]thiophene-2-carboxamide, or a pharmaceutically acceptable salt thereof, which can include an initial daily dose of (R)-7-chloro-N-(quinuclidin-3-yl)benzo[b]thiophene-2-carboxamide, or a pharmaceutically acceptable salt thereof, may include a designated amount of at least 0.1 mg of (R)-7-chloro-N-(quinuclidin-3-yl)benzo[b]thiophene-2-carboxamide, or a pharmaceutically acceptable salt thereof, per day, such as an amount of 0.3 mg, 0.7 mg, 1.0 mg, 1.3 mg, 1.5 mg, 1.7 mg, 2.0 mg, 2.3 mg, 2.5 mg, 2.7 mg, 3.0 mg, 3.3 mg, 3.5 mg, 3.7 mg, 4.0 mg, 4.3 mg, or 4.5 mg of (R)-7-chloro-N-(quinuclidin-3-yl)benzo[b]thiophene-2-carboxamide, or a pharmaceutically acceptable salt thereof.

A daily dose of (R)-7-chloro-N-(quinuclidin-3-yl)benzo[b]thiophene-2-carboxamide, or a pharmaceutically acceptable salt thereof, may include a single unit dose of (R)-7-chloro-N-(quinuclidin-3-yl)benzo[b]thiophene-2-carboxamide, or a pharmaceutically acceptable salt thereof, per day. A daily dose of (R)-7-chloro-N-(quinuclidin-3-yl)benzo[b]thiophene-2-carboxamide, or a pharmaceutically acceptable salt thereof, may include more than one single unit dose of (R)-7-chloro-N-(quinuclidin-3-yl)benzo[b]thiophene-2-carboxamide, or a pharmaceutically acceptable salt thereof, per day; for example, a daily dose may include two unit doses, such as a first dosage amount of (R)-7-chloro-N-(quinuclidin-3-yl)benzo[b]thiophene-2-carboxamide, or a pharmaceutically acceptable salt thereof, along with a second dosage amount of (R)-7-chloro-N-(quinuclidin-3-yl)benzo[b]thiophene-2-carboxamide, or a pharmaceutically acceptable salt thereof, wherein the first dosage amount and the second dosage amount may be the same amount of (R)-7-chloro-N-(quinuclidin-3-yl)benzo[b]thiophene-2-carboxamide, or a pharmaceutically acceptable salt thereof, or a different amount of (R)-7-chloro-N-(quinuclidin-3-yl)benzo[b]thiophene-2-carboxamide, or a pharmaceutically acceptable salt thereof. It is preferred that the daily dose of (R)-7-chloro-N-(quinuclidin-3-yl)benzo[b]thiophene-2-carboxamide, or a pharmaceutically acceptable salt thereof, is a single dose of (R)-7-chloro-N-(quinuclidin-3-yl)benzo[b]thiophene-2-carboxamide, or a pharmaceutically acceptable salt thereof, administered once per day.

Administration of a dosage of (R)-7-chloro-N-(quinuclidin-3-yl)benzo[b]thiophene-2-carboxamide, or a pharmaceutically acceptable salt thereof, may be administered therapeutically and/or prophylactically, for example, the (R)-7-chloro-N-(quinuclidin-3-yl)benzo[b]thiophene-2-carboxamide, or a pharmaceutically acceptable salt thereof, dosage may be a therapeutically administered dosage of (R)-7-chloro-N-(quinuclidin-3-yl)benzo[b]thiophene-2-carboxamide, or a pharmaceutically acceptable salt thereof, and/or a prophylactically administered dosage of (R)-7-chloro-N-(quinuclidin-3-yl)benzo[b]thiophene-2-carboxamide, or a pharmaceutically acceptable salt thereof.

An initial daily dose, as disclosed herein, should be understood to include a daily dose that is initially administered to a patient for an initial extended period of time.

An extended period of administering a dosage of (R)-7-chloro-N-(quinuclidin-3-yl)benzo[b]thiophene-2-carboxamide, or a pharmaceutically acceptable salt thereof, may include up to 5 years or more, for example, an extended period may include at least 6 weeks, such as 8 weeks or more, 10 weeks or more, 12 weeks or more, 14 weeks or more, 16 weeks or more, 17 weeks or more, 18 weeks or more, 20 weeks or more, 22 weeks or more, 23 weeks or more, 24 weeks or more, 26 weeks or more, 28 weeks or more, 30 weeks or more, 32 weeks or more, 34 weeks or more, 36 weeks or more, 38 weeks or more, 40 weeks or more, 42 weeks or more, 44 weeks or more, 46 weeks or more, 48 weeks or more, 50 weeks or more, or administering a dosage of (R)-7-chloro-N-(quinuclidin-3-yl)benzo[b]thiophene-2-carboxamide, or a pharmaceutically acceptable salt thereof, for 52 weeks or more.

As used herein, the term "treating" (or "treat" or "treatment"), unless otherwise specified, includes the generally accepted meaning which encompasses improving, modifying, decreasing, prohibiting, preventing, restraining, minimizing, slowing, halting, stopping, curing, and/or reversing a symptom associated with a disease and/or a disease. Treatment may include both therapeutic and prophylactic administration. For example, treatment of a cognitive impairment, in a patient diagnosed as having a cognitive impairment, may include, but is not limited to, curing the cognitive impairment, preventing the deterioration of one or more symptoms associated with the cognitive impairment; improving cognition in a patient suffering from the cognitive impairment, slowing the progression of the cognitive impairment and/or modifying the cognitive impairment.

As used herein, the term "cognitive impairment", unless otherwise specified, includes at least one of the following: Limited Cognitive Impairment (LCI), Mild Cognitive Impairment (MCI), Alzheimer's disease (or dementia of an Alzheimer's-type) or a particular stage of Alzheimer's disease, inclusive of pre-Alzheimer's disease, early Alzheimer's disease, mild Alzheimer's disease, moderate Alzheimer's disease, severe Alzheimer's disease, pre-Alzheimer's-to-mild Alzheimer's disease, mild-to-moderate Alzheimer's disease, or moderate-to-severe Alzheimer's disease.

An aspect of the invention may include administration of a dose of (R)-7-chloro-N-(quinuclidin-3-yl)benzo[b]thiophene-2-carboxamide, or a pharmaceutically acceptable salt thereof, such as a daily dose of (R)-7-chloro-N-(quinuclidin-3-yl)benzo[b]thiophene-2-carboxamide, or a pharmaceutically acceptable salt thereof, that is co-administered with an acetylcholine esterase inhibitor ("AChIE"), for example, co-administration of an acetylcholine esterase inhibitor is inclusive of administration prior to, simultaneous with, substantially simultaneously with, or after the period of treatment with administration of a dose of (R)-7-chloro-N-(quinuclidin-3-yl)benzo[b]thiophene-2-carboxamide, or a pharmaceutically acceptable salt thereof.

An aspect of the invention provides a pharmaceutical composition comprising (R)-7-chloro-N-(quinuclidin-3-yl)benzo[b]thiophene-2-carboxamide, or a pharmaceutically acceptable salt thereof, and a method of administering the same. A further aspect of the invention provides a method of administering to a patient in need thereof, a daily dose of (R)-7-chloro-N-(quinuclidin-3-yl)benzo[b]thiophene-2-carboxamide, or a pharmaceutically acceptable salt thereof, or a pharmaceutical composition comprising (R)-7-chloro-N-(quinuclidin-3-yl)benzo[b]thiophene-2-carboxamide, or a pharmaceutically acceptable salt thereof, for an extended period.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method treats one or more symptoms associated with the cognitive impairment.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method treats the cognitive impairment.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves cognition in said cognitively impaired patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a positive effect on cognition or a positive effect on clinical function in said cognitively impaired patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a positive effect on cognition or a positive effect on clinical function in said cognitively impaired patient, and wherein said patient has been previously treated or is currently being treated with an AChEI.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves one or more cognitive symptoms associated with the cognitive impairment.

A further aspect of the invention provides a method of treating a patient previously treated, or currently being treated, with an AChEI, that is suffering from, or has been diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves one or more symptoms associated with the cognitive impairment in the previously, or currently, AChEI treated patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves one or more behavioral symptoms associated with the cognitive impairment.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method improves said patient towards a non-disease status.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method prevents the deterioration of one or more symptoms in said cognitively impaired patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method prevents the deterioration of the cognitive impairment in said patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a pro-cognitive effect in at least one of the following: visual motor, learning, delayed memory, or executive function, in said patient.

A further aspect of the invention provides a method of treating a patient suffering from, or diagnosed with having, a cognitive impairment, for example Alzheimer's disease, dementia of an Alzheimer's type, MCI, or LCI, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, wherein the method provides a pro-cognitive effect, exclusive of attention, in at least one of the following: visual motor, learning, delayed memory, or executive function, in said patient.

It should be noted that for any or all of the above-noted aspects that the daily dose may include between 80 and 115 wt. %, for example between 90 and 110 wt. %, between 95 wt. % and 105 wt. %, or between 97 wt. % and 103 wt. % of a designated quantity of (R)-7-chloro-N-(quinuclidin-3-yl)benzo[b]thiophene-2-carboxamide, or a pharmaceutically acceptable salt thereof, alone or in the form of a pharmaceutical composition. It should be further noted that for any or all of the above-noted aspects that the daily dose may include a designated amount of between 0.1 mg and 4.5 mg of (R)-7-chloro-N-(quinuclidin-3-yl)benzo[b]thiophene-2-carboxamide, or a pharmaceutically acceptable salt thereof, per day, for example, an amount of between 0.7 mg and 4.3 mg, between 0.7 mg and 3.3 mg, between 1.0 mg and 4.0 mg, between 1.0 mg and 3.0 mg, between 1.7 mg and 4.3 mg, between 2.0 mg and 4.5 mg, between 2.0 mg and 4.0 mg, between 2.0 mg and 3.0 mg, between 2.7 mg and 3.7 mg, between 3.0 mg and 4.5 mg, between 3.0 mg and 4.0 mg, or between 3.5 mg and 4.5 mg, of (R)-7-chloro-N-(quinuclidin-3-yl)benzo[b]thiophene-2-carboxamide, or a pharmaceutically acceptable salt thereof.

It should be noted that for any or all of the above-noted aspects that the extended period may include at least 6 weeks, for example 8 weeks or more, 12 weeks or more, 16 weeks or more, 17 weeks or more, 18 weeks or more, 23 weeks or more, 24 weeks or more, 30 weeks or more, 36 weeks or more, 42 weeks or more, 48 weeks or more, or 52 weeks or more.

A further aspect of the present invention provides a method of administering to a patient in need thereof, for an extended period, a pharmaceutical composition comprising a daily dose of (R)-7-chloro-N-(quinuclidin-3-yl)benzo[b]thiophene-2-carboxamide, or a pharmaceutically acceptable salt thereof, for example (R)-7-chloro-N-(quinuclidin-3-yl)benzo[b]thiophene-2-carboxamide, hydrochloride, monohydrate, such as (R)-7-chloro-N-(quinuclidin-3-yl)benzo[b]thiophene-2-carboxamide, hydrochloride, monohydrate, polymorph form I, is adjusted, for example increased or decreased from a previous daily dose, to an amount of at least 0.3 mg, 0.7 mg, 1.0 mg, 1.3 mg, 1.5 mg, 1.7 mg, 2.0 mg, 2.3 mg, 2.5 mg, 2.7 mg, 3.0 mg, 3.3 mg, 3.5 mg, or 3.7 mg, to no greater than 4.5 mg, such as to no greater than 4.3 mg or to no greater than 4.0 mg, if the daily dose is well tolerated over an extended period of time, for example for at least 6, 7, 8, 9, 10, 11, 12, 13, 14, 15, 16, 17, 18, 19, 20, 21, 22, 23, 24, 28, 30, 32, 34, 36, 38, 40, 42, 44, 46, 48, 50, or 52 weeks. For example, a further aspect of the present invention provides a method of administering to a patient in need thereof, for an extended period, a pharmaceutical composition comprising a daily dose of (R)-7-chloro-N-(quinuclidin-3-yl)benzo[b]thiophene-2-carboxamide, or a pharmaceutically acceptable salt thereof, such as (R)-7-chloro-N-(quinuclidin-3-yl)benzo[b]thiophene-2-carboxamide, hydrochloride, monohydrate, or (R)-7-chloro-N-(quinuclidin-3-yl)benzo[b]thiophene-2-carboxamide, hydrochloride, monohydrate, polymorph form I, is adjusted, for example increased or decreased from a previous daily amount, to an amount of at least 1.0 mg, 1.7 mg, 2.0 mg, 2.3 mg, 2.7 mg, 3.0 mg, 3.3 mg, or 3.7 mg, to no greater than 4.5 mg, such as to no greater than 4.3 mg or to no greater than 4.0 mg, if the daily dose is well tolerated over at least 6, 8, 12, 14, 16, 18, 23, or 24 weeks, such as well tolerated over at least 6, 12, 18, 23, or 24 weeks.

A further aspect of the present invention provides a method of treating a patient in need thereof, comprising: administering to the patient, for an extended period, a pharmaceutical composition comprising a daily dose of (R)-7-chloro-N-(quinuclidin-3-yl)benzo[b]thiophene-2-carboxamide, or a pharmaceutically acceptable salt thereof, in either a fasted or fed mode. A further aspect of the present invention provides a pharmaceutical composition comprising a daily dose of (R)-7-chloro-N-(quinuclidin-3-yl)benzo[b]thiophene-2-carboxamide, or a pharmaceutically acceptable salt thereof, that is formulated to be administered in either a fasted or fed mode, or is capable of being administered in either a fasted or fed mode.

A further aspect of the present invention provides a method of treating a patient in need thereof, comprising adjusting, for example increasing or decreasing, a daily dose of (R)-7-chloro-N-(quinuclidin-3-yl)benzo[b]thiophene-2-carboxamide, or a pharmaceutically acceptable salt thereof, administered to the patient suffering from a cognitive impairment, for example mild Alzheimer's disease, moderate Alzheimer's disease, severe Alzheimer's disease, or mild-to-moderate Alzheimer's disease, to improve or prevent deterioration of one or more of the symptoms associated with the cognitive impairment. For example, in a further aspect, the method of treating provides that the daily dose is adjusted, for example increased or decreased, according to the patient's responsiveness to the treatment; or the rate of deterioration of one or more symptoms associated with the cognitive impairment.

A further aspect of the present invention provides a method of treating a patient in need thereof, comprising for example increasing or decreasing, a daily dose of (R)-7-chloro-N-(quinuclidin-3-yl)benzo[b]thiophene-2-carboxamide, or a pharmaceutically acceptable salt thereof, administered to the patient suffering from dementia of the Alzheimer's-type, such as mild dementia of the Alzheimer's type, moderate dementia of the Alzheimer's type, severe dementia of the Alzheimer's type, or mild-to-moderate dementia of the Alzheimer's type, to improve or prevent deterioration of one or more of the symptoms associated with the dementia of the Alzheimer's-type. For example, in a further aspect, the method of treating provides that the daily dose is adjusted, for example increased or decreased, according to the patient's responsiveness to the treatment; or the rate of deterioration of one or more symptoms associated with the cognitive impairment.

A further aspect of the present invention provides a method of improving one or more cognitive symptoms, improving one or more behavioral symptoms, or both, associated with a cognitive impairment, for example mild-to-moderate Alzheimer's disease or mild-to-moderate dementia of the Alzheimer's-type, comprising: administering to a patient in need thereof, for an extended period, a pharmaceutical composition comprising a daily dose of (R)-7-chloro-N-(quinuclidin-3-yl)benzo[b]thiophene-2-carboxamide, or a pharmaceutically acceptable salt thereof. A further aspect of the present invention provides a method of treating one or more symptoms associated with Alzheimer's disease, one or more symptoms associated with dementia of the Alzheimer's-type, or both, comprising: administering to a patient in need thereof, a pharmaceutical composition comprising a daily dose of (R)-7-chloro-N-(quinuclidin-3-yl)benzo[b]thiophene-2-carboxamide, or a pharmaceutically acceptable salt thereof, for an extended period.

In a further aspect of the present invention, the method provides a pro-cognitive effect in a patient suffering from, or diagnosed as having, Alzheimer's disease or dementia of the Alzheimer's-type, comprising: administering to a patient in need thereof, for an extended period, a pharmaceutical composition comprising a daily dose of (R)-7-chloro-N-(quinuclidin-3-yl)benzo[b]thiophene-2-carboxamide, or a pharmaceutically acceptable salt thereof, for an extended period, wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

A particular aspect of the present invention provides a method of treating dementia of the Alzheimer's type, comprising: administering to a patient in need thereof an effective amount of (R)-7-chloro-N-(quinuclidin-3-yl)benzo[b]thiophene-2-carboxamide, or a pharmaceutically acceptable salt thereof, for an extended period.

In a further particular aspect, comprising any one of the above-noted particular aspects, the effective amount is administered in a daily dose.

In a further particular aspect, comprising any one of the above-noted particular aspects, the daily dose comprises between 1.0 mg and 4.5 mg of (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the daily dose comprises between 1.5 mg and 4.3 mg of (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the daily dose comprises between 1.8 mg and 3.2 mg of (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the extended period is at least 6 weeks, for example at least 12 weeks, at least 23 weeks, or at least 24 weeks.

In a further particular aspect, comprising any one of the above-noted particular aspects, the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate.

In a further particular aspect, comprising any one of the above-noted particular aspects, the pharmaceutically acceptable salt of the (R)-7-chloro-N-(quinuclidin-3-yl)benzo[b]thiophene-2-carboxamide, is (R)-7-chloro-N-(quinuclidin- 3-yl)benzo[b]thiophene-2-carboxamide, hydrochloride, monohydrate, polymorph form I.

In a further particular aspect, comprising any one of the above-noted particular aspects, the (R)-7-chloro-N-(quinuclidin-3-yl)benzo[b]thiophene-2-carboxamide, or a pharmaceutically acceptable salt thereof, is administered in the form of a pharmaceutical composition comprising at least one pharmaceutically acceptable carrier, excipient or diluent.

In a further particular aspect, comprising any one of the above-noted particular aspects, the pharmaceutical composition is in the form of a tablet.

A particular aspect of the present invention provides a method of treating a patient having Alzheimer's disease, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the extended period of administering the daily dose is for at least 6 weeks.

In a further particular aspect, comprising any one of the above-noted particular aspects, the Alzheimer's disease is mild-to-moderate Alzheimer's disease.

In a further particular aspect, comprising any one of the above-noted particular aspects, the daily dose is an initial daily dose.

In a further particular aspect, comprising any one of the above-noted particular aspects, the treating includes improving cognition of the patient.

In a further particular aspect, comprising any one of the above-noted particular aspects, the treating includes treating a symptom associated with Alzheimer's disease.

In a further particular aspect, comprising any one of the above-noted particular aspects, the treating includes improving a symptom associated with Alzheimer's disease.

In a further particular aspect, comprising any one of the above-noted particular aspects, the treating includes preventing progression of Alzheimer's disease.

In a further particular aspect, comprising any one of the above-noted particular aspects, the patient has been diagnosed as having mild-to-moderate Alzheimer's disease.

In a further particular aspect, comprising any one of the above-noted particular aspects, the daily dose comprises between 0.3 mg and 4.5 mg of (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the daily dose comprises 0.3 mg, 1.0 mg, 2.0 mg, or 3.0 mg, of (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the pharmaceutical composition comprises (R)-7-chloro-N-(quinuclidin-3-yl)benzo[b]thiophene-2-carboxamide, hydrochloride, monohydrate.

In a further particular aspect, comprising any one of the above-noted particular aspects, the pharmaceutical composition comprises between 90 wt. % and 110 wt. % of the designated 1.0 mg dosage, 2.0 mg dosage, or 3.0 mg dosage, of (R)-7-chloro-N-(quinuclidin-3-yl)benzo[b]thiophene-2-carboxamide, hydrochloride, monohydrate.

In a further particular aspect, comprising any one of the above-noted particular aspects, the pharmaceutical composition comprises 1.0 mg (R)-7-chloro-N-(quinuclidin-3-yl)benzo[b]thiophene-2-carboxamide, hydrochloride, monohydrate.

In a further particular aspect, comprising any one of the above-noted particular aspects, the pharmaceutical composition comprises 2.0 mg (R)-7-chloro-N-(quinuclidin-3-yl)benzo[b]thiophene-2-carboxamide, hydrochloride, monohydrate.

In a further particular aspect, comprising any one of the above-noted particular aspects, the pharmaceutical composition is administered in either fasted or fed mode.

In a further particular aspect, comprising any one of the above-noted particular aspects, the pharmaceutical composition is in the form of a tablet.

In a further particular aspect, comprising any one of the above-noted particular aspects, the treatment further comprises co-administering an acetylcholine esterase inhibitor.

In a further particular aspect, comprising any one of the above-noted particular aspects, the treatment comprises halting the administration of an acetylcholine esterase inhibitor prior to treating with (R)-7-chloro-N-(quinuclidin-3-yl)benzo[b]thiophene-2-carboxamide, or a pharmaceutically acceptable salt thereof.

In a further particular aspect, comprising any one of the above-noted particular aspects, the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate, polymorph form I.

In a further particular aspect, comprising any one of the above-noted particular aspects, the (R)-7-chloro-N-(quinuclidin-3-yl)benzo[b]thiophene-2-carboxamide, hydrochloride, monohydrate, is (R)-7-chloro-N-(quinuclidin-3-yl)benzo[b]thiophene-2-carboxamide, hydrochloride, monohydrate, polymorph form I.

A particular aspect of the present invention provides a method of treating a patient having a cognitive impairment, for example MCI, LCI, Alzheimer's disease, or dementia of the Alzheimer's-type, comprising: administering to the patient, for an extended period, a daily dose of a pharmaceutical composition comprising (R)-7-chloro-N-(quinuclidin-3-yl)benzo[b]thiophene-2-carboxamide, or a pharmaceutically acceptable salt thereof.

A particular aspect of the present invention provides a method of improving cognition in a patient having a cognitive impairment, for example MCI, LCI, Alzheimer's disease, or dementia of the Alzheimer's-type, comprising: administering to the patient, for an extended period, for example for at least 6, 18, 23, or 24 weeks or more, a daily dose of a pharmaceutical composition comprising (R)-7-chloro-N-(quinuclidin-3-yl)benzo[b]thiophene-2-carboxamide, or a pharmaceutically acceptable salt thereof.

A certain aspect of the present invention provides a method of treating a patient in need thereof, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I.

A certain aspect of the present invention provides a method of treating a patient in need thereof, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient in need thereof, comprising: administering to the patient, in either fasted or fed mode, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient suffering from, or diagnosed as having, a cognitive impairment, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient having a sub-normal score on at least one cognitive assessment test, for example having a score of ≥14 to ≤24 on a MMSE test or a score of ≥2 on a CDR-SB test, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient suffering from, or diagnosed as having, LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of treating a patient suffering from, or diagnosed as having, MCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of improving cognition or providing a procognitive effect in a patient suffering from, or diagnosed as having, a cognitive impairment, for example Alzheimer's disease, dementia of the Alzheimer's-type, MCI, or LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of improving cognition or providing a procognitive effect in a patient suffering from, or diagnosed as having, a cognitive impairment, for example Alzheimer's disease, dementia of the Alzheimer's-type, MCI, or LCI, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form II, comprises between 80 and 115 wt. % of the designated daily dose.

A certain aspect of the present invention provides a method of improving cognition or providing a procognitive effect in a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of improving cognition or providing a procognitive effect in a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient, for an extended period, a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose.

A certain aspect of the present invention provides a method of improving or preventing the deterioration of one or more symptoms associated with a cognitive impairment, for example Alzheimer's disease, dementia of the Alzheimer's-type, MCI, or LCI, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, the cognitive impairment.

A certain aspect of the present invention provides a method of improving or preventing the deterioration of one or more symptoms associated with Alzheimer's disease, for example mild Alzheimer's disease, moderate Alzheimer's disease, severe Alzheimer's disease, or mild-to-moderate Alzheimer's disease, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, Alzheimer's disease.

A certain aspect of the present invention provides a method of improving or preventing the deterioration of one or more symptoms associated with dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to a patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein the patient suffers from, or has been diagnosed as having, dementia of the Alzheimer's-type.

A certain aspect of the present invention provides a method of treating a patient suffering from, or diagnosed as having, a cognitive impairment, for example Alzheimer's disease, dementia of the Alzheimer's-type, MCI, or LCI, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of the cognitive impairment in said patient.

A certain aspect of the present invention provides a method of treating a patient suffering from, or diagnosed as having, Alzheimer's disease, for example mild Alzheimer's disease, moderate Alzheimer's disease, severe Alzheimer's disease, or mild-to-moderate Alzheimer's disease, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of Alzheimer's disease in said patient.

A certain aspect of the present invention provides a method of treating a patient suffering from, or diagnosed as having, dementia of the Alzheimer's-type, for example mild dementia of the Alzheimer's-type, moderate dementia of the Alzheimer's-type, severe dementia of the Alzheimer's-type, or mild-to-moderate dementia of the Alzheimer's-type, comprising: administering to the patient a tablet composed of a pharmaceutical composition comprising a designated daily dose of between 0.1 mg and 4.5 mg of (R)-7-chloro-N-(quinuclidin-3-yl)benzo[b]thiophene-2-carboxamide, hydrochloride, monohydrate, polymorph form I, for an extended period, wherein the amount of the (R)-7-chloro-N-(quinuclidin-3-yl)benzo[b]thiophene-2-carboxamide, hydrochloride, monohydrate, polymorph form I, comprises between 80 and 115 wt. % of the designated daily dose, and wherein said treating improves or prevents the deterioration of the dementia of the Alzheimer's-type in said patient.

It should be noted that for any or all of the above-noted certain aspects that the the amount of the (R)-7-chloro-N-(quinuclidin-3-yl)benzo[b]thiophene-2-carboxamide, hydrochloride, monohydrate, polymorph form I, may include between 90 and 110 wt. %, for example, between 95 wt. % and 105 wt. %, or between 97 wt. % and 103 wt. % of the designated daily dose.

It should be further noted that for any or all of the above-noted certain aspects that the designated daily dose may include an amount of between 0.7 mg and 4.3 mg of (R)-7-chloro-N-(quinuclidin-3-yl)benzo[b]thiophene-2-carboxamide, hydrochloride, monohydrate, polymorph form I, for example consist of an amount of between 0.7 mg and 3.3 mg, between 1.0 mg and 4.0 mg, between 1.0 mg and 3.0 mg, between 1.7 mg and 4.3 mg, between 2.0 mg and 4.5 mg, between 2.0 mg and 4.0 mg, between 2.0 mg and 3.0 mg, between 2.7 mg and 3.7 mg, between 3.0 mg and 4.5 mg, between 3.0 mg and 4.0 mg, or between 3.5 mg and 4.5 mg, of (R)-7-chloro-N-(quinuclidin-3-yl)benzo[b]thiophene-2-carboxamide, hydrochloride, monohydrate, polymorph form I.

It should be further noted that for any or all of the above-noted certain aspects the designated daily dose may include an amount of at least 0.1 mg to no greater than 4.5 mg, of (R)-7-chloro-N-(quinuclidin-3-yl)benzo[b]thiophene-2-carboxamide, hydrochloride, monohydrate, polymorph form I, for example consist of an amount of at least 0.1 mg to no greater than 4.5 mg, such as at least 0.7 mg, at least 1.0 mg, at least 1.3 mg, at least 1.5 mg, at least 1.7 mg, at least 2.0 mg, at least 2.3 mg, at least 2.5 mg, at least 2.7 mg, at least 3.0 mg, at least 3.3 mg, at least 3.5 mg, or at least 3.7 mg, to no greater than 4.5 mg, such as to no greater than 4.3 mg or to no greater than 4.0 mg, of (R)-7-chloro-N-(quinuclidin-3-yl)benzo[b]thiophene-2-carboxamide, hydrochloride, monohydrate, polymorph form I.

It should be further noted that for any or all of the above-noted certain aspects the designated daily dose may include an amount of at least 0.1 mg to no greater than 4.5 mg, of (R)-7-chloro-N-(quinuclidin-3-yl)benzo[b]thiophene-2-carboxamide, hydrochloride, monohydrate, polymorph form I, for example consist of an amount of 0.1 mg, 0.3 mg, 0.7 mg, 1.0 mg, 1.3 mg, 1.5 mg, 1.7 mg, 2.0 mg, 2.3 mg, 2.5 mg, 2.7 mg, 3.0 mg, 3.3 mg, 3.5 mg, 3.7 mg, 4.0 mg, 4.3 mg, or 4.5 mg, of (R)-7-chloro-N-(quinuclidin-3-yl)benzo[b]thiophene-2-carboxamide, hydrochloride, monohydrate, polymorph form I, such as consist of an amount of 0.3 mg, 0.7 mg, 1.0 mg, 1.3 mg, 1.7 mg, 2.0 mg, 2.3 mg, 2.7 mg, 3.0 mg, 3.3 mg, 3.7 mg, 4.0 mg, or 4.3 mg, of (R)-7-chloro-N-(quinuclidin-3-yl)benzo[b]thiophene-2-carboxamide, hydrochloride, monohydrate, polymorph form I, for example, consist of an amount of 1.0 mg, 2.0 mg, 3.0 mg, 4.0 mg, or 4.5 mg, of (R)-7-chloro-N-(quinuclidin-3-yl)benzo[b]thiophene-2-carboxamide, hydrochloride, monohydrate, polymorph form I.

It should be further noted that for any or all of the above-noted certain aspects that the extended period may include at least 6 weeks, for example 8 weeks or more, 12 weeks or more, 16 weeks or more, 17 weeks or more, 18 weeks or more, 23 weeks or more, 24 weeks or more, 30 weeks or more, 36 weeks or more, 42 weeks or more, 48 weeks or more, or 52 weeks or more.

Pharmaceutical Compositions (R)-7-chloro-N-(quinuclidin-3-yl)benzo[b]thiophene-2-carboxamide, or a pharmaceutically acceptable salt thereof, may be formulated for administration in solid or liquid form. For example, (R)-7-chloro-N-(quinuclidin-3-yl)benzo[b]thiophene-2-carboxamide, or a pharmaceutically acceptable salt thereof, may be formulated for administration in a capsule, a tablet, or a powder form. For example, (R)-7-chloro-N-(quinuclidin-3-yl)benzo[b]thiophene-2-carboxamide, or a pharmaceutically acceptable salt thereof, may be formulated alone or as part of a pharmaceutical composition, suitable for oral administration, such as in a capsule or tablet, intravenous administration, parenteral administration, topical administration, or transdermal administration, such as in a patch, to a patient in need thereof.

(R)-7-chloro-N-(quinuclidin-3-yl)benzo[b]thiophene-2-carboxamide, or a pharmaceutically acceptable salt thereof, may be administered as a pharmaceutical composition, for example, in the presence of carriers, adjuvants, excipients, diluents, fillers, buffers, stabilizers, preservatives, lubricants, and the like, for example, administered as a pharmaceutical composition (e.g., formulation) comprising at least (R)-7-chloro-N-(quinuclidin-3-yl)benzo[b]thiophene-2-carboxamide, or a pharmaceutically acceptable salt thereof, together with one or more pharmaceutically acceptable carriers, adjuvants, excipients, diluents, or other materials well known to those skilled in the art. As used herein, the term "pharmaceutically acceptable", unless otherwise specified, includes the generally accepted meaning which encompasses combinations, compounds, materials, compositions, and/or dosage forms which are, within the scope of sound medical judgment, suitable for consumption by humans without excessive toxicity, irritation, allergic response, or other problem or complication, commensurate with a reasonable benefit/risk ratio.

Suitable pharmaceutically acceptable carriers, excipients, and diluents, can include, but are not limited to, lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include, but are not limited to, pharmaceutically acceptable lubricating agents, glidants, wetting agents, emulsifying and suspending agents, preserving agents, sweetening agents, and/or flavoring agents. The pharmaceutical compositions of the present invention may be formulated so as to provide quick release, immediate release, sustained release, or delayed release of (R)-7-chloro-N-(quinuclidin-3-yl)benzo[b]thiophene-2-carboxamide, or a pharmaceutically acceptable salt thereof, after administration to the patient by employing procedures well-known in the art.

Another embodiment of the invention further comprises methods of making Pharmaceutical Composition, comprising admixing at least (R)-7-chloro-N-(quinuclidin-3-yl)benzo[b]thiophene-2-carboxamide, or a pharmaceutically acceptable salt thereof, together with one or more pharmaceutically acceptable carriers, excipients, buffers, adjuvants, stabilizers, or other materials.

EXAMPLES

Test Compound refers to (R)-7-chloro-N-(quinuclidin-3-yl)benzo[b]thiophene-2-carboxamide, hydrochloride, monohydrate—Polymorph Form I.

Test Composition refers to the capsule formulation that was manufactured in strengths of 0.3 mg, 1 mg, or 2 mg of the Test Compound provided, exclusive of excipients or additives, in capsules (light blue, opaque, size No. 2, hard gelatin capsules).

Example 1

Clinical Study in Subjects with Mild-to-Moderate Alzheimer's Disease

A double-blind study of 3 doses of the Test Composition or placebo in subjects with mild-to-moderate Alzheimer's disease, with or without receiving a concomitant AChEI for 24 weeks (168 days) after a 7 day placebo run-in period.

Total number of subjects in the safety population was 409 subjects that were dosed once-daily with a dosing-capsule for a period of 168 days. The subjects dosed, and the particular dosing, included: 104 subjects dosed with Placebo capsule; and 305 subjects dosed with Test Compound (104 subjects with 0.3 mg capsules; 101 subjects with 1 mg capsules; and 100 subjects with 2 mg capsules).

The population included generally healthy male or female subjects, aged 50 to ≤85 years, with mild-to-moderate Alzheimer's disease, consistent with criteria defined by a Work Group of the National Institute of Neurological and Communicative Disorders and Stroke—Alzheimer's Disease and Related Disorders Association, of mild to moderate severity, with a Mini-Mental State Examination score (MMSE) 14 and ≤24, and a Clinical Dementia Rating Scale Sum of the Boxes (CDR-SB) score of 2. Subjects were required to have a reliable caregiver who, if not living in the household, had an interaction with the subject at least 4 times per week. Subjects were required to be either receiving a stable dose of an AChEI (donepezil or rivastigmine) for at least 3 months before screening or not presently being treated with an AChEI or memantine for at least 30 days.

Subject Demographics: The mean age of subjects in the safety population was 71.9 years (range: 50-85 years), predominately female (54.3%), 96.8% were White, and 52.6% were not receiving an AChEI medication at baseline, while 47.4% were receiving a concomitant AChEI medication at baseline (13.2% rivastigmine and 34.2% donepezil).

The efficacy endpoint was determined by one or more of the following: ADAS-cog-13 (Alzheimer's Disease Assessment Scale, 13-item subscale), ADAS-cog-11 (11-item subscale), COWAT (Controlled Word Association Test), CFT (Category Fluency Test), CDR-SB (Clinical Dementia Rating Scale Sum of Boxes), NPI (Neuropsychiatric Inventory), MMSE (Mini-Mental State Examination), ADCS-ADL (Alzheimer's Disease Cooperative Study-Activities of Daily Living), and Composite Scores for Cognition, Memory, and Executive Function. In addition, the plasma levels of the Test Compound in the particular subject were measured.

Characterization of the subjects included in the study are presented in Table 1 (Subject Disposition), Table 2 (Demographics), and Table 3 (Baseline; Intention-To-Test (ITT) Population):

TABLE 1

Subject Disposition

| | Test Compound | | | | |
|---|---|---|---|---|---|
| Status | 0.3 mg n (%) | 1 mg n (%) | 2 mg n (%) | Placebo n (%) | Total n (%) |
| Screened | | | | | 499 |
| Screen Failures | | | | | 90 |
| Prior to Day −7 | | | | | 75 |
| Run-in | | | | | 15 |
| Randomized | 104 | 101 | 100 | 104 | 409 |
| Completed Day 28 | 98 (94.2) | 95 (94.1) | 92 (92.0) | 96 (92.3) | 381 (93.2) |
| Completed Study | 86 (82.7) | 81 (80.2) | 78 (78.0) | 81 (77.9) | 326 (79.7) |
| Discontinued Early | 18 (17.3) | 20 (19.8) | 22 (22.0) | 23 (22.1) | 83 (20.3) |

TABLE 2

Demographics

| | Test Compound | | | | |
|---|---|---|---|---|---|
| | 0.3 mg N = 104 | 1 mg N = 101 | 2 mg N = 100 | Placebo N = 104 | Total N = 409 |
| Gender, n(%) | | | | | |
| Male | 55 (52.9) | 43 (42.6) | 43 (43.0) | 46 (44.2) | 187 (45.7) |
| Female | 49 (47.1) | 58 (57.4) | 57 (57.0) | 58 (55.8) | 222 (54.3) |
| Race, n (%) | | | | | |
| White | 99 (95.2) | 97 (96.0) | 97 (97.0) | 103 (99.0) | 396 (96.8) |
| Black | 4 (3.8) | 2 (2.0) | 0 | 1 (1.0) | 7 (1.7) |
| Asian | 3 (1.0) | 1 (1.0) | 1 (1.0) | 0 | 3 (0.7) |
| Am. Indian | 0 | 1 (1.0) | 0 | 0 | 1 (0.2) |
| Other | 0 | 0 | 2 (2.0) | 0 | 2 (0.5) |
| Ethnicity, n (%) | | | | | |
| Hispanic | 10 (9.6) | 11 (10.9) | 14 (14.0) | 11 (10.6) | 46 (11.2) |
| Not Hispanic | 94 (90.4) | 90 (89.1) | 86 (86.0) | 93 (89.4) | 363 (88.8) |
| Age (years) | | | | | |
| Mean ± SD | 72.5 ± 8.31 | 73.0 ± 8.20 | 71.4 ± 8.92 | 70.7 ± 9.14 | 71.9 ± 8.67 |
| Median | 73.0 | 74.0 | 71.5 | 72.0 | 73.0 |
| Range | 52-85 | 50-85 | 50-85 | 50-85 | 50-85 |
| BMI (kg/m$^2$ at baseline) n | N = 103 | N = 101 | N = 100 | N = 104 | N = 408 |
| Mean ± SD | 26.5 ± 4.42 | 26.7 ± 4.19 | 26.7 ± 4.72 | 26.1 ± 3.53 | 26.5 ± 4.22 |
| Median | 25.9 | 26.7 | 26.1 | 25.7 | 26.0 |
| Range | 19.2-41.6 | 15.3-39.7 | 18.5-47.8 | 17.0-34.7 | 15.3-47.8 |
| Smoking/Tobacco n (%) | | | | | |
| Yes | 7 (6.7) | 8 (7.9) | 10 (10.0) | 9 (8.7) | 34 (8.3) |
| No | 97 (93.3) | 93 (92.1) | 90 (90.0) | 95 (91.3) | 375 (91.7) |

TABLE 2-continued

Demographics

|  | Test Compound | | | | |
| --- | --- | --- | --- | --- | --- |
|  | 0.3 mg<br>N = 104 | 1 mg<br>N = 101 | 2 mg<br>N = 100 | Placebo<br>N = 104 | Total<br>N = 409 |
| Continent, n (%) | | | | | |
| US | 62 (59.6) | 62 (61.4) | 63 (63.0) | 63 (60.6) | 250 (61.1) |
| Europe | 42 (40.4) | 39 (38.6) | 37 (37.0) | 41 (39.4) | 159 (38.9) |
| AChEI, n (%) | | | | | |
| Add-on | 47 (45,2) | 47 (46.5) | 50 (50.0) | 50 (48.1) | 194 (47.4) |
| De-novo | 57 (54.8) | 54 (53.5) | 50 (50.0) | 54 (51.9) | 215 (52.6) |

TABLE 3

Baseline; Intention-To-Test (ITT) Population

| Baseline | | Test Compound | | | |
| --- | --- | --- | --- | --- | --- |
| | | 0.3 mg | 1 mg | 2 mg | Placebo |
| ADAS-cog-13 | N | 98 | 95 | 92 | 96 |
| (higher is more severe) | Mean (SD) | 34.7 (13.28) | 32.1 (11.89) | 33.5 (12.65) | 33.3 (11.45) |
| Possible Range: 0-85 | Min-Max | 7-65 | 7-63 | 10-68 | 9-63 |
| ADAS-cog-11 | N | 98 | 95 | 92 | 96 |
| (higher is more severe) | Mean (SD) | 24.3 (10.89) | 22.0 (9.84) | 23.0 (10.28) | 23.3 (9.64) |
| Possible Range: 0-70 | Min-Max | 6-50 | 5-50 | 7-53 | 6-50 |
| CDR-SB | N | 98 | 94 | 92 | 96 |
| (higher is more severe) | Mean (SD) | 6.3 (3.02) | 6.1 (2.74) | 6.0 (2.91) | 6.0 (2.92) |
| Possible Range: 0-18 | Min-Max | 2-16 | 3-13 | 2-14 | 1-14 |
| COWAT | N | 98 | 95 | 92 | 96 |
| (lower is more severe) | Mean (SD) | 21.6 (11.69) | 22.3 (11.44) | 20.5 (11.12) | 22.9 (12.09) |
| Possible Range: 0-144 | Min-Max | 4-64 | 5-59 | 3-53 | 0-66 |
| CFT | N | 98 | 95 | 92 | 96 |
| (lower is more severe) | Mean (SD) | 9.6 (5.15) | 9.6 (4.46) | 9.3 (4.44) | 8.8 (4.23) |
| | Min-Max | 1-24 | 2-21 | 0-21 | 0-22 |
| ADCS-ADL | N | 98 | 95 | 92 | 96 |
| (lower is more severe) | Mean (SD) | 54.6 (15.10) | 55.6 (13.97) | 54.2 (15.39) | 55.1 (13.99) |
| Possible Range: 0-78 | Min-Max | 5-76 | 10-77 | 6-77 | 7-77 |
| NPI | N | 92 | 86 | 85 | 88 |
| (higher is more severe) | Mean (SD) | 7.7 (10.44) | 6.6 (8.81) | 5.2 (6.55) | 6.9 (9.51) |
| Possible Range: 0-120 | Min-Max | 0-57 | 0-41 | 0-40 | 0-54 |
| MMSE | N | 98 | 95 | 92 | 96 |
| (lower is more severe) | Mean (SD) | 20.4 (3.79) | 20.5 (3.93) | 20.5 (3.57) | 20.6 (3.28) |
| Possible Range: 0-30 | Min-Max | 12-28 | 11-29 | 11-28 | 12-27 |

Subjects with mild to moderate Alzheimer's disease receiving stable treatment with an AChEI (donepezil or rivastigmine: 'add-on' subjects) or not receiving an AChEI (de novo subjects') received 0.3, 1, or 2 mg doses of Test Composition or placebo for up to 24 weeks (168 days) of double-blind treatment, after a 7-day single-blind, placebo run-in period to assess study drug compliance. A follow-up telephone contact was conducted approximately 15 days after the last dose of study drug for questions regarding safety. An overview of the results, comparing the 2 mg dosing of Test Compound versus placebo, and providing the effect size (with P-values) and a list of the figures that provide a further presentation of this data is presented in Table 4:

TABLE 4

Test Compound (2 mg dose) versus Placebo

| Measure | Effect Size | P-value | Figure |
| --- | --- | --- | --- |
| ADAS-Cog 13 | 0.39 | p = 0.0189 | 1 |
| ADAS-Cog 11 | 0.34 | p = 0.0151 | 2 |
| CDR-SB | 0.31 | p = 0.0253 | 3 |
| COWAT | 0.35 | p = 0.0135 | |
| MMSE | 0.21 | p = 0.0955 | 4 |
| ADCS-ADL | 0.20 | p = 0.0925 | 5 |

TABLE 5

Test Compound versus Placebo, via ADAS-Cog-13 (Baseline was assigned the value of zero @ Week 0)

| Test Compound daily dose | Week 4 | Week 12 | Week 18 | Week 23 |
| --- | --- | --- | --- | --- |
| 0.3 mg | −0.615 | −0.5876 | −0.3132 | 0.0915 |
| 1 mg | −0.8012 | −1.2029 | −0.3222 | −0.0565 |
| 2 mg | −0.0185 | −1.4328 | −1.6593 | −1.6899 |
| Placebo | −0.3366 | −0.9492 | −0.1705 | 0.3957 |

TABLE 6

Test Compound versus Placebo, via ADAS-Cog-11 (Baseline was assigned the value of zero @ Week 0)

| Test Compound daily dose | Week 4 | Week 12 | Week 18 | Week 23 |
|---|---|---|---|---|
| 0.3 mg | −0.3534 | −0.2129 | −0.067 | 0.2755 |
| 1 mg | −0.3412 | −0.8317 | 0.1063 | 0.3534 |
| 2 mg | −0.0031 | −0.998 | −1.1519 | −1.1188 |
| Placebo | −0.1468 | −0.8284 | −0.1028 | 0.4414 |

TABLE 7

Test Compound versus Placebo, via CDR-SB (Baseline was assigned the value of zero @ Week 0)

| Test Compound daily dose | Week 4 | Week 12 | Week 18 | Week 23 |
|---|---|---|---|---|
| 0.3 mg | 0.0026 | 0.0542 | 0.2325 | 0.4427 |
| 1 mg | −0.2365 | −0.0811 | −0.0424 | 0.1214 |
| 2 mg | −0.1361 | −0.1352 | −0.1368 | −0.088 |
| Placebo | −0.1163 | 0.0363 | 0.1572 | 0.2879 |

TABLE 8

Test Compound versus Placebo, via MMSE (Baseline was assigned the value of zero @ Week 0)

| Test Compound daily dose | Week 4 | Week 12 | Week 18 | Week 23 |
|---|---|---|---|---|
| 0.3 mg | −0.0411 | 0.185 | −0.3601 | −0.3112 |
| 1 mg | 0.9142 | 0.7836 | 0.7253 | 0.4416 |
| 2 mg | 0.5262 | 0.3526 | 0.723 | 0.5139 |
| Placebo | 0.2512 | 0.0096 | −0.1073 | 0.0005 |

TABLE 9

Test Compound versus Placebo, via ADCS-ADL (Baseline was assigned the value of zero @ Week 0)

| Test Compound daily dose | Week 4 | Week 12 | Week 18 | Week 23 |
|---|---|---|---|---|
| 0.3 mg | 0.07926 | −0.5757 | −0.6255 | −1.8992 |
| 1 mg | 0.509 | 0.9138 | 0.8306 | −0.3467 |
| 2 mg | 0.908 | 0.8426 | 0.8097 | 0.3166 |
| Placebo | −0.2638 | −0.5036 | 0.02966 | −0.4293 |

Significant positive effects were observed for both de novo treatment and add-on groups with a stronger effect observed in the de novo patients. A dose response relationship was observed, in comparing the 0.3 mg, 1.0 mg, and 2.0 mg treatment groups.

Prespecified Secondary Cognition Analyses:

These analyses were prespecified in the analytical plan (ITT population), and included the following: Cognition composite score (ADAS-cog Word Recall, Word Recognition, & Orientation, and COWAT and CFT), Memory composite score (ADAS-cog Word Recall, Word Recognition, and Orientation), and Executive Function composite score (COWAT and CFT). Table 10, presents an overview of these prespecified analyses, comparing the 2 mg dosing (and the 1 mg dosing for the Executive Function Composite Score) of Test Compound versus placebo, over a 23 week period, the effect size (with P-values) were observed, and lists the figures providing a further presentation of this data:

TABLE 10

Prespecified Secondary Cognition Analyses

| Measure (Test Compound Dose) | Effect Size | P-value | Figure |
|---|---|---|---|
| Cognition composite score (2 mg) | 0.42 | p = 0.0037 | 6 |
| Memory composite score (2 mg) | 0.37 | p = 0.0088 | 7 |
| Executive function composite score (2 mg) | 0.27 | p = 0.0427 | 8 |
| Executive function composite score (1 mg) | 0.32 | p = 0.0207 | 8 |

Tables 11-13 present the results comparing the Test Compound versus Placebo according to the Cognition composite score (Table 11), Memory composite score (Table 12), and Executive Function composite score (Table 13):

TABLE 11

Test Compound versus Placebo, via Cognition Composite Score (Baseline was assigned the value of zero @ Week 0)

| Test Compound daily dose | Week 4 | Week 12 | Week 18 | Week 23 |
|---|---|---|---|---|
| 0.3 mg | 0.0036 | 0.0171 | −0.0245 | −0.0451 |
| 1 mg | 0.0042 | 0.0804 | −0.0102 | 0.0287 |
| 2 mg | −0.0084 | 0.0513 | 0.0915 | 0.1276 |
| Placebo | 0.0174 | 0.0562 | −0.0178 | −0.0708 |

TABLE 12

Test Compound versus Placebo, via Memory Composite Score (Baseline was assigned the value of zero @ Week 0)

| Test Compound daily dose | Week 4 | Week 12 | Week 18 | Week 23 |
|---|---|---|---|---|
| 0.3 mg | −0.0084 | −0.0108 | −0.0294 | −0.0645 |
| 1 mg | −0.0062 | 0.08 | −0.0456 | 0.0113 |
| 2 mg | −0.0032 | 0.1021 | 0.117 | 0.169 |
| Placebo | 0.031 | 0.0912 | −0.0058 | −0.0459 |

TABLE 13

Test Compound versus Placebo, via Executive Function Composite Score (Baseline was assigned the value of zero @ Week 0)

| Test Compound daily dose | Week 4 | Week 12 | Week 18 | Week 23 |
|---|---|---|---|---|
| 0.3 mg | 0.0074 | 0.0391 | −0.0224 | −0.0153 |
| 1 mg | 0.0202 | 0.0609 | 0.0418 | 0.0476 |
| 2 mg | −0.0311 | −0.0452 | 0.0188 | 0.0244 |
| Placebo | −0.0169 | −0.0274 | −0.0455 | −0.1048 |

Figure 9A:
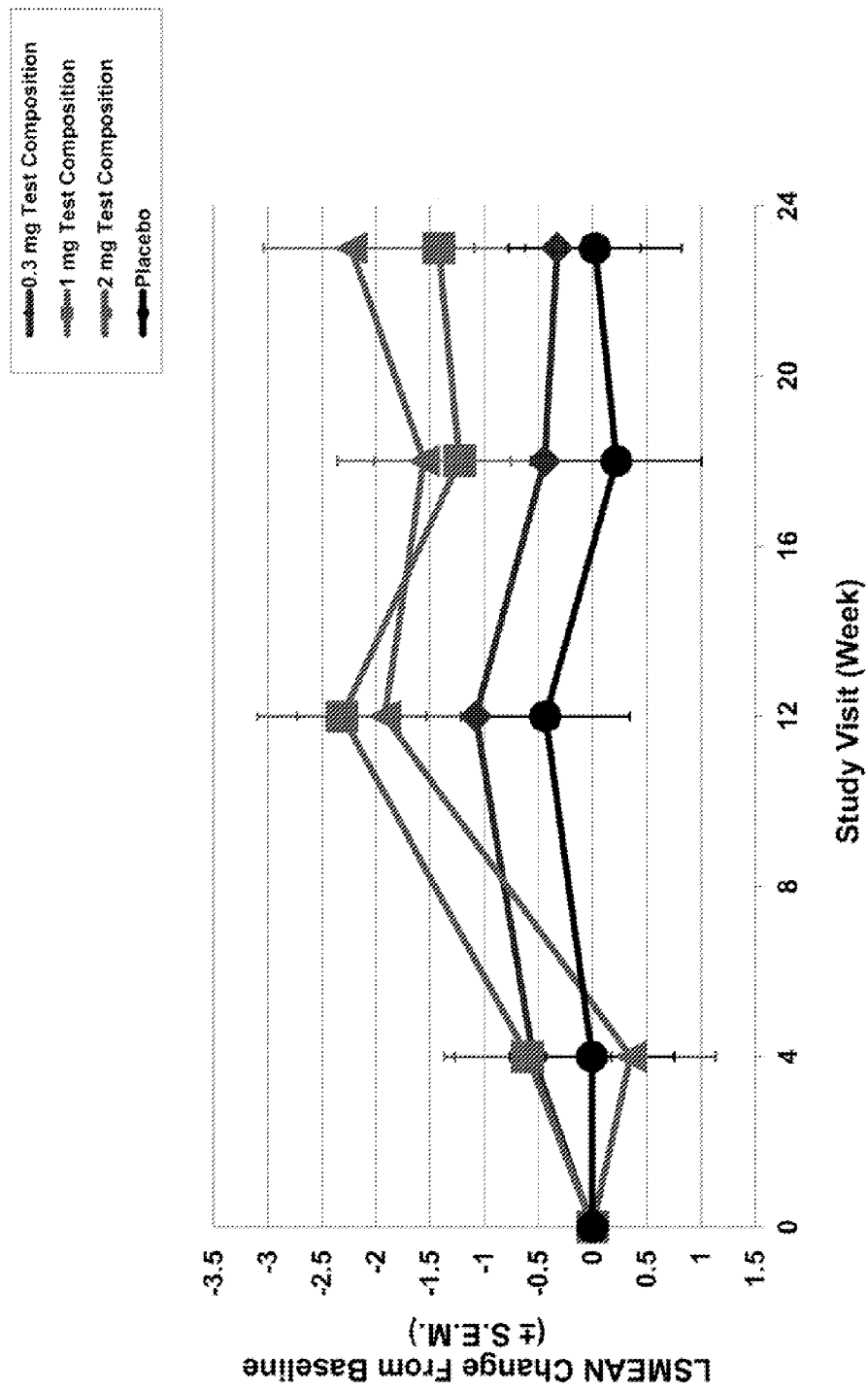
FIGS. 9A and 9B: is graphs of the results from the clinical study of Example 1 Comparing "de novo subjects" (FIG. 9A) with "add-on subjects" (FIG. 9B) for Alzheimer's Disease Assessment Scale Cog-13 (ADAS Cog-13).
Figure 9B:
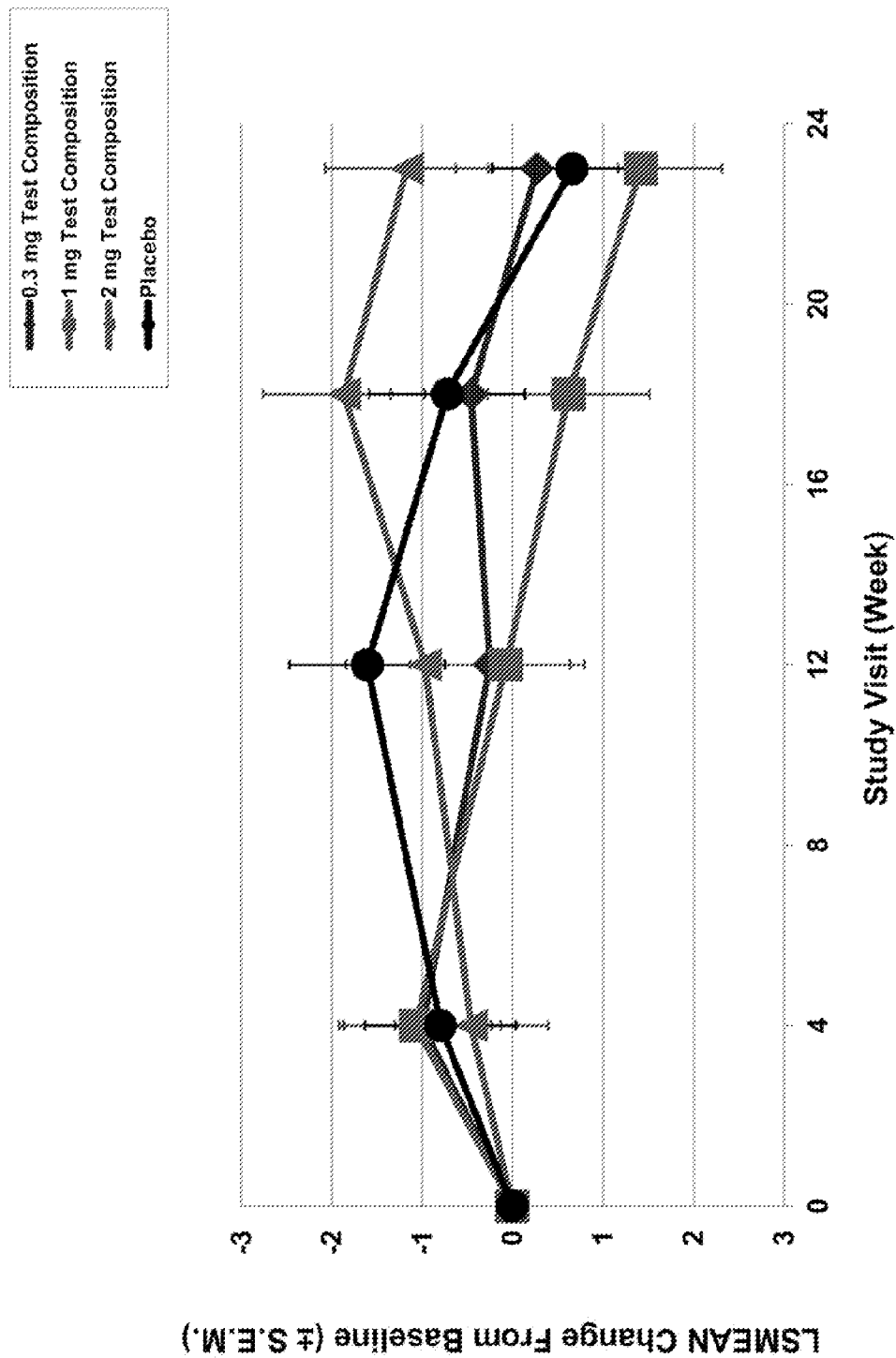
Figure 10A:
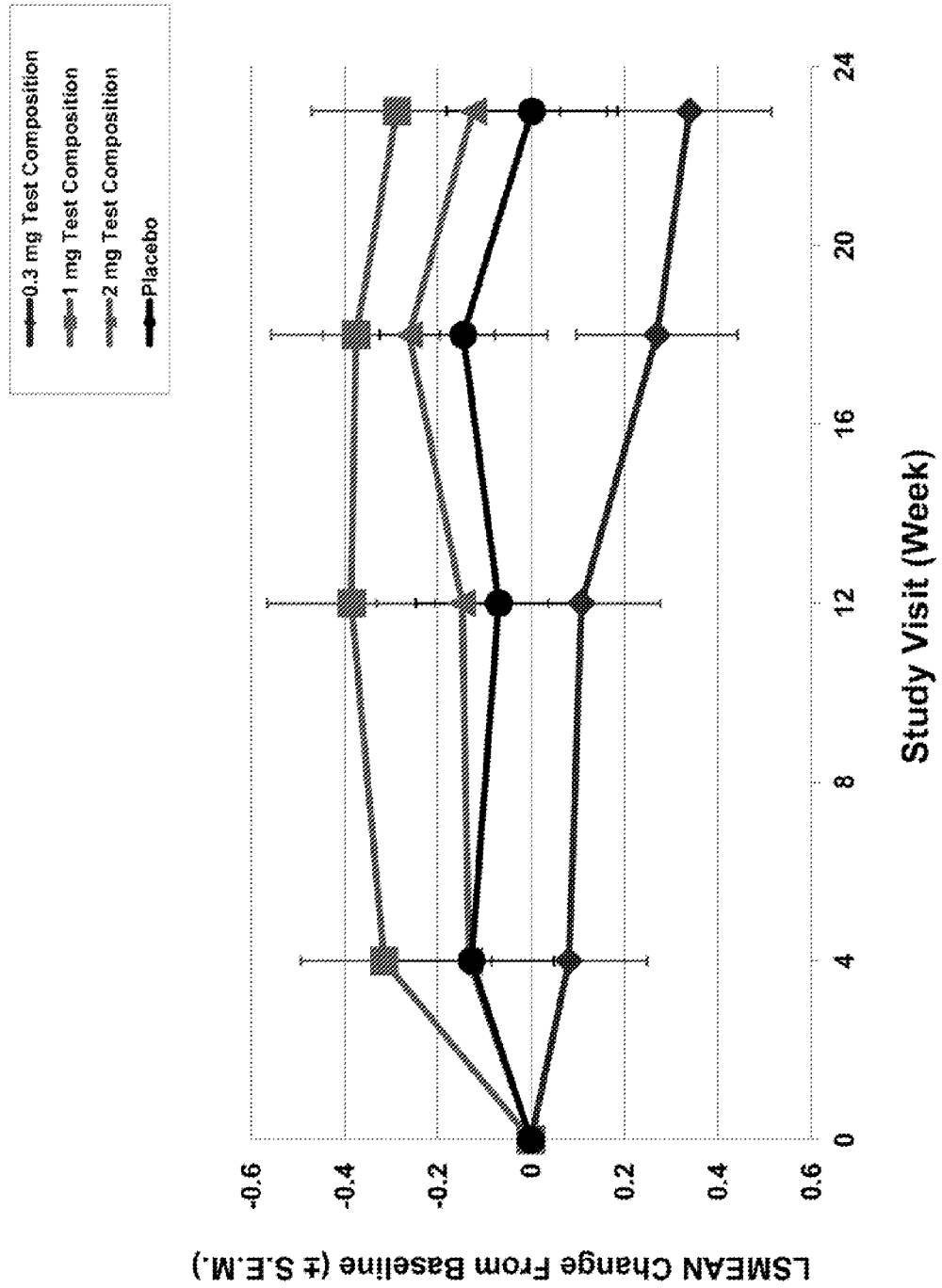
FIGS. 10A and 10B: is graphs of the results from the clinical study of Example 1 Comparing "de novo subjects" (FIG. 10A) with "add-on subjects" (FIG. 10B) for Clinical Dementia Rating-Sum of Boxes (CDR-SB).
Figure 10B:
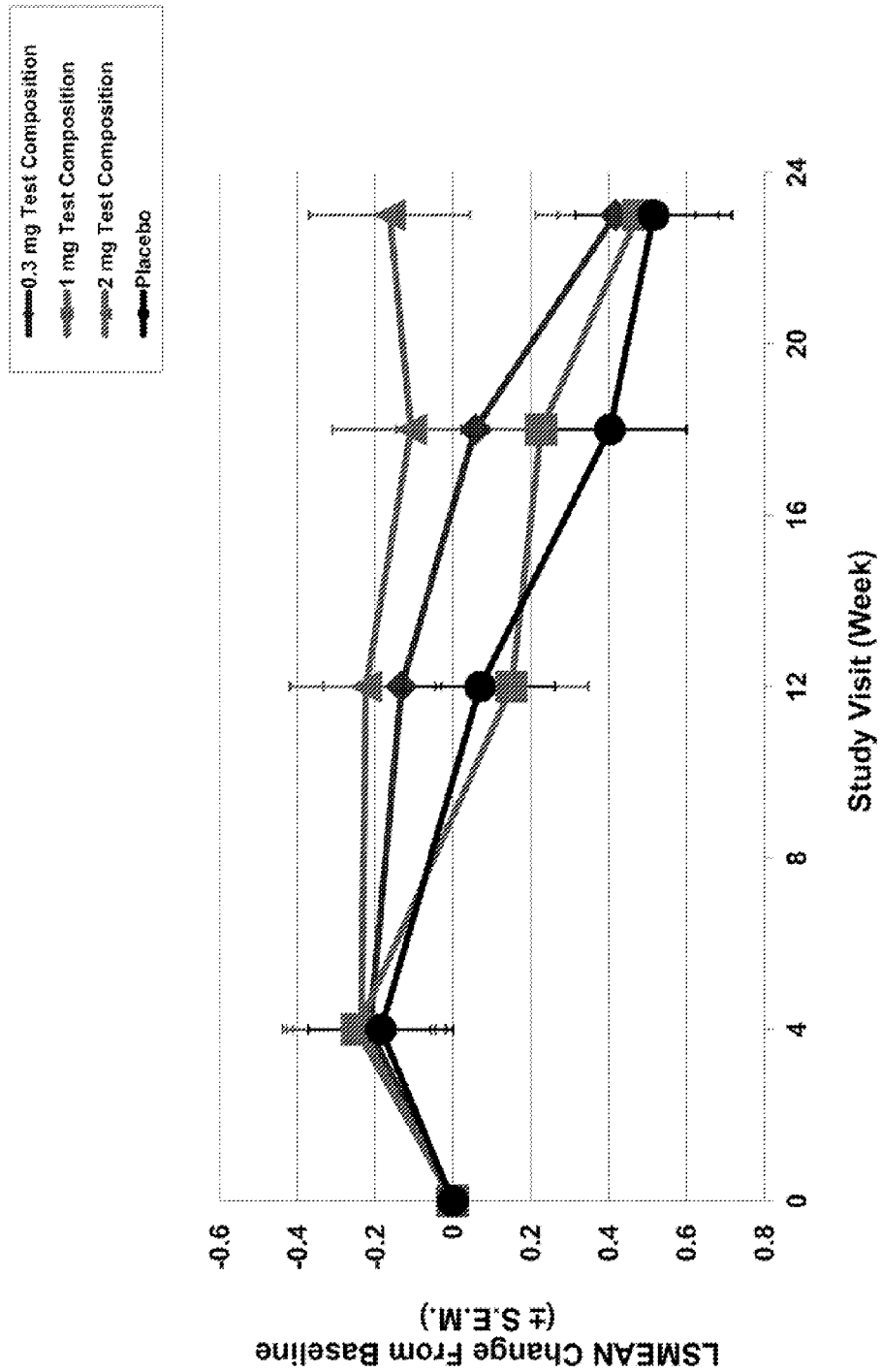

De Novo versus "Add-On" Treatment:

The "de novo subjects" (FIG. 9A) were further compared to the "add-on" subjects (FIG. 9B) (e.g., receiving a stable treatment of either donepezil or rivastigmine) via the ADAS Cog-13 test (results presented in Tables 14 and 15). Additionally, the "de novo subjects" (FIG. 10A) were further compared to the "add-on" subjects (FIG. 10B) via the CDR-SB test (results presented in Tables 16 and 17).

TABLE 14

"de novo" Patients Treated with Test Compound versus Placebo, via ADAS-Cog-13 (Baseline was assigned the value of zero @ Week 0)

| Test Compound daily dose | Week 4 | Week 12 | Week 18 | Week 23 |
|---|---|---|---|---|
| 0.3 mg | −0.545 | −1.0759 | −0.4416 | −0.3226 |
| 1 mg | −0.5942 | −2.311 | −1.2239 | −1.4169 |
| 2 mg | 0.3542 | −1.9196 | −1.5539 | −2.2283 |
| Placebo | −0.0036 | −0.433 | 0.2225 | 0.0251 |

TABLE 15

"Add-On" Patients Treated with Test Compound versus Placebo, via ADAS- Cog-13 (Baseline was assigned the value of zero @ Week 0)

| Test Compound daily dose | Week 4 | Week 12 | Week 18 | Week 23 |
|---|---|---|---|---|
| 0.3 mg | −0.9985 | −0.2474 | −0.4557 | 0.2752 |
| 1 mg | −1.0728 | −0.0705 | 0.6239 | 1.4205 |
| 2 mg | −0.455 | −0.9708 | −1.8659 | −1.1679 |
| Placebo | −0.797 | −1.6077 | −0.722 | 0.6611 |

TABLE 16

"de novo" Patients Treated with Test Compound versus Placebo, via CDR-SB (Baseline was assigned the value of zero @ Week 0)

| Test Compound daily dose | Week 4 | Week 12 | Week 18 | Week 23 |
|---|---|---|---|---|
| 0.3 mg | 0.0816 | 0.1082 | 0.27 | 0.3392 |
| 1 mg | −0.3161 | −0.3858 | −0.3763 | −0.288 |
| 2 mg | −0.133 | −0.1475 | −0.2625 | −0.1239 |
| Placebo | −0.1272 | −0.0689 | −0.1453 | 0.0018 |

TABLE 17

"Add-On" Patients Treated with Test Compound versus Placebo, via CDR-SB (Baseline was assigned the value of zero @ Week 0)

| Test Compound daily dose | Week 4 | Week 12 | Week 18 | Week 23 |
|---|---|---|---|---|
| 0.3 mg | −0.2148 | −0.1333 | 0.0576 | 0.4174 |
| 1 mg | −0.2473 | 0.1511 | 0.2268 | 0.476 |
| 2 mg | −0.236 | −0.2247 | −0.1084 | −0.1633 |
| Placebo | −0.1858 | 0.0703 | 0.4033 | 0.5153 |

Figure 11:
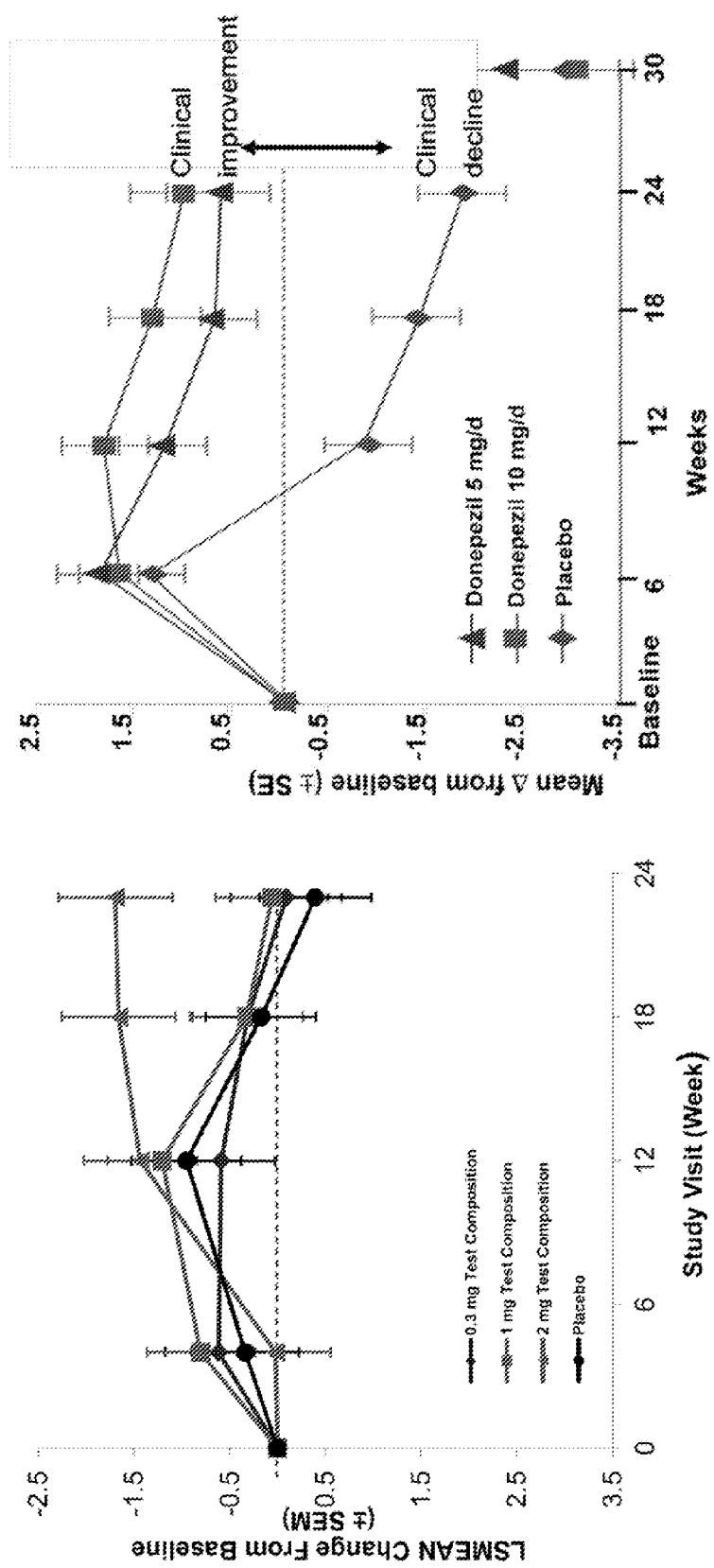
FIG. 11: is a graph of the results from the clinical study of Example 1 for Alzheimer's Disease Assessment Scale Cog-13 (ADAS Cog-13) with clinical study results of Donepezil for Alzheimer's Disease Assessment Scale Cog (ADAS Cog).

Test Compositions Versus Previous Donepezil Clinical Trial:

FIG. 11 presents the de novo subjects that received a Test Composition treatment compared to subjects treated with Donepezil according to the ADAS Cog-13 test (results presented in Table 18).

TABLE 18

Test Compound Phase 2b Improvement versus Placebo, via ADAS-Cog-13 (Baseline was assigned the value of zero @ Week 0)

| Test Compound daily dose | Week 4 | Week 12 | Week 18 | Week 23 |
|---|---|---|---|---|
| 0.3 mg | −0.615 | −0.5876 | −0.3132 | 0.0915 |
| 1 mg | −0.8012 | −1.2029 | −0.3222 | −0.0565 |
| 2 mg | −0.0185 | −1.4328 | −1.6593 | −1.6899 |
| Placebo | −0.3366 | −0.9492 | −0.1705 | 0.3957 |

Figure 12:
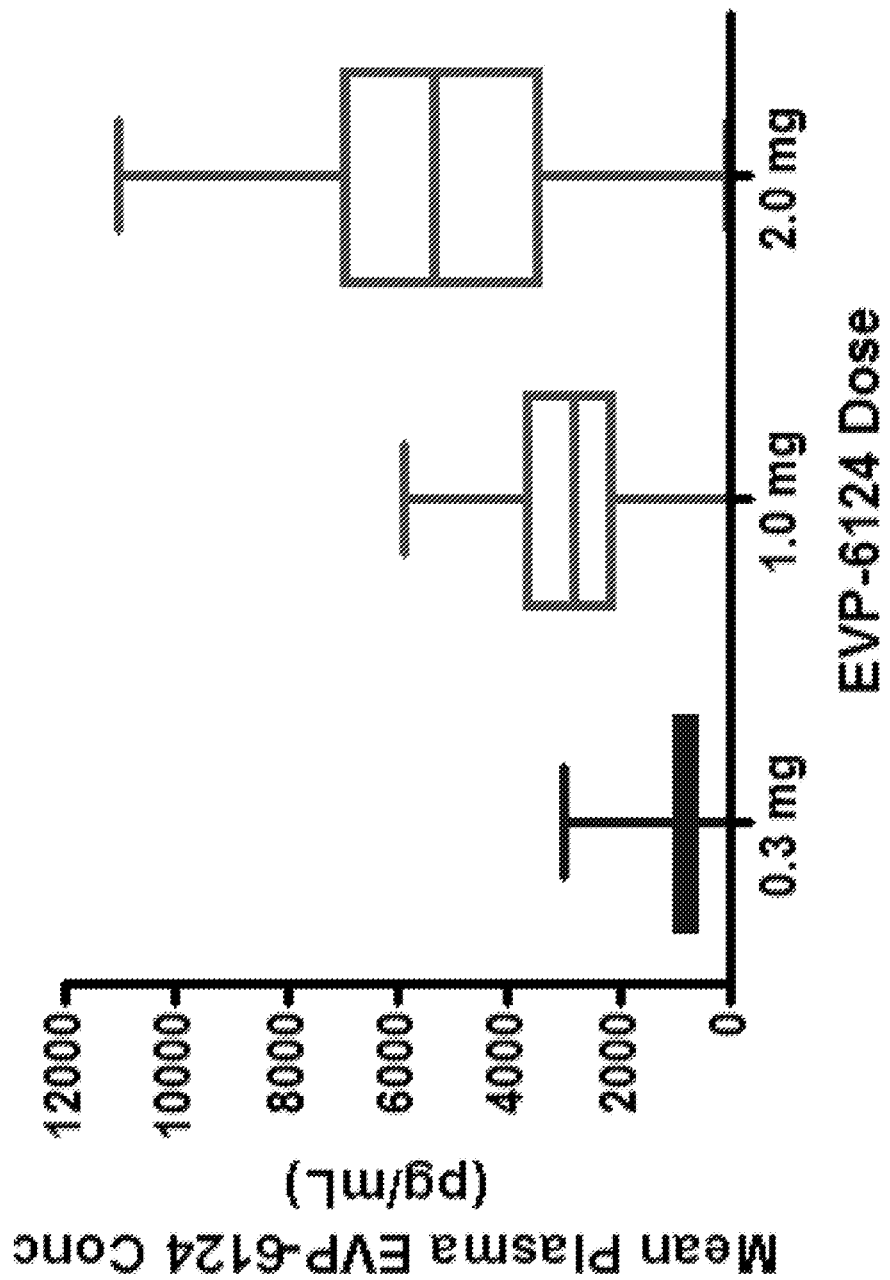
FIG. 12: is a graph of the results from the clinical study of Example 1 for Mean Plasma Concentration Levels at various daily doses.
Figure 13:
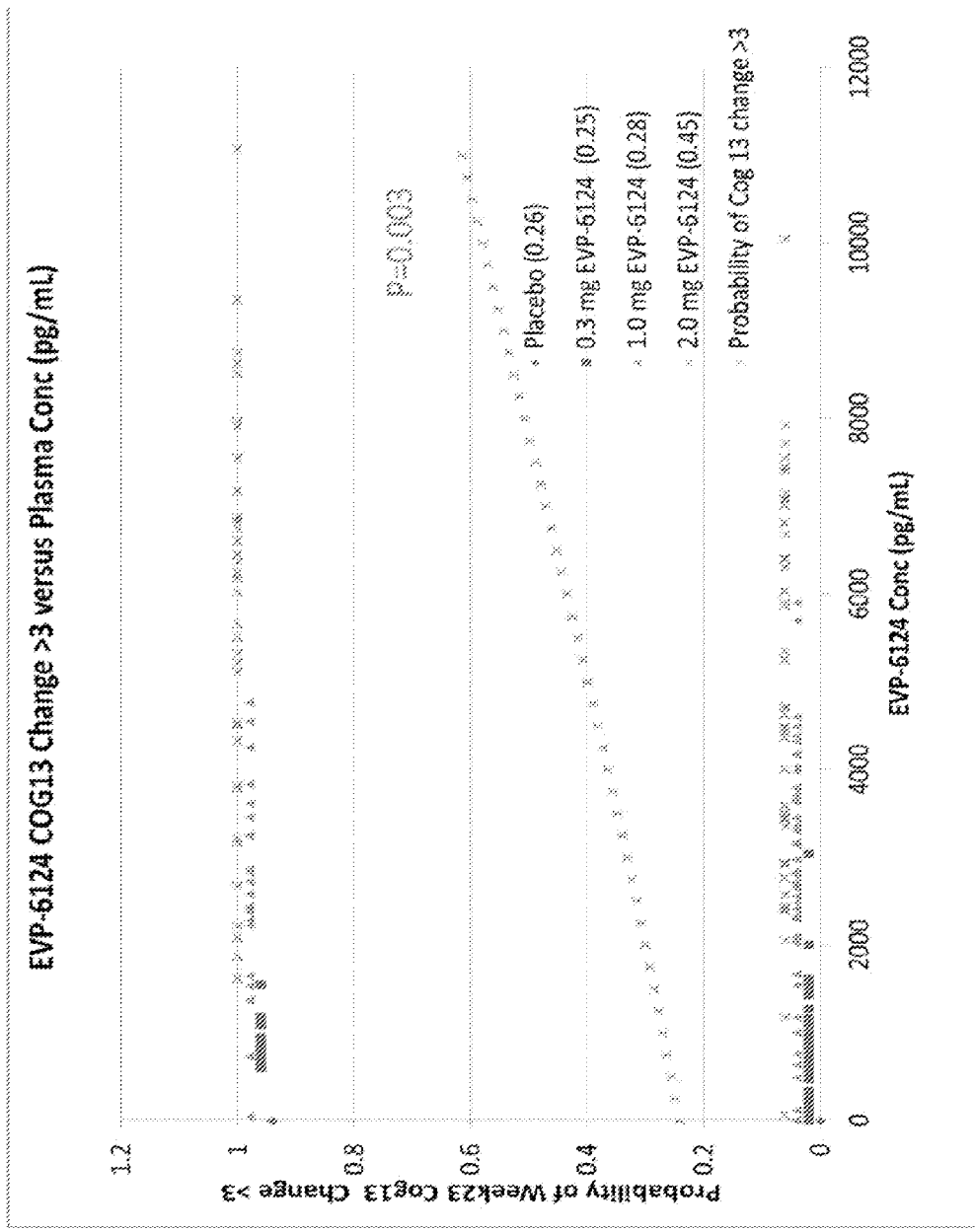
FIG. 13: is a graph of the results from the clinical study of Example 1 comparing Alzheimer's Disease Assessment Scale Cog-13 (ADAS Cog-13) with plasma concentration levels.

Responder Analysis: PK/PD Effects:

The response by plasma level of Test Compound was also investigated. A 'responder' definition of >3 pt ADAS-Cog effect was utilized. The plasma levels of responders and nonresponders informed a logistic regression model. A significant relationship (p=0.003) in plasma level and likelihood of being a responder was observed, suggesting that a significant plasma level/exposure response relationship exists for Test Compound. FIG. 12 illustrates the mean plasma concentration levels (including the 95% confidence levels and the measured extremes) of Test Compound, and FIG. 13 illustrates the Exposure Response analysis, using plasma concentration levels of Test Compound and ADAS-Cog-13 changes. The relationship between dose and likelihood of clinical response, as defined by either an ADAS-Cog effect ≥3 points, or ≥2 points, is summarized in Table 19:

TABLE 19

Responder Analysis

| | | Test Compound | | |
|---|---|---|---|---|
| Responder Definition | Placebo (%) | 0.3 mg (%) | 1 mg (%) | 2 mg (%) |
| ADAS-Cog (≥2 points) | 33% | 31% | 33% | 51% |
| ADAS-Cog (≥3 points) | 26% | 25% | 28% | 45% |

The ADAS-Cog (≥3 points) results were evaluated via a logistic regression analysis, and a significant effect was observed when comparing against placebo (p 0.0034), and these results were not affected by age, baseline severity, continent or baseline treatment (i.e., "add-on" vs. "de novo" treatment).

Testing Methods:

Cognitive Part of the Alzheimer's Disease Assessment Scale (ADAS-Cog-11)

The ADAS-cog-11 test employed herein is based on the procedure developed in the adapted version of the Administration and Scoring Manual for the Alzheimer's Disease Assessment Scale, 1994 Revised Edition, Richard C. Mohs, Ph.D., © 1994 by The Mount Sinai School of Medicine, manual modified by Donald Connor, Ph.D., and Kimberly Schafer, M.S. (3/98).

The ADAS-cog-11 test includes the following test items: (1) Word Recall, (2) Naming Objects/Fingers, (3) Commands, (4) Construction Praxis, (5) Ideational Praxis, (6) Orientation, (7) Word Recognition, (8) Remembering Test Instructions, (9) Spoken Language Ability, (10) Word Finding Difficulty, and (11) Comprehension.

The ADAS-cog-11 total score ranges from 0 to 70 (higher scores indicate more severe impairment). A decrease from baseline indicates improvement.

Cognitive Part of the Alzheimer's Disease Assessment Scale (ADAS-Cog-13)

The ADAS-Cog-13 is identical to the ADAS-Cog-11 assessment group (see above), with the addition of test items: Delayed Word Recall, and Digit (Number) Cancellation.

The ADAS-cog-13 total score ranges from 0 to 85 (higher scores indicate more severe impairment). A decrease from baseline indicates improvement.

Clinical Dementia Rating-Sum of Boxes CDR-SB

The CDR-SB test employed herein is based on the procedure developed by Hughs C D, Berg L, Danziger W L, Coben L A, and Martin R L. "*A new clinical scale for the staging of dementia*"; Br J Psychiatry. 1982; 140:566-572, and provides an assessment of six (6) dimensions: Memory, Orientation, Judgment and Problem Solving, Community Affairs, Home and Hobbies, and Personal Care.

Each of the six CDR dimensions are scored separately with well-defined anchors from 0 to 3.0 (no impairment to severe illness). The total sum of boxes ranges from 0 to 18. Higher totals indicate more severe impairment. A decrease from baseline indicates improvement.

Mini-Mental State Examination (MMSE)

The MMSE test employed herein is based on the procedure developed by Folstein, M., Folstein, S., McHugh, P. Mini-Mental State: "*A Practical Method for Grading the Cognitive State of Patients for the Clinician*"; Journal of Psychiatric Research 1975, 12:189-98.

The MMSE test assesses and/or evaluates memory, orientation, recognition, attention, concentration, language, and praxis. The MMSE total score ranges from 0 to 30 points. Lower scores indicate a lower level of functioning. An increase from baseline indicates improvement.

Controlled Oral Word Association Test (COWAT)

The COWAT test includes (1) asking the subject to name words beginning with a specific letter (e.g., F, A, S), (2) each of 3 trials is timed for 60 seconds, and (3) the score is calculated by the number of new words beginning with the assigned letter.

Category Fluency (Naming) Test (CNT or CFT)

The CNT test includes (1) asking the subject to name as many animals as possible within 60 seconds, and (2) the score is calculated by the number of distinct animals named.

Neuropsychiatric Inventory (NPI):

The NPI test employed herein is based on the procedure developed by J. L. Cummings and colleagues (UCLA), Neurology 44: 2308-2314, 1994.

The NPI assesses and/or evaluates 12 domains: (1) Delusions, (2) Hallucinations, (3) Agitation/Aggression, (4) Depression/Dysphoria, (5) Anxiety, (6) Euphoria, (7) Apathy, (8) Disinhibition, (9) Irritability/Lability, (10) Aberrant Motor Behavior, (11) Night-Time Behaviors, and (12) Appetite and Eating Change.

Only the first 10 domains are scored separately.

Alzheimer's Disease Cooperative Study Group-Activities of Daily Living Scale (ADCS-ADL, or sometimes referred to as ADCS-ADL-23):

The ADCS-ADL-23 test employed herein is based on the procedure developed by Galasko D, Bennett D, Sano M, et al., Alz Dis Assoc Disord (1997) 11(2): S33-S39.

The ADCS-ADL test assesses the actual performance of specific actions and behaviors by a patient as observed by a caregiver/informant.

Composite Scores—Three composite scores were calculated: (1) Composite Cognition Score (ADAS-cog Word Recall, Word Recognition, and Orientation, COWAT and CFT); (2) Memory Composite Score (ADAS-cog Word Recall, Word Recognition, and Orientation); and (3) Executive Function Composite Score (COWAT and CFT).

The composite score is only computed when all test scores are available. Calculations for the Composite Score will be made in the following way: (a) the mean and standard deviation (SD) of all individual Baseline scores is calculated for each test; (b) for each subject, the difference from the group mean Baseline scores is computed for each visit (score at visit−mean Baseline score) for each subject for each test; (c) for any test for which a negative difference score indicates an improvement in performance the difference from mean Baseline score is reversed (multiplied by −1), so that all outcome variables are in a uniform direction; (d) for each subject, the difference from the group mean Baseline is standardized by dividing the difference score by the relevant group Baseline SD for each test; (e) a combined cognition score is calculated by taking the average of the standardized scores across the tests; (f) for each subject, the mean and SD of the Baseline combined cognition scores is calculated; (g) the composite score is calculated by computing the difference from the group mean Baseline combined score (Post-Baseline visit combined score−Baseline mean combined score) and dividing it by the SD of the group Baseline combined scores; and (h) if one of the tests is not completed (i.e., missing) at Baseline and therefore does not contribute to the Baseline score, it will not be included in the composite calculations for any other visit for a single subject.

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A method of treating a patient having a cognitive impairment, comprising:
administering to the patient, for an extended period of at least 12 weeks, a daily dose of a pharmaceutical composition comprising (R)-7-chloro-N-(quinuclidin-3-yl)benzo[b]thiophene-2-carboxamide, or a pharmaceutically acceptable salt thereof;
wherein the cognitive impairment is limited cognitive impairment (LCI), mild cognitive impairment (MCI), Alzheimer's disease, or dementia of the Alzheimer's-type;
wherein the patient has scored a sub-normal value on one or more cognitive assessment tests, comprising: MMSE, ADAS-Cog-13, ADAS-Cog-11, COWAT, CFT, or CDR-SB.

2. The method of claim 1, wherein the Alzheimer's disease is mild-to-moderate Alzheimer's disease.

3. The method of claim 1, wherein the patient has scored a sub-normal value on one or more cognitive assessment tests, comprising: ADAS-Cog-13, ADAS-Cog-11, COWAT, CFT, or CDR-SB.

4. The method of claim 1, wherein the patient has scored a sub-normal value on an MMSE test.

5. The method of claim 1, wherein the patient has scored >14 to <24 on a MMSE test or a score of >2 on a CDR-SB test.

6. The method of claim 1, wherein the daily dose is between 1.0 mg and 4.5 mg of (R)-7-chloro-N-(quinuclidin-3-yl)benzo[b]thiophene-2-carboxamide, or a pharmaceutically acceptable salt thereof.

7. The method of claim 1, wherein the daily dose is 0.3 mg, 1.0 mg, 2.0 mg, or 3.0 mg, of (R)-7-chloro-N-(quinuclidin-3-yl)benzo[b]thiophene-2-carboxamide, or a pharmaceutically acceptable salt thereof.

8. The method of claim 1, wherein the extended period is at least 23 weeks.

9. The method of claim 1, wherein the extended period is at least 24 weeks.

10. The method of claim 1, wherein the method improves one or more cognitive or behavioral symptoms associated with the cognitive impairment.

11. The method of claim 1, wherein the method improves cognition in said cognitively impaired patient.

12. The method of claim 1, wherein the method provides a positive effect on cognition or a positive effect on clinical function in said cognitively impaired patient.

13. The method of claim 1, wherein the method provides a pro-cognitive effect in at least one of the following: visual motor, learning, delayed memory, or executive function, in said patient.

14. The method of claim 1, wherein said patient has been previously treated or is currently being treated with an AChEI.

15. The method of claim 1, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate.

16. The method of claim 1, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate, polymorph form I.

17. The method of claim 1, wherein the (R)-7-chloro-N-(quinuclidin-3-yl)benzo[b]thiophene-2-carboxamide, or a pharmaceutically acceptable salt thereof, is administered in the form of a pharmaceutical composition comprising at least one pharmaceutically acceptable carrier, excipient or diluent.

18. The method of claim 1, wherein the pharmaceutical composition is in the form of a tablet.

19. The method of claim 1, wherein the cognitive impairment is limited cognitive impairment (LCI).

20. The method of claim 1, wherein the cognitive impairment is mild cognitive impairment (MCI).

21. The method of claim 1, wherein the cognitive impairment is Alzheimer's disease.

22. The method of claim 1, wherein the cognitive impairment is dementia of the Alzheimer's-type.

23. A method of treating a patient having Alzheimer's disease, comprising:
administering to the patient, for an extended period of at least 23 weeks, a daily dose of between 1.0 mg and 4.5 mg of a pharmaceutical composition comprising (R)-7-chloro-N-(quinuclidin-3-yl)benzo[b]thiophene-2-carboxamide, or a pharmaceutically acceptable salt thereof;
wherein the patient has scored a sub-normal value on one or more cognitive assessment tests, comprising: MMSE, ADAS-Coq-13, ADAS-Coq-11, COWAT, CFT, or CDR-SB.

24. The method of claim 23, wherein the daily dose is 1.0 mg of the (R)-7-chloro-N-(quinuclidin-3-yl)benzo[b]thiophene-2-carboxamide, or pharmaceutically acceptable salt thereof.

25. The method of claim 23, wherein the daily dose is 2.0 mg of the (R)-7-chloro-N-(quinuclidin-3-yl)benzo[b]thiophene-2-carboxamide, or pharmaceutically acceptable salt thereof.

26. The method of claim 23, wherein the daily dose is 3.0 mg of the (R)-7-chloro-N-(quinuclidin-3-yl)benzo[b]thiophene-2-carboxamide, or pharmaceutically acceptable salt thereof.

27. The method of claim 23, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate.

28. The method of claim 23, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate, polymorph form I.

29. The method of claim 23, wherein the method improves one or more cognitive or behavioral symptoms associated with the Alzheimer's disease.

30. The method of claim 23, wherein the method improves cognition in said Alzheimer's disease patient.

31. The method of claim 23, wherein the method provides a positive effect on cognition or a positive effect on clinical function in said Alzheimer's disease patient.

32. A method of treating a patient having mild-to-moderate Alzheimer's disease, comprising:
administering to the patient, for an extended period of at least 23 weeks, a daily dose of between 1.0 mg and 4.5 mg of a pharmaceutical composition comprising (R)-7-chloro-N-(quinuclidin-3-yl)benzo[b]thiophene-2-carboxamide, or a pharmaceutically acceptable salt thereof;
wherein the patient has scored a sub-normal value on one or more cognitive assessment tests, comprising: MMSE, ADAS-Cog-13, ADAS-Cog-11, COWAT, CFT, or CDR-SB.

33. The method of claim 32, wherein the daily dose is 1.0 mg of the (R)-7-chloro-N-(quinuclidin-3-yl)benzo[b]thiophene-2-carboxamide, or pharmaceutically acceptable salt thereof.

34. The method of claim 32, wherein the daily dose is 2.0 mg of the (R)-7-chloro-N-(quinuclidin-3-yl)benzo[b]thiophene-2-carboxamide, or pharmaceutically acceptable salt thereof.

35. The method of claim 32, wherein the daily dose is 3.0 mg of the (R)-7-chloro-N-(quinuclidin-3-yl)benzo[b]thiophene-2-carboxamide, or pharmaceutically acceptable salt thereof.

36. The method of claim 32, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate.

37. The method of claim 32, wherein the pharmaceutically acceptable salt of the (R)-7-chloro-N-(quinuclidin-3-yl)benzo[b]thiophene-2-carboxamide, is (R)-7-chloro-N-(quinuclidin-3-yl)benzo[b]thiophene-2-carboxamide, hydrochloride, monohydrate, polymorph form I.

38. The method of claim 32, wherein the method improves one or more cognitive or behavioral symptoms associated with the mild-to-moderate Alzheimer's disease.

39. The method of claim 32, wherein the method improves cognition in said mild-to-moderate Alzheimer's disease patient.

40. The method of claim 32, wherein the method provides a positive effect on cognition or a positive effect on clinical function in said mild-to-moderate Alzheimer's disease patient.

* * * * *